United States Patent
Chang et al.

(10) Patent No.: US 9,896,688 B2
(45) Date of Patent: Feb. 20, 2018

(54) SHORT INTERFERING NUCLEIC ACID (SINA) MOLECULES CONTAINING A 2' INTERNUCLEOSIDE LINKAGE

(71) Applicant: SIRNA THERAPEUTICS, INC., Cambridge, MA (US)

(72) Inventors: Wonsuk Chang, Kenilworth, NJ (US); Erin N. Guidry, Kenilworth, NJ (US); Matthew G. Stanton, Rahway, NJ (US); Daniel Zewge, Rahway, NJ (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/769,361

(22) PCT Filed: Feb. 20, 2014

(86) PCT No.: PCT/US2014/017260
§ 371 (c)(1),
(2) Date: Aug. 20, 2015

(87) PCT Pub. No.: WO2014/130607
PCT Pub. Date: Aug. 28, 2014

(65) Prior Publication Data
US 2016/0068837 A1    Mar. 10, 2016

Related U.S. Application Data

(60) Provisional application No. 61/767,837, filed on Feb. 22, 2013.

(51) Int. Cl.
| | |
|---|---|
| C07H 21/04 | (2006.01) |
| C12N 15/113 | (2010.01) |
| C07H 21/00 | (2006.01) |
| C07H 21/02 | (2006.01) |
| C12N 15/11 | (2006.01) |
| C07H 19/10 | (2006.01) |

(52) U.S. Cl.
CPC .......... *C12N 15/113* (2013.01); *C07H 19/10* (2013.01); *C07H 21/00* (2013.01); *C07H 21/02* (2013.01); *C07H 21/04* (2013.01); *C12N 15/111* (2013.01); *C12N 2310/11* (2013.01); *C12N 2310/14* (2013.01); *C12N 2310/319* (2013.01)

(58) Field of Classification Search
None
See application file for complete search history.

(56) References Cited

U.S. PATENT DOCUMENTS

| | | |
|---|---|---|
| 5,863,905 A | 1/1999 | Suhadolnik et al. |
| 2011/0112168 A1 | 5/2011 | Feinstein et al. |
| 2013/0084576 A1 | 4/2013 | Prakash et al. |

FOREIGN PATENT DOCUMENTS

| | | |
|---|---|---|
| WO | 89/03683 A1 | 5/1989 |
| WO | 2011139699 A2 | 11/2011 |
| WO | 2011139702 A2 | 11/2011 |

OTHER PUBLICATIONS

Vickers et al. (The Journal of Biological Chemistry, 2003, 278:7108-7118).*
Charachon et al. "Phosphorothioate Analogues of (2'-5')(A)4: Agonist and Antagonist Activities in Intact Cells" Biochemistry (1990) vol. 29, pp. 2550-2556.
Giannaris et al. "Oligoribonucleotides containing 2',5'-phosphodiester linkages exhibit binding selectivity for 3',5'-RNA over 3',5'-ssDNA" Nucleic Acids Research (1993) vol. 21, No. 20, pp. 4742-4749.
Pauwels et al. "Biological Activity of New 2-5A Analogues" Chemica Scripta (1986) vol. 26, pp. 141-145.
Supplementary European Search Report for European application No. EP 14754069.4 dated Jun. 9, 2016.
International Search Report and Written Opinion from International Application No. PCT/US2014/017260 dated Jun. 3, 2014.
Whittaker et al., "Stereoselective Synthesis of Highly Functionalised P-Stereogenic Nucleosides via Palladium-Catalysed P—C Cross-Coupling Reactions", Tetrahedron Letters, 49:6984-6987 (2008).
Zhao et al., "Synthesis and Preliminary Biochemical Studies with 5'-Deoxy-5'-methylidyne Phosphonate Linked Thymidine Oligonucleotides", Tetrahedron Letters, vol. 37, No. 35, pp. 6239-6242 (1996).

* cited by examiner

*Primary Examiner* — Kimberly Chong
(74) *Attorney, Agent, or Firm* — Lando & Anastasi, LLP

(57) ABSTRACT

The present invention relates to RNAi molecules, and compositions thereof, comprising a 2' internucleoside linkage connecting the nucleotide at position 1 and the nucleotide at position 2 at the 5' end of the antisense strand. Specifically, the invention relates to single- and double-stranded short interfering nucleic acid (siNA) molecules that are capable of mediating RNA interference comprising 5' modified nucleotides that comprise, among other potential modifications, a 2' internucleoside linkage. The invention further relates to 5' modified nucleotides used as reagents to generate the RNAi molecules of the invention and methods of using the disclosed RNAi molecules.

16 Claims, 2 Drawing Sheets

SHORT INTERFERING NUCLEIC ACID (SINA) MOLECULES CONTAINING A 2' INTERNUCLEOSIDE LINKAGE

CROSS-REFERENCE TO RELATED APPLICATIONS

The present application is the U.S. National Phase Application under 35 U.S.C. § 371 of International Application No. PCT/US2014/017260, filed Feb. 20, 2014, which claims priority to U.S. Provisional Application No. 61/767,837, filed Feb. 22, 2013, which applications are hereby incorporated by reference herein in their entireties.

REFERENCE TO SEQUENCE LISTING

The sequence listing submitted via EFS-Web, in compliance with 37 CFR § 1.52(e)(5), is incorporated herein by reference. The sequence listing text file submitted via EFS contains the file A2038-7218US—Sequence Listing.txt, was created on Oct. 19, 2015, and is 115,716 bytes in size.

BACKGROUND OF THE INVENTION

RNA interference (RNAi) is an evolutionarily conserved cellular mechanism of post-transcriptional gene silencing found in fungi, plants and animals that uses small RNA molecules to inhibit gene expression in a sequence-specific manner. RNAi is controlled by the RNA-induced silencing complex (RISC) that is initiated by short double-stranded RNA molecules in a cell's cytoplasm. The short double-stranded RNA interacts with Argonaute 2 (Ago2), the catalytic component of RISC, which cleaves target mRNA that is complementary to the bound RNA. One of the two RNA strands, known as the guide strand, binds the Ago2 protein and directs gene silencing, while the other strand, known as the passenger strand, is degraded during RISC activation. See, for example, Zamore and Haley, 2005, *Science*, 309: 1519-1524; Vaughn and Martienssen, 2005, *Science*, 309: 1525-1526; Zamore et al., 2000, *Cell*, 101:25-33; Bass, 2001, *Nature*, 411:428-429; and, Elbashir et al., 2001, *Nature*, 411:494-498. Single-stranded short interfering RNA has also been shown to bind Ago2 and support cleavage activity (see, e.g., Lima et al., 2012, *Cell* 150:883-894). Importantly, the activity of single-stranded RNAi molecules should not be confused with that of single-stranded antisense RNA that inhibits translation of a complementary RNA in a stoichiometric fashion by base pairing to it, physically obstructing the translation machinery.

The RNAi machinery can be harnessed to destruct any mRNA of a known sequence. This allows for suppression (knock-down) of any gene from which it was generated, consequently preventing the synthesis of the target protein. Modulation of gene expression through an RNAi mechanism can be used to modulate therapeutically relevant biochemical pathways, including ones which are not accessible through traditional small molecule control. RNAi has also become a very important tool for target validation in the pharmaceutical industry.

Chemical modification of nucleotides incorporated into RNAi molecules leads to improved physical and biological properties, such as nuclease stability (see, e.g., Damha et al., 2008, *Drug Discovery Today*, 13:842-855), reduced immune stimulation (see, e.g., Sioud, 2006, *TRENDS in Molecular Medicine*, 12:167-176), enhanced binding (see, e.g., Koller, E. et al., 2006, *Nucleic Acid Research*, 34:4467-4476), and enhanced lipophilic character to improve cellular uptake and delivery to the cytoplasm. Thus, chemical modifications have the potential to increase potency of RNA compounds, allowing lower doses of administration, reducing the potential for toxicity, and decreasing overall cost of therapy.

While the sugar-phosphate backbone of most DNAs and RNAs are comprised of 3'-5' internucleoside phosphodiester linkages, the physiochemical and biochemical properties of 2'-5' linked ribonucleotides have been studied. Although not used for biological information storage, 2'-5' linked oligoribonucleotides support Watson-Crick base pairing and are formed naturally during intron splicing and in interferon treated cells (see, e.g., Jim et al., 1993, *Proc. Natl. Acad. Sci. USA*, 90:10568-10572; Sawai et al., 1996, *Biopolymers*, 39:173-182; Premraj et al., 2002, *Biophysical Chemistry*, 95:253-272; Johnston and Torrence (1984) in Interferons: Mechanism of Production and Action, Vol. 3 (Friedman, R. M., Ed.), pp. 189-298, Elsevier, Amsterdam). There has been interest in using 2'-5' linked oligoribonucleotides in antisense RNA applications as they exhibit the tendency to selectively hybridize with their RNA complements, rather than DNA complements (see, e.g., Hashimoto and Switcher, 1992, *J. Am. Chem. Soc.*, 114:6255-6256; Dougherty et al., 1992, *J. Am. Chem. Soc.*, 114:6265-6255), and display improved resistance toward several types of nucleases (see, e.g., Allul and Hoke, 1995, *Antisense Res. Develop.*, 5:3-11; Kandimalla et al., 1997, *Nucl. Acids Res.*, 25:370-378; Prakash et al., 1999, *Bioorg. Med. Chem. Lett.*, 9:2515-2520). However, there has been only limited study of the impact of 2'-5' linked ribonucleotides within RNAi oligonucleotides on the ability for such 2'-5' linked oligoribonucleotides to appropriately and efficiently degrade target gene expression through an Ago2-mediated RNAi pathway.

Prakish et al. (2006, *Bioorg. Med. Chem. Lett* 16:3238-3240) reported on the activity in mammalian cells of siRNA duplexes that have 2'-5' linked nucleotides. Results showed that an siRNA duplex comprising a 2'-5' linked antisense strand and a 3'-5' linked sense strand was not active in inhibiting mRNA expression, while an siRNA duplex with the reverse composition (i.e., a 3'-5' linked antisense strand and a 2'-5' linked sense strand) was active. They concluded that 2'-5' linkages are tolerated in the sense strand of siRNA duplexes but not in the antisense strand. Since the 5'-end of the antisense strand, in particular, is important for loading siRNA into RISC, positioning nucleation with mRNA and subsequent cleavage, the authors provide that it is likely crucial for the 5' end of the antisense strand to adopt correct geometry in order to appropriately interact with RISC. They conclude that 2'-5' internucleoside linkages at the 5' end of the antisense strand, thus, may not be capable of adopting the proper conformation to support that interaction.

PCT International application serial no. PCT/US2011/033961, published as WO 2011/139699 on Apr. 26, 2011, discloses 5' modified nucleosides and oligomeric compounds incorporating the modified nucleosides. The 5' modified nucleosides disclosed are preferably located at the 5' terminus of an oligonucleotide and have modifications at the 5' carbon of the sugar moiety of the nucleoside and, optionally, additional modifications at the 2' carbon. The 5' modified nucleosides disclosed in PCT/US2011/033961 are linked to an adjacent nucleoside by a traditional 3'-5' internucleoside linkage.

SUMMARY OF THE INVENTION

The instant disclosure provides novel single- or double-stranded small nucleic acid molecules capable of mediating RNA interference comprising an antisense strand that is complementary to a nucleic acid target and having a modified nucleotide at the 5' end comprising a 2' internucleoside linkage (e.g., 2'-5' internucleoside linkage). The single- or double stranded small nucleic acid molecules of the invention are more specifically referred to herein as short interfering nucleic acid (siNA) molecules, and the modified nucleotide at the 5' end of the antisense strand of said molecules is referred to herein as a 5' modified nucleotide. The 5' modified nucleotide makes up position 1 at the 5' end of the antisense strand of the siNA molecules of the invention (i.e., the first nucleotide of the 5' end of the strand). Novel 5' modified nucleotides for use as reagents to generate the siNA molecules disclosed herein are also part of the instant invention. The present invention further includes methods of modulating (e.g., inhibiting) the expression of genes, in vitro or in vivo, using siNA molecules disclosed herein and compositions thereof. Some embodiments of the siNA molecules of the invention are shown herein to display improved activity (see Examples, infra).

In one aspect, the present invention relates to short-interfering nucleic acid (siNA) molecules that are capable of mediating RNA interference (RNAi) and comprise an antisense strand having a 5' modified nucleotide. The antisense strand of the siNA molecules of the invention is either partially or completely complementary to a nucleic acid target. The siNA molecules of the invention can be single- or double-stranded small nucleic acid molecules and can take different oligonucleotide forms, including but not limited to short interfering RNA (siRNA), double-stranded RNA (dsRNA), micro-RNA (miRNA) and short hairpin RNA (shRNA) molecules. The 5' modified nucleotide at nucleotide position 1 of the antisense strand of the siNA molecules of the invention is linked to a nucleotide at position 2 of the strand through a 2' internucleoside linkage and may contain a modified 5' cap (i.e., other than a 5' phosphate cap). In particular, the short interfering nucleic acid (siNA) molecules of the invention comprise an antisense strand having a 5' modified nucleotide having the structure of Formula II:

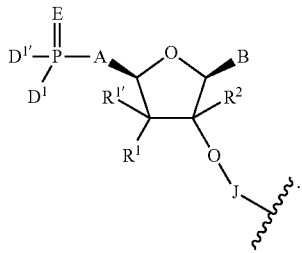

II wherein:

A is —OC($R^3$)$_2$—, —C($R^3$)$_2$O—, —C($R^3$)$_2$—, —C($R^3$)$_2$C($R^3$)$_2$— or —C$R^3$=C$R^3$—;

B is any heterocyclic base moiety;

$D^1$ and $D^{1'}$ are independently selected from hydroxyl, —O$R^4$, —S$R^4$, or —N($R^4$)$_2$;

E is O, S, —N$R^5$, —N—N($R^4$)$_2$ or —N—O$R^4$;

J is an internucleoside linking group linking the 5' modified nucleotide of Formula II to the sugar moiety of an adjacent nucleotide of the siNA molecule;

$R^1$ and $R^{1'}$ are independently selected from H, hydroxyl, halogen, $C_{1-6}$ alkyl, —O$R^6$, —N($R^6$)$_2$, or together form =O or =CH$_2$;

$R^2$ is H, $C_{1-6}$ alkyl or $C_{2-6}$ alkenyl;

$R^3$ and $R^5$ are independently selected from H, hydroxyl, halogen, $C_{1-10}$ alkyl, $C_{2-6}$ alkenyl, $C_{2-6}$ alkynyl, aryl,

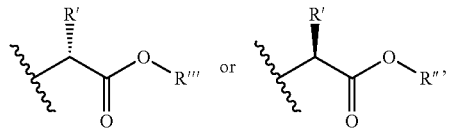

wherein R' is selected from H or $C_{1-4}$ alkyl (which is optionally substituted with one to three substituents independently selected from —S$R^{10}$, aryl, heteroaryl, amino, hydroxyl, oxo or —NH—C=(NH)NH$_2$, wherein the aryl and heteroaryl are optionally substituted with hydroxyl), and R" is selected from H, $C_{1-18}$ alkyl or aryl;

$R^4$ is independently selected from H, $C_{1-10}$ alkyl, $C_{2-6}$ alkenyl, $C_{2-6}$ alkynyl, aryl,

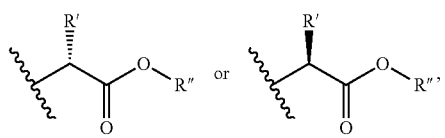

wherein R' is selected from H or $C_{1-4}$ alkyl (which is optionally substituted with one to three substituents independently selected from —S$R^{11}$, aryl, heteroaryl, amino, hydroxyl, oxo or —NH—C=(NH)NH$_2$, wherein the aryl and heteroaryl are optionally substituted with hydroxyl), and R" is selected from H, $C_{1-18}$ alkyl or aryl;

$R^6$ is independently selected from H, $C_{1-6}$ alkyl (which is optionally substituted with —O$R^7$, —S$R^7$, —N($R^8$)$_2$, or (=O)—N$R^9$ or from one to three halogen), $C_{2-6}$ alkenyl, $C_{2-6}$ alkynyl, aryl,

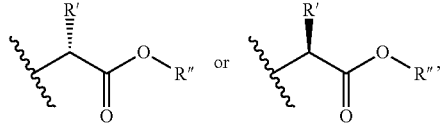

wherein R' is selected from H or $C_{1-4}$ alkyl (which is optionally substituted with one to three substituents independently selected from —S$R^{10}$, aryl, heteroaryl, amino, hydroxyl, oxo, —NH—C=(NH)NH$_2$, wherein the aryl and heteroaryl are optionally substituted with hydroxyl), and R" is selected from H, $C_{1-18}$ alkyl or aryl;

$R^7$ is methyl, —CF$_3$, —N($R^8$)$_2$ or —CH$_2$—N($R^8$)$_2$;

$R^8$ is independently selected from H or $C_{1-6}$ alkyl;

$R^9$ is ($R^8$)$_2$, —$R^8$—(CH$_2$)$_2$—N($R^8$)$_2$ or —$R^8$—C(=N$R^8$)[N($R^8$)$_2$]; and, $R^{10}$ is H or $C_{1-4}$ alkyl.

The siNA molecules of the invention can be single-stranded or double-stranded oligonucleotide molecules. The oligonucleotide molecules of the invention may inhibit gene expression in a cell or animal via an RNA interference (RNAi) mechanism.

In one aspect, the invention provides single-stranded short interfering nucleic acid (siNA) molecules, wherein the single oligonucleotide strand comprises a sequence that is complementary to at least part of a nucleic acid target sequence associated with gene expression. For purposes of this disclosure, the single strand of a single-stranded siNA molecule of the invention is referred to as the antisense strand.

In another aspect, the invention provides double-stranded short interfering nucleic acid (siNA) molecules, wherein a double-stranded siNA molecule comprises a sense and an antisense strand. The antisense strand comprises a sequence that is complementary to at least part of a nucleic acid target sequence associated with gene expression, and the sense strand is complementary to at least part of the antisense strand. The double-stranded siNA molecules of the invention can be symmetric or asymmetric.

In certain embodiments, the siNA molecules of the invention comprise an antisense strand that is complementary to a portion of a target nucleic acid sequence, wherein the target nucleic acid is selected from: a target mRNA, a target pre-mRNA, a target microRNA, and a target non-coding RNA. In certain embodiments, an siNA molecule of the invention is a microRNA mimetic.

In certain embodiments, the siNA molecules of the invention comprise an antisense strand having at least 15 nucleotides having sequence complementarity to a target nucleic acid sequence. In certain embodiments, the antisense strand of an siNA molecule of the invention is about 15 to 30 nucleotides in length. In other embodiments, a double-stranded siNA molecule of the invention comprises a sense strand and an antisense strand, wherein each strand is independently about 15 to 30 nucleotides in length.

In certain embodiments, the siNA molecules of the invention further comprise one or more additional nucleotides in either one or both strands of the molecule that are chemically-modified. Modifications include nucleic acid sugar modifications, base modifications, backbone (internucleoside linkage) modifications, non-nucleotide modifications, and/or any combination thereof. In certain embodiments, the siNA molecules of the invention comprise one or more modified internucleoside linking groups. In certain embodiments, each internucleoside linking group is, independently, a phosphodiester or phosphorothioate linking group. In certain embodiments, any one or more additional chemically-modified nucleotides in the antisense strand of either a single- or double-stranded siNA of the invention does not have a 2'-5' internucleoside linkage. In certain embodiments, the antisense strand of a single- or double-stranded siNA of the invention may contain up to 9 additional chemically-modified nucleotides with 2'-5' internucleoside linkages.

In certain embodiments, the double-stranded siNA molecules of the invention have 3' overhangs of one, two, three or four nucleotide(s) on one or both of the strands. In other embodiments, the double-stranded siNA molecules lack overhangs (i.e., have blunt ends).

In some embodiments, the siNA molecules of the invention have one or more terminal caps (also referred to herein as "caps"). For single-stranded siNA molecules of the invention, a cap may be present at the 3'-terminus (3'-cap). For double-stranded siNA molecules of the invention, a cap may be present at the 3'-terminus (3'-cap) of the antisense strand (guide strand), at the 5'-terminus (5'-cap) of the sense strand (passenger strand), and/or at 3'-terminus (3'-cap) of the sense strand (passenger strand).

The present invention further provides compositions comprising the siNA molecules described herein with, optionally, a pharmaceutically acceptable carrier or diluent. The administration of the composition can be carried out by known methods, wherein the nucleic acid is introduced into a desired target cell in vitro or in vivo.

The molecules and compositions of the present invention have utility over a broad range of applications related to modulating gene expression, including potential therapeutic applications. Thus, one aspect of this invention relates to the use of the molecules and compositions of the invention to inhibit gene expression in a cell via an RNAi mechanism. Methods comprise contacting a cell with a molecule or composition of the invention. In certain embodiments, such methods further comprise detecting RNAi activity. Detection and/or measuring of RNAi gene silencing activity may be direct or indirect.

Another aspect of this invention relates to administering the molecules and compositions of the invention to a subject (e.g., an animal). In this aspect of the invention, the molecules and compositions have the potential use of treating said subject, such as a human, who is suffering from a condition (such as cancer) which is mediated by the action, or by the loss of action, of a target nucleic acid or protein. In certain embodiments, the invention provides use of an siNA molecule of the invention for the manufacture of a medicament for the potential treatment of a disease by inhibiting gene expression.

The instant disclosure further provides novel 5' modified nucleotides that can be used to generate a single- or double-stranded siNA molecule as disclosed herein. When incorporated into an siNA molecule of the invention, the novel modified nucleotides, generally referred to herein as 5' modified nucleotides, make up position 1 at the 5' end of the antisense strand of the siNA molecule (i.e., the first nucleotide of the 5' end of the antisense strand), are linked to a nucleotide at position 2 of the strand through a 2' internucleoside linkage, and may contain a modified 5' cap (i.e., other than a 5' phosphate cap). In particular, the instant invention features 5' modified nucleotides having the structure of Formula I:

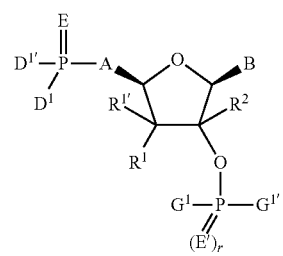

wherein:

A is —C(R$^3$)$_2$—, —C(R$^3$)$_2$C(R$^3$)$_2$— or —CR$^3$=CR$^3$—;

B is any heterocyclic base moiety;

D$^1$ and D$^{1'}$ are independently selected from hydroxyl, —OR$^4$, —SR$^4$, or —N(R$^4$)$_2$;

E and E' are independently selected from O, S, —NR$^5$, —N—N(R$^4$)$_2$ or —N—OR$^4$;

G$^1$ is hydroxyl or —OR$^6$;

G$^{1'}$ is hydroxyl, —OR$^6$ or —N(R$^6$)$_2$;

R$^1$ and R$^{1'}$ are independently selected from H, hydroxyl, halogen, C$_{1-6}$ alkyl, —OR$^7$, —N(R$^7$)$_2$, or together form =O or =CH$_2$;

R$^2$ is H, C$_{1-6}$ alkyl or C$_{2-6}$ alkenyl;

R$^3$ and R$^5$ are independently selected from H, hydroxyl, halogen, C$_{1-10}$ alkyl, C$_{2-6}$ alkenyl, C$_{2-6}$ alkynyl, aryl,

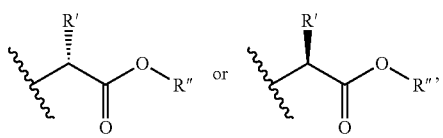

wherein R' is selected from H or $C_{1-4}$ alkyl (which is optionally substituted with one to three substituents independently selected from —$SR^{11}$, aryl, heteroaryl, amino, hydroxyl, oxo or —NH—C=(NH)$NH_2$, wherein the aryl and heteroaryl are optionally substituted with hydroxyl), and R" is selected from H, $C_{1-18}$ alkyl or aryl;

$R^4$ is independently selected from H, $C_{1-10}$ alkyl, $C_{2-6}$ alkenyl, $C_{2-6}$ alkynyl, aryl,

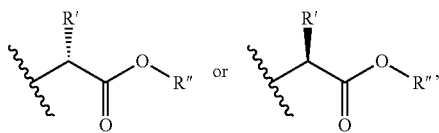

wherein R' is selected from H or $C_{1-4}$ alkyl (which is optionally substituted with one to three substituents independently selected from —$SR^{11}$, aryl, heteroaryl, amino, hydroxyl, oxo or —NH—C=(NH)$NH_2$, wherein the aryl and heteroaryl are optionally substituted with hydroxyl), and R" is selected from H, $C_{1-18}$ alkyl or aryl;

$R^6$ is independently $C_{1-6}$ alkyl, optionally substituted on the terminal carbon atom with cyano or a protecting group;

$R^7$ is independently selected from H, $C_{1-6}$ alkyl (which is optionally substituted with —$OR^8$, —$SR^8$, —$N(R^9)_2$, (=O)—$NR^{10}$ or from one to three halogen), $C_{2-6}$ alkenyl, $C_{2-6}$ alkynyl, aryl,

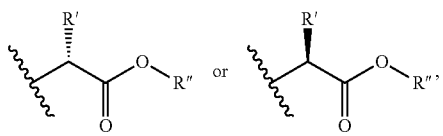

wherein R' is selected from H or $C_{1-4}$ alkyl (which is optionally substituted with one to three substituents independently selected from —$SR^{11}$, aryl, heteroaryl, amino, hydroxyl, oxo, —NH—C=(NH)$NH_2$, wherein the aryl and heteroaryl are optionally substituted with hydroxyl), and R" is selected from H, $C_{1-18}$ alkyl or aryl;

$R^8$ is methyl, —$CF_3$, —$N(R^9)_2$ or —$CH_2$—$N(R^9)_2$;

$R^9$ is independently selected from H or $C_{1-6}$ alkyl;

$R^{10}$ is $(R^9)_2$, —$R^9$—$(CH_2)_2$—$N(R^9)_2$ or —$R^9$—C(=$NR^9$)[$N(R^9)_2$];

$R^{11}$ is H or $C_{1-4}$ alkyl; and, r is 0 or 1.

These and other aspects of the invention will be apparent upon reference to the following Detailed Description and attached figures. Moreover, it is contemplated that any method or composition described herein can be implemented with respect to any other method or composition described herein and that different embodiments may be combined.

Additionally, patents, patent applications and other documents are cited throughout the specification to describe and more specifically set forth various aspects of this invention. Each of these references cited herein is hereby incorporated by reference in its entirety, including the drawings.

BRIEF DESCRIPTION OF THE DRAWINGS

FIG. 1 compares knock-down activity (ddCT) of a subset of single-stranded siNA molecules described in Table 2 at differing concentrations (100 nM, 10 nM, 1 nM and 0.1 nM). The knock-down activity was screened in Hepa1-6 cells transfected with RNAiMax (see Example 6).

DETAILED DESCRIPTION OF THE INVENTION

A. Terms and Definitions

Figure 1A:
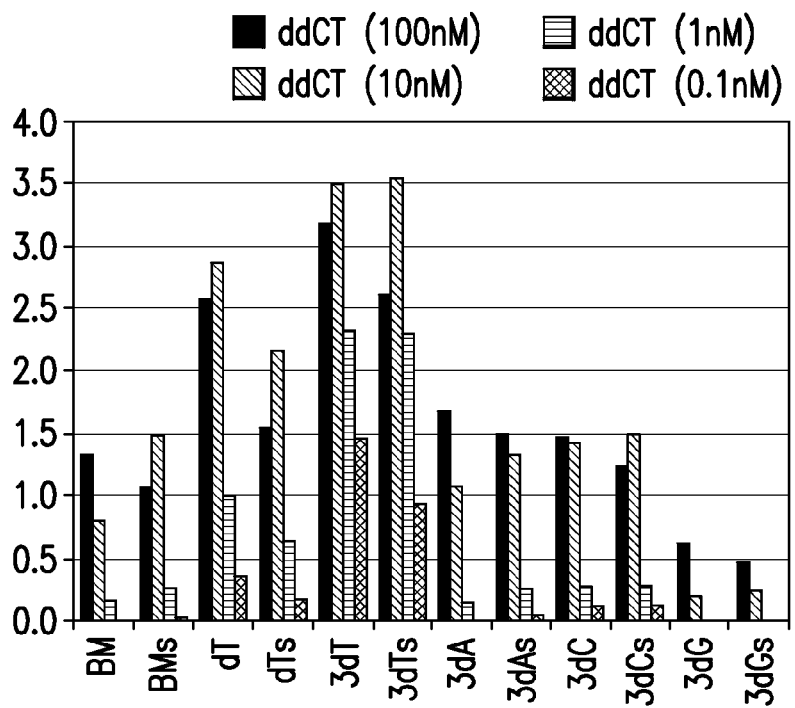
FIG. 1A compares the activity of single-stranded siNA molecules having 5'-position 1 nucleotides with regular 3'-5' internucleoside linkages (BM, BMs, dT, and dTs) to the activity of siNA molecules having 5'-position 1 nucleotides with 2'-5' internucleoside linkages (3dX and 3dXs, where X is T, A, C or G).

The following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as one tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The phrases "2'-modified nucleotide," "2'-substituted nucleotide" or a nucleotide having a modification at the "2'-position" of the sugar moiety, as used herein, generally refer to nucleotides comprising a substituent at the 2' carbon position of the sugar component that is other than H or OH. 2'-modified nucleotides include, but are not limited to, bicyclic nucleotides wherein the bridge connecting two carbon atoms of the sugar ring connects the 2' carbon and another carbon of the sugar ring; and nucleotides with non-bridging 2'substituents, such as allyl, amino, azido, thio, O-allyl, $OC_{1-10}$ alkyl, —OCF3, O—$(CH_2)_2$—O—$CH_3$, 2'-O $(CH_2)_2SCH_3$, O—$(CH_2)_2$—O—$N(R_m)(R_n)$, or O—$CH_2$—C (=O)—$N(R_m)(R_n)$, where each $R_m$ and $R_n$ is, independently, H or substituted or unsubstituted $C_{1-10}$ alkyl. 2'-modified nucleotides may further comprise other modifications, for example at other positions of the sugar and/or at the nucleobase. The phrases "3'-modified nucleotide," "3'-substituted nucleotide" or a nucleotide having a modification at the "3'-position" of the sugar moiety generally refers to a nucleotide comprising a modification, including a substituent, at the 3' carbon position of the sugar component.

The term "abasic" as used herein refers to its meaning as is generally accepted in the art. The term generally refers to sugar moieties lacking a nucleobase or having a hydrogen atom (H) or other non-nucleobase chemical groups in place of a nucleobase at the 1' position of the sugar moiety, see for example Adamic et al., U.S. Pat. No. 5,998,203. In one embodiment, an siNA molecule of the invention may contain an abasic moiety, wherein the abasic moiety is ribose, deoxyribose, or dideoxyribose sugar.

The term "acyclic nucleotide" as used herein refers to its meaning as is generally accepted in the art. The term generally refers to any nucleotide having an acyclic ribose sugar, for example where any of the ribose carbon/carbon or carbon/oxygen bonds are independently or in combination absent from the nucleotide.

If no number of carbon atoms is specified, the term "alkyl" refers to a saturated aliphatic hydrocarbon group, branched or straight-chain, containing from 1 to 10 carbon atoms. An alkyl group can have a specific number of carbon atoms. For example, $C_1$-$C_{10}$, as in "$C_1$-$C_{10}$ alkyl" or "$C_{1-10}$ alkyl," is defined to include groups having 1, 2, 3, 4, 5, 6, 7, 8, 9, or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

If no number of carbon atoms is specified, the term "alkenyl" refers to a non-aromatic hydrocarbon radical, straight or branched, containing from 2 to 10 carbon atoms and at least 1 carbon-to-carbon double bond. Preferably, one carbon-to-carbon double bond is present, and up to 4 non-aromatic carbon-carbon double bonds may be present. Thus, "$C_2$-$C_6$ alkenyl" or "$C_{2-6}$ alkenyl" means an alkenyl radical having from 2 to 6 carbon atoms. Alkenyl groups include ethenyl, propenyl, butenyl and cyclohexenyl. The straight, branched or cyclic portion of the alkenyl group may contain double bonds and may be substituted if a substituted alkenyl group is indicated. The term "cycloalkenyl" means a monocyclic hydrocarbon group having the specified number of carbon atoms and at least one point of internal unsaturation with a carbon-to-carbon double bond.

The term "alkynyl" refers to a hydrocarbon radical, straight or branched, containing from 2 to 10 carbon atoms, unless otherwise specified, and containing at least one carbon-to-carbon triple bond. Up to 3 carbon-carbon triple bonds may be present. Thus, "$C_2$-$C_6$ alkynyl" or "$C_{2-6}$ alkynyl" means an alkynyl radical having from 2 to 6 carbon atoms. Alkynyl groups include ethynyl, propynyl and butynyl. The straight or branched portion of the alkynyl group may contain triple bonds and may be substituted if a substituted alkynyl group is indicated.

The term "amino" refers to the group (—$NH_2$).

The term "antisense region" as used herein refers to its meaning as is generally accepted in the art. With reference to exemplary nucleic acid molecules of the invention, the term refers to a nucleotide sequence of an siNA molecule having complementarity to a target nucleic acid sequence. In addition, the antisense region of an siNA molecule can optionally comprise a nucleic acid sequence having complementarity to a sense region of the siNA molecule. In one embodiment, the antisense region of an siNA molecule is referred to as the antisense strand or guide strand.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "biodegradable" as used herein refers to its meaning as is generally accepted in the art. The term generally refers to degradation in a biological system, for example, enzymatic degradation or chemical degradation.

The term "biodegradable linker" as used herein refers to its meaning as is generally accepted in the art. With reference to nucleic acid molecules of the invention, the term refers to a linker molecule that is designed to connect one molecule to another molecule, and which is susceptible to degradation in a biological system. The linker can be a nucleic acid or a non-nucleic acid-based linker. For example, a biodegradable linker can be used to attach a ligand or biologically active molecule to an siNA molecule of the invention. Alternately, a biodegradable linker can be used to connect the sense and antisense strands of an siNA molecule of the invention. A biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. A biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidite or phosphodiester linkage. A biodegradable nucleic acid linker molecule can also comprise nucleic acid backbone, nucleic acid sugar, or nucleic acid base modifications.

The term "biologically active molecule" as used herein refers to its meaning as is generally accepted in the art. With reference to exemplary nucleic acid molecules of the invention, the term refers to compounds or molecules that are capable of eliciting or modifying a biological response in a system and/or are capable of modulating the pharmacokinetics and/or pharmacodynamics of other biologically active molecules. Examples of biologically active molecules, include siNA molecules alone or in combination with other molecules including, but not limited to, therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, polyamines, polyamides, polyethylene glycol, other polyethers, 2-5A chimeras, siNA, dsRNA, allozymes, aptamers, decoys and analogs thereof.

The term "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The term "blunt end" as used herein refers to its meaning as is generally accepted in the art. With reference to nucleic acid molecules of the invention, the term refers to termini of a double-stranded siNA molecule having no overhanging nucleotides. For example, the two strands of a double-stranded siNA molecule having blunt ends align with each other with matched base-pairs without overhanging nucleotides at the termini. An siNA duplex molecule of the invention can comprise blunt ends at one or both termini of the duplex, such as termini located at the 5'-end of the antisense strand, the 5'-end of the sense strand, or both termini of the duplex.

The term "cap" (also referred to herein as "terminal cap") as used herein refers to its meaning as is generally accepted in the art. With reference to exemplary nucleic acid molecules of the invention, the term refers to a moiety, which can be a chemically-modified nucleotide or a non-nucleotide, incorporated at one or more termini of the nucleic acid molecules of the invention. These terminal modifications may protect the nucleic acid molecule from exonuclease degradation and may help in delivery and/or localization of the nucleic acid molecule within a cell. The cap can be present at a 5'-terminus (5'-cap) or 3'-terminus (3'-cap) of a strand of the nucleic acid molecules of the invention, or can be present on both termini. For example, a cap can be present at the 5'-end, 3'-end and/or 5' and 3'-ends of the sense strand of a nucleic acid molecule of the invention. Additionally, a cap can be present at the 3'-end of the antisense strand of a nucleic acid molecule of the invention. In non-limiting examples, a 5'-cap includes, but is not limited to, LNA; glyceryl; inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide; 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Non-limiting examples of a 3'-cap include, but are not limited to, LNA; glyceryl; inverted deoxy abasic residue (moiety); 4',5'-methylene nucleotide; 1-(beta-D-erythrofuranosyl) nucleotide; 4'-thio nucleotide; carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate; phosphorothioate and/or phosphorodithioate; bridging or non-bridging methylphosphonate; and 5'-mercapto moieties (for more details see Beaucage and Iyer, 1993, *Tetrahedron* 49, 1925; incorporated by reference herein). In one embodiment, siNA molecules of the present invention contain a vinyl phosphate 5' terminal cap, wherein carbon 5 of the sugar ring contains the following substituent (=CH)—P(=O)(OH)$_2$.

The term "cell" as used herein refers to its meaning as is generally accepted in the art. With reference to exemplary nucleic acid molecules of the invention, the term is used in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The phrases "chemically-modified nucleotide," "modified nucleotide" or, when used in reference to nucleotides of the invention, "chemical modification," refer to a nucleotide that contains a modification in the chemical structure of the heterocyclic base moiety, sugar and/or phosphate of the unmodified (or natural) nucleotide as is generally known in the art (i.e., at least one modification compared to a naturally occurring RNA or DNA nucleotide). In certain embodiments, the terms can refer to certain forms of RNA that are naturally occurring in certain biological systems, for example 2'-O-methyl modifications or inosine modifications. A modified nucleotide includes abasic nucleotides. Modified nucleotides include nucleotides with a modified sugar ring or sugar surrogate. Modified heterocyclic base moieties include without limitation, universal bases, hydrophobic bases, promiscuous bases, size-expanded bases, and fluorinated bases as defined herein. Certain of these nucleobases are particularly useful for increasing the binding affinity of the siNA molecules as provided herein. These include 5-substituted pyrimidines, 6-azapyrimidines and N-2, N-6 and 0-6 substituted purines, including 2-aminopropyladenine, 5-propynyluracil and 5-propynylcytosine. A modified internucleoside linkage refers to any internucleoside linkage other than a naturally occurring internucleoside linkage. Non-limiting examples of modified nucleotides are described herein and in U.S. application Ser. No. 12/064,014 (published as US 20090176725).

The terms "complementarity" or "complementary" as used herein refers to its meaning as is generally accepted in the art. With reference to exemplary nucleic acid molecules of the invention, the terms generally refer to the formation or existence of hydrogen bond(s) between one nucleic acid sequence and another nucleic acid sequence by either traditional Watson-Crick or other non-traditional types of bonding as described herein. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol. LII pp.* 123-133; Frier et al., 1986, *Proc. Nat. Acad. Sci.* USA 83:9373-9377; Turner et al., 1987, *J. Am.*

Chem. Soc. 109:3783-3785). Perfect complementary means that all the contiguous residues of a nucleic acid sequence will hydrogen bond with the same number of contiguous residues in a second nucleic acid sequence. Partial complementarity can include various mismatches or non-based paired nucleotides (e.g., 1, 2, 3, 4, 5, 6, 7, 8, 9, 10 or more mismatches, non-nucleotide linkers, or non-based paired nucleotides) within the nucleic acid molecule, which can result in bulges, loops, or overhangs between the sense strand or sense region and the antisense strand or antisense region of a nucleic acid molecule or between the antisense strand or antisense region of a nucleic acid molecule and a corresponding target nucleic acid molecule. Such partial complementarity can be represented by a % complementarity that is determined by the number of non-base paired nucleotides, e.g., about 50%, 60%, 70%, 80%, 90% etc. depending on the total number of nucleotides involved. Such partial complementarity is permitted to the extent that the nucleic acid molecule (e.g., siNA) maintains its function, for example the ability to mediate sequence specific RNAi.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. Non-limiting examples of agents suitable for formulation with the nucleic acid molecules of the instant invention include: lipid nanoparticles (see for example Semple et al., 2010, *Nat Biotechnol.*, 28(2):172-6); P-glycoprotein inhibitors (such as Pluronic P85); biodegradable polymers, such as poly (DL-lactide-coglycolide) microspheres for sustained release delivery (Emerich, D F et al., 1999, *Cell Transplant*, 8, 47-58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058. A "pharmaceutically acceptable composition" or "pharmaceutically acceptable formulation" can refer to a composition or formulation that allows for the effective distribution of the nucleic acid molecules of the instant invention to the physical location most suitable for their desired activity.

The term "conjugate" refers to an atom or group of atoms bound to an siNA molecule of the invention. In general, conjugate groups modify one or more properties of the molecule to which they are attached, including, but not limited to pharmacodynamics, pharmacokinetic, binding, absorption, cellular distribution, cellular uptake, charge and clearance. Conjugate groups are routinely used in the chemical arts and are linked directly or via an optional linking moiety or linking group to the parent compound, such as an siNA molecule. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are attached to a 3' or 5' terminal nucleotide or to an internal nucleotides of an siNA molecule. As used herein, "conjugate linking group" refers to any atom or group of atoms used to attach a conjugate to an siNA molecule. Linking groups or bifunctional linking moieties such as those known in the art are amenable to the present invention.

The term "cyano" refers to the group (—CN).

The terms "detecting" or "measuring," as used herein in connection with an activity, response or effect, indicate that a test for detecting or measuring such activity, response, or effect is performed. Such detection and/or measuring may include values of zero. Thus, if a test for detection or measuring results in a finding of no activity (activity of zero), the step of detecting or measuring the activity has nevertheless been performed. For example, in certain embodiments, the present invention provides methods that comprise steps of detecting gene silencing activity. Any such step may include values of zero.

The term "expression" as used herein refers to its meaning as is generally accepted in the art. The term generally refers to the process by which a gene ultimately results in a protein. Expression includes, but is not limited to, transcription, splicing, post-transcriptional modification and translation.

The term "gene" as used herein refers to its meaning as is generally accepted in the art. The term generally refers to a nucleic acid (e.g., DNA or RNA) sequence that comprises partial length or entire length coding sequences necessary for the production of a polypeptide. A gene can also include the UTR or non-coding region of the nucleic acid sequence. A gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Aberrant fRNA or ncRNA activity leading to disease can therefore be modulated by siNA molecules of the invention. siNA molecules targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The term "gene" can be used when referencing a gene to which an siNA molecule of the invention is either directly (i.e., the siNA molecule comprises an antisense strand having partial or complete complementarity to the gene) or indirectly (i.e., the siNA molecule comprises an antisense strand having partial or complete complementarity to a gene in the expression or activity pathway of the gene) targeted.

As appreciated by those of skill in the art, "halo" or "halogen" as used herein is intended to include chloro, fluoro, bromo and iodo.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl," as used herein, is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "hydroxyl" refers to the group (—OH).

The terms "including" (and any form thereof, such as "includes" and "include"), "comprising" (and any form thereof, such as "has" or "have") or "containing" (and any form thereof ("contains" or "contain") are inclusive and open-ended and do not exclude additional, unrecited elements or method steps.

The terms "inhibit," "down-regulate," or "reduce" as used herein refer to their meanings as generally accepted in the art. With reference to nucleic acid molecules of the invention, the term generally refers to reduction in the expression of a gene, or in the level of RNA molecules or equivalent RNA molecules encoding one or more proteins or protein subunits, or in the activity of one or more proteins or protein subunits, below that observed in the absence of the nucleic acid molecules (e.g., siNA) of the invention. Down-regulation can be associated with post-transcriptional silencing, such as RNAi mediated cleavage.

The terms "intermittent" or "intermittently" as used herein refer to their meaning as generally accepted in the art. The terms generally refer to periodic stopping and starting at either regular or irregular intervals.

The terms "internucleoside linkage," "internucleoside linker," "internucleoside linking group," "internucleotide linkage," "internucleotide linker" or "internucleotide linking group" are used herein interchangeably and refer to any linker or linkage between two nucleoside (i.e., a heterocyclic base moiety and a sugar moiety) units, as is known in the art, including, for example, but not as limitation, phosphate, analogs of phosphate, phosphonate, guanidium, hydroxylamine, hydroxylhydrazinyl, amide, carbamate, alkyl, and substituted alkyl linkages. Internucleoside linkages constitute the backbone of a nucleic acid molecule. In one aspect, a nucleotide of an siNA molecule of the invention may be linked to a consecutive nucleotide through a linkage between the 3'-carbon of the sugar of the first nucleotide and the sugar moiety of the second nucleotide (herein referred to as a 3' internucleoside linkage). A 3'-5' internucleoside linkage, as used herein, refers to an internucleoside linkage that links two consecutive nucleoside units, wherein the linkage is between the 3' carbon of the sugar moiety of the first nucleoside and the 5' carbon of the sugar moiety of the second nucleoside. In another aspect, a nucleotide of an siNA molecule of the invention may be linked to a consecutive nucleotide through a linkage between the 2'-carbon of the sugar of the first nucleotide and the sugar moiety of the second nucleotide (herein referred to as a 2' internucleoside linkage). A 2'-5' internucleoside linkage, as used herein, refers to an internucleoside linkage that links two consecutive nucleoside units, wherein the linkage is between the 2' carbon of the sugar moiety of the first nucleoside and the 5' carbon of the sugar moiety of the second nucleoside.

The terms "mammalian" or "mammal" as used herein refers to their meanings as generally accepted in the art. The terms generally refer to any warm blooded vertebrate species, such as a human, mouse, rat, dog, cat, hamster, guinea pig, rabbit, livestock, and the like.

The phrase "metered dose inhaler" or "MDI" refers to a unit comprising a can, a secured cap covering the can, and a formulation metering valve situated in the cap. MDI systems include a suitable channeling device. Suitable channeling devices comprise for example, a valve actuator and a cylindrical or cone-like passage through which medicament can be delivered from the filled canister via the metering valve to the nose or mouth of a patient such as a mouthpiece actuator.

The term "microRNA" or "miRNA" as used herein refers to its meaning as is generally accepted in the art. The term generally refers to a small non-coding RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research, 102, 3-9; He et al., 2004, Nat. Rev. Genet., 5, 522-531; Ying et al., 2004, Gene, 342, 25-28; and Sethupathy et al., 2006, RNA, 12:192-197). The phenomenon of RNA interference includes the endogenously induced gene silencing effects of miRNAs. As used herein, "microRNA mimetic" refers to an siNA molecule having a sequence that is at least partially identical to that of a microRNA. In certain embodiments, a microRNA mimetic comprises the microRNA seed region of a microRNA. In certain embodiments, a microRNA mimetic modulates translation of more than one target nucleic acid.

The term "modulate" or "modulation" as used herein refers to its meaning as is generally accepted in the art. With reference to nucleic acid molecules of the invention, the term refers to when the expression of a gene, or the level of one or more RNA molecules (coding or non-coding), or the activity of one or more RNA molecules or proteins or protein subunits, is up-regulated or down-regulated, such that expression level or activity is greater than or less than that observed in the absence of the molecule that effects modulation. For example, the term "modulate" in some embodiments can refer to inhibition and, in other embodiments, can refer to potentiation or up-regulation, e.g., of gene expression.

The phrase "non-base paired" refers to nucleotides that are not base paired between the sense strand or sense region and the antisense strand or antisense region of a double-stranded siNA molecule. Non-base paired nucleotides can include, for example, but not as limitation, mismatches, overhangs, and single stranded loops.

The term "non-nucleotide" refers to any group or compound which can be incorporated into a polynucleotide chain in the place of one or more nucleotide units, such as for example but not limitation, abasic moieties or alkyl chains. The group or compound is "abasic" in that it does not contain a commonly recognized nucleotide base, such as adenosine, guanine, cytosine, uracil or thymine and, therefore, lacks a nucleobase at the 1'-position.

The term "nucleobase" is used herein to refer to the heterocyclic base portion of a nucleotide. Nucleobases may be naturally occurring or may be modified. In certain embodiments, a nucleobase may comprise any atom or group of atoms capable of hydrogen bonding to a base of another nucleic acid.

The term "nucleotide" is used as is generally recognized in the art. Nucleotides generally comprise a heterocyclic base moiety (i.e., a nucleobase), a sugar, and an internucleoside linkage, e.g., a phosphate. The base can be a natural base (standard), a modified base, or a base analog, as are well known in the art. Such bases are generally located at the 1' position of a nucleotide sugar moiety. Additionally, the nucleotides can be unmodified or modified at the sugar, internucleoside linkage, and/or base moiety, (also referred to interchangeably as nucleotide analogs, modified nucleotides, non-natural nucleotides, non-standard nucleotides and others; see, for example, U.S. application Ser. No. 12/064,014 (published as US 20090176725)). A naturally occurring internucleoside linkage refers to a 3' to 5' phosphodiester linkage (also referred to herein as a 3'-5' phosphodiester linkage).

The term "overhang" as used herein refers to its meaning as is generally accepted in the art. With reference to exemplary double stranded nucleic acid molecules, the term generally refers to the terminal portion of a nucleotide sequence that is not base paired between the two strands of a double-stranded nucleic acid molecule. Overhangs, when present, are typically at the 3'-end of one or both strands in an siNA duplex.

The term "oxo" refers to the group (=O).

The term "parenteral" as used herein refers to its meaning as is generally accepted in the art. The term generally refers to methods or techniques of administering a molecule, drug, agent, or compound in a manner other than through the digestive tract, and includes epicutaneous, subcutaneous, intravascular (e.g., intravenous), intramuscular, or intrathecal injection or infusion techniques and the like.

The phrase "pharmaceutically acceptable carrier or diluent" as used herein refers to its meaning as it generally accepted in the art. The phrase generally refers to any substance suitable for use in administering to an animal. In certain embodiments, a pharmaceutically acceptable carrier or diluent is sterile saline. In certain embodiments, such sterile saline is pharmaceutical grade saline.

The term "phosphorothioate" refers to an internucleoside phosphate linkage comprising one or more sulfur atoms in place of an oxygen atom. Hence, the term phosphorothioate refers to both phosphorothioate and phosphorodithioate internucleoside linkages.

The term "position 1" refers to the position of the first nucleotide at the 5' end of an oligonucleotide strand, e.g., antisense strand. All positions referred to herein are the positions of a nucleotide counting from the 5' end of an oligonucleotide strand, for example, positions 1-3 of an antisense strand refer to the three nucleotides at positions 1, 2, and 3 counting from the 5' end of the antisense strand. The term "5'-position 1 nucleotide" refers to the nucleotide at position 1 of an oligonucleotide strand that may or may not contain a 5' cap. By way of example, a 5' cap of a 5'-position 1 nucleotide can be a naturally-occurring 5' phosphate cap or a modified terminal cap, as defined herein. The term "position 21-3' nucleotide" refers to the nucleotide at position 21 of an oligonucleotide strand that may or may not further contain a 3' cap.

The term "protecting group," as used herein, refers to a labile chemical moiety that is known in the art to protect reactive groups, including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007. Groups can be selectively incorporated into oligomeric compounds as provided herein as precursors. For example, an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al, Protocols for Oligonucleotide Conjugates, Humana Press; New Jersey, 1994, 26, 1-72.

Examples of hydroxyl protecting groups include, without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), Irimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include, without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of protecting groups commonly used to protect phosphate and phosphorus groups include without limitation, methyl, ethyl, benzyl (Bn), phenyl, isopropyl, fert-butyl, allyl, cyclohexyl (cHex), 4-methoxybenzyl, 4-chlorobenzyl, 4-nitrobenzyl, 4-acyloxybenzyl, 2-methylphenyl, 2,6-dimethylphenyl, 2-chlorophenyl, diphenylmethyl, 4-methylthio-1-butyl, 2-(S-Acetylthio)ethyl (SATE), 2-cyanoethyl, 2-cyano-1,1-dimethylethyl (CDM), 4-cyano-2-butenyl, 2-(trimethylsilyl)ethyl (TSE), 2-(phenylthio)ethyl, 2-(triphenylsilyl)ethyl, 2-(benzylsulfonyl)ethyl, 2,2,2-trichloroethyl, 2,2,2-tribromoethyl, 2,3-dibromopropyl, 2,2,2-trifluoroethyl, thiophenyl, 2-chloro-4-tritylphenyl, 2-bromophenyl, 2-[N-isopropyl-N-(4-methoxybenzoyl)amino]ethyl, 4-(N-trifluoroacetylamino)butyl, 4-oxopentyl, 4-tritylaminophenyl, 4-benzylaminophenyl and morpholino. Wherein more commonly used phosphate and phosphorus protecting groups include without limitation, methyl, ethyl, benzyl (Bn), phenyl, isopropyl, tert-butyl, 4-methoxybenzyl, 4-chlorobenzyl, 2-chlorophenyl and 2-cyanoethyl.

Examples of amino protecting groups include, without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like. In certain embodiments, siNA molecules as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., Tetrahedron, 1993, 49(10), 1925-1963; Beaucage et al, Tetrahedron, 1993, 49(46), 10441-10488; Beaucage et al, Tetrahedron, 1992, 48(12), 2223-2311.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is provided from the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield phosphodiester or phosphorothioate internucleoside linkages. Additional reactive phosphates and phosphites are disclosed in Tetrahedron Report Number 309 (Beaucage and Iyer, Tetrahedron, 1992, 48, 2223-2311).

The term "ribonucleotide" as used herein refers to its meaning as is generally accepted in the art. The term generally refers to a nucleotide with a hydroxyl group at the 2' position of a β-D-ribofuranose moiety.

The term "RNA" as used herein refers to its generally accepted meaning in the art. Generally, the term RNA refers to a molecule comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of an siNA molecule or internally, for example at one or more nucleotides of the RNA. Nucleotides in the nucleic acid molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "RNA interference" or term "RNAi" refer to the biological process generally known in the art of inhibiting or down regulating gene expression in a cell, typically by causing destruction of specific target RNA and mediated by sequence-specific nucleic acid molecules (e.g., short interfering nucleic acid molecule), see for example Zamore and Haley, 2005, *Science*, 309, 1519-1524; Vaughn and Martiensen, 2005, *Science*, 309, 1525-1526; Zamore et al., 2000, *Cell*, 101, 25-33; Bass, 2001, *Nature*, 411, 428-429; Elbashir et al., 2001, *Nature*, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237; Hutvagner and Zamore, 2002, *Science*, 297, 2056-60; McManus et al., 2002, *RNA*, 8, 842-850; Reinhart et al., 2002, *Gene & Dev.*, 16, 1616-1626; and Reinhart & Bartel, 2002, *Science*, 297, 1831). Additionally, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at either the post-transcriptional level or the pre-transcriptional level. In a non-limiting example, epigenetic modulation of gene expression by siNA molecules of the invention can result from siNA mediated modification of chromatin structure or methylation patterns to alter gene expression (see, for example, Verdel et al., 2004, *Science*, 303, 672-676; Pal-Bhadra et al., 2004, *Science*, 303, 669-672; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237). Modulation of gene expression by siNA molecules of the invention can result from siNA mediated cleavage of RNA (either coding or non-coding RNA) via RISC.

The phrase "seed region" as used herein refers to its meaning as is generally accepted in the art. Generally, the phrase refers to a region at or near the 5' end of an antisense strand of an siNA molecule having a nucleobase sequence that is important for target nucleic acid recognition by the molecule. In certain embodiments, a seed region comprises nucleotides 2-8 (i.e., located from positions 2-8) of an siNA molecule. In certain embodiments, a seed region comprises nucleotides 2-7 of an siNA molecule. In certain embodiments, a seed region comprises nucleotides 1-7 of an siNA molecule. In certain embodiments, a seed region comprises nucleotides 1-6 of an siNA molecule. In certain embodiments, a seed region comprises nucleotides 1-8 of an siNA molecule. As used herein, "microRNA seed region" refers to a seed region of a microRNA or microRNA mimetic.

The phrase "sense region" as used herein refers to its meaning as is generally accepted in the art. With reference to nucleic acid molecules of the invention, the term refers to a nucleotide sequence of an siNA molecule having complementarity to an antisense region of the siNA molecule. In addition, the sense region of a siNA molecule can comprise a nucleic acid sequence having homology or sequence identity with a target nucleic acid sequence. In one embodiment, the sense region of the siNA molecule is also referred to as the sense strand or passenger strand.

The phrases "short interfering nucleic acid," "siNA," "siNA molecule," "short interfering RNA," "siRNA," "short interfering nucleic acid molecule," "short interfering oligonucleotide molecule," or "chemically modified short interfering nucleic acid molecule" refer to any nucleic acid molecule capable of inhibiting or down regulating gene expression or viral replication by mediating RNA interference ("RNAi") in a sequence-specific manner. These terms can refer to both individual nucleic acid molecules, a plurality of such nucleic acid molecules, or pools of such nucleic acid molecules. The siNA can be a symmetric or asymmetric double-stranded nucleic acid molecule comprising self-complementary sense and antisense strands or regions, wherein the antisense strand/region comprises a nucleotide sequence that is complementary to a nucleotide sequence in a target nucleic acid molecule or a portion thereof, and the sense strand/region comprises a nucleotide sequence corresponding to the target nucleic acid sequence or a portion thereof. A symmetric duplex refers to an siNA molecule comprising sense and antisense regions each comprising the same number of nucleotides. An asymmetric duplex refers to an siNA molecule comprising an antisense region and a sense region that comprises fewer nucleotides than the antisense region, to the extent that the sense region has enough complementary nucleotides to base pair with the antisense region to form a duplex. For example, an asymmetric double-stranded siNA molecule of the invention can comprise an antisense region having length sufficient to mediate RNAi in a cell or in vitro system, e.g. about 15 to about 30, and a sense region having about 3 to about 25 nucleotides that are complementary to the antisense region. As an example, an asymmetric double-stranded hairpin siNA molecule can also comprise a loop region comprising about 4 to about 12 nucleotides. The loop portion of an asymmetric hairpin siNA molecule can comprise nucleotides, non-nucleotides, linker molecules, or conjugate molecules as described herein. An siNA molecule of the invention can also comprise a single-stranded polynucleotide having a nucleotide sequence complementary to a portion of a nucleotide sequence in a target nucleic acid molecule (for example, where such siNA molecule does not require the presence within the siNA molecule of a nucleotide sequence corresponding to the target nucleic acid sequence or a portion thereof). A single-stranded siNA molecule is an RNAi molecule, functioning through an RNAi mechanism.

The term "subject" as used herein refers to its meaning as is generally accepted in the art. The term generally refers to an organism to which the nucleic acid molecules of the invention can be administered. A subject can be a mammal or mammalian cells, including human or human cells. The term also refers to an organism which is a donor or recipient of explanted cells or the cells themselves.

The term "sugar moiety" means a natural or modified sugar ring or sugar surrogate.

The term "sugar surrogate" generally refers to a structure that is capable of replacing the furanose ring of a naturally occurring nucleotide. In certain embodiments, sugar surrogates are non-furanose (or 4'-substituted furanose) rings or ring systems or open systems. Such structures include simple changes relative to the natural furanose ring, such as a 6-membered ring or may be more complicated as is the case with the non-ring system used in peptide nucleic acid. Sugar surrogates includes without limitation morpholinos, cyclohexenyls and cyclohexitols. In most nucleotides having a sugar surrogate group, the heterocyclic base moiety is generally maintained to permit hybridization.

The phrase "systemic administration" as used herein refers to its meaning as is generally accepted in the art. The term generally refers in vivo systemic absorption or accumulation of drugs in the blood stream followed by distribution throughout the entire body.

The term "target" cellular protein, peptide, or polypeptide, or polynucleotide or nucleic acid (such as "target DNA," "target RNA," "target nucleic acid"), as used herein, refers to a protein or nucleic acid, respectively, of which siNA molecule of the invention may be capable of inhibiting or down regulating the expression. In certain embodiments, target RNA is mRNA, pre-mRNA, non-coding RNA, pri-microRNA, pre-microRNA, mature microRNA, promoter-directed RNA, or natural antisense transcripts. A target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, *Science*, 300, 258-260. For example, a target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid. As used herein, "target mRNA" refers to a pre-selected RNA molecule that encodes a protein. As used herein, "target pre-mRNA" refers to a pre-selected RNA transcript that has not been fully processed into mRNA. Notably, pre-RNA includes one or more intron. As used herein, "target microRNA" refers to a pre-selected non-coding RNA molecule about 18-30 nucleobases in length that modulates expression of one or more proteins or to a precursor of such a non-coding molecule. As used herein, "target pdRNA" refers to a pre-selected RNA molecule that interacts with one or more promoter to modulate transcription. As used herein, "target non-coding RNA" refers to a pre-selected RNA molecule that is not translated to generate a protein. Certain non-coding RNA is involved in regulation of expression. The phrase "pathway target" refers to any target involved in pathways of gene expression or activity. For example, any given target can have related pathway targets that can include upstream, downstream, or modifier genes in a biologic pathway. These pathway target genes can provide additive or synergistic effects in the treatment of diseases, conditions, and traits herein.

The phrases "target site," "target sequence" and "target nucleic acid site" as used herein refer to their meanings as generally accepted in the art. The term generally refers to a sequence within a target nucleic acid (e.g., RNA) that is "targeted," e.g., for cleavage mediated by an siNA molecule that contains sequences within its antisense region that are complementary to the target sequence.

The phrase "therapeutically effective amount" as used herein refers to its meaning as is generally accepted in the art. The term generally refers to the amount of a molecule, compound or composition that will elicit the biological or medical response of a cell, tissue, system, animal or human that is be sought by the researcher, veterinarian, medical doctor or other clinician. For example, if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

The phrase "universal base" as used herein refers to its meaning as is generally accepted in the art. The term universal base generally refers to nucleotide base analogs that form base pairs with each of the natural DNA/RNA bases with little or no discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, for example, Loakes, 2001, *Nucleic Acids Research*, 29, 2437-2447).

The term "up-regulate" as used herein refers to its meaning as is generally accepted in the art. With reference nucleic acid molecules of the invention, the term refers to an increase in either the expression of a gene, or the level of RNA molecules or equivalent RNA molecules encoding one or more proteins or protein subunits, or the activity of one or more RNAs, proteins or protein subunits, above that observed in the absence of the nucleic acid molecules (e.g., siNA) of the invention. In certain instances, up-regulation or promotion of gene expression with an siNA molecule is above that level observed in the presence of an inactive or attenuated molecule. In other instances, up-regulation or promotion of gene expression with siNA molecules is above that level observed in the presence of, for example, an siNA molecule with scrambled sequence or with mismatches. In still other instances, up-regulation or promotion of gene expression with a nucleic acid molecule of the instant invention is greater in the presence of the nucleic acid molecule than in its absence. In some instances, up-regulation or promotion of gene expression is associated with inhibition of RNA mediated gene silencing, such as RNAi mediated cleavage or silencing of a coding or non-coding RNA target that down-regulates, inhibits, or silences the expression of the gene of interest to be up-regulated. The down-regulation of gene expression can, for example, be induced by a coding RNA or its encoded protein, such as through negative feedback or antagonistic effects. The down-regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down-regulation of targets that down-regulate, suppress, or silence a gene of interest can be used to up-regulate expression of the gene of interest toward therapeutic use.

The term "vector" as used herein refers to its meaning as is generally accepted in the art. The term vector generally refers to any nucleic acid- and/or viral-based expression system or technique used to deliver one or more nucleic acid molecules.

B. siNA Molecules

The instant invention features single- or double-stranded siNA molecules capable of mediating RNA interference comprising an antisense strand that is complementary to a nucleic acid target and comprises a 5' modified nucleotide with a 2' internucleoside linkage. The 5' modified nucleotide makes up position 1 at the 5' end of the antisense strand of the siNA molecules of the invention (i.e., the first nucleotide of the 5' end of the strand). The siNA molecules of the invention can take different oligonucleotide forms, including but not limited to short interfering RNA (siRNA), double-stranded RNA (dsRNA), micro-RNA (miRNA) and short hairpin RNA (shRNA) molecules.

In particular, short-interfering nucleic acid (siNA) molecules of the invention comprise an antisense strand having a 5' modified nucleotide at nucleotide position 1, wherein said 5' modified nucleotide is linked to a nucleotide at position 2 of the strand through a 2' internucleoside linkage and may contain a modified 5' cap (i.e., other than a 5' phosphate cap). In one embodiment, the short interfering nucleic acid (siNA) molecules of the invention comprise an antisense strand having a 5' modified nucleotide having the structure of Formula II:

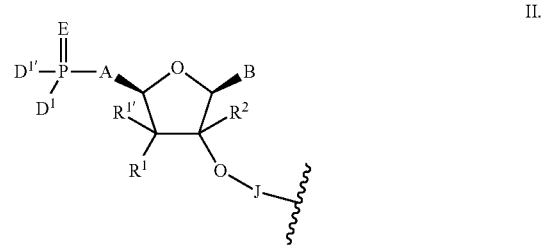

wherein:

A is —OC(R$^3$)$_2$—, —C(R$^3$)$_2$O—, —C(R$^3$)$_2$—, —C(R$^3$)$_2$C(R$^3$)$_2$— or —CR$^3$=CR$^3$—;

B is any heterocyclic base moiety;

D$^1$ and D$^{1'}$ are independently selected from hydroxyl, —OR$^4$, —SR$^4$, or —N(R$^4$)$_2$;

E is O, S, —NR$^5$, —N—N(R$^4$)$_2$ or —N—OR$^4$;

J is an internucleoside linking group linking the 5' modified nucleotide of Formula II to the sugar moiety of an adjacent nucleotide of the siNA molecule;

R$^1$ and R$^{1'}$ are independently selected from H, hydroxyl, halogen, C$_{1-6}$ alkyl, —OR$^6$, —N(R$^6$)$_2$, or together form =O or =CH$_2$;

R$^2$ is H, C$_{1-6}$ alkyl or C$_{2-6}$ alkenyl;

R$^3$ and R$^5$ are independently selected from H, hydroxyl, halogen, C$_{1-10}$ alkyl, C$_{2-6}$ alkenyl, C$_{2-6}$ alkynyl, aryl,

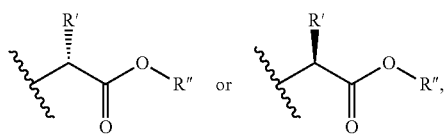 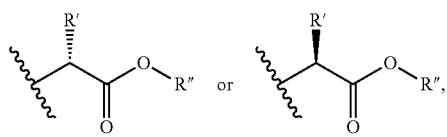

wherein R' is selected from H or $C_{1-4}$ alkyl (which is optionally substituted with one to three substituents independently selected from —$SR^{10}$, aryl, heteroaryl, amino, hydroxyl, oxo or —NH—C═(NH)$NH_2$, wherein the aryl and heteroaryl are optionally substituted with hydroxyl), and R" is selected from H, $C_{1-18}$ alkyl or aryl;

$R^4$ is independently selected from H, $C_{1-10}$ alkyl, $C_{2-6}$ alkenyl, $C_{2-6}$ alkynyl, aryl,

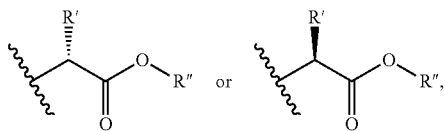

wherein R' is selected from H or $C_{1-4}$ alkyl (which is optionally substituted with one to three substituents independently selected from —$SR^{11}$, aryl, heteroaryl, amino, hydroxyl, oxo or —NH—C═(NH)$NH_2$, wherein the aryl and heteroaryl are optionally substituted with hydroxyl), and R" is selected from H, $C_{1-18}$ alkyl or aryl;

$R^6$ is independently selected from H, $C_{1-6}$ alkyl (which is optionally substituted with —OR, —$SR^7$, —$N(R^8)_2$, or (═O)—$NR^9$ or from one to three halogen), $C_{2-6}$ alkenyl, $C_{2-6}$ alkynyl, aryl,

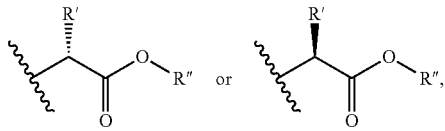

wherein R' is selected from H or $C_{1-4}$ alkyl (which is optionally substituted with one to three substituents independently selected from —$SR^{10}$, aryl, heteroaryl, amino, hydroxyl, oxo, —NH—C═(NH)$NH_2$, wherein the aryl and heteroaryl are optionally substituted with hydroxyl), and R" is selected from H, $C_{1-18}$ alkyl or aryl;

$R^7$ is methyl, —$CF_3$, —$N(R^8)_2$ or —$CH_2$—$N(R^8)_2$;

$R^8$ is independently selected from H or $C_{1-6}$ alkyl;

$R^9$ is $(R^8)_2$, —$R^8$—$(CH_2)_2$—$N(R^8)_2$ or —$R^8$—C(═$NR^8$)[$N(R^8)_2$]; and, $R^{10}$ is H or $C_{1-4}$ alkyl.

In certain embodiments, the siNA molecules of the invention are single-stranded molecules. In other embodiments, the siNA molecules of the invention are double-stranded molecules, wherein said double-stranded molecules comprises the antisense strand and a sense strand, wherein the sense strand is partially or completely complementary to the antisense strand.

In certain embodiments of the siNA molecules, $R^3$ of Formula II is independently selected from H, hydroxy, F, Cl, $C_{1-6}$ alkyl, $C_{2-6}$ alkenyl, $C_{2-6}$ alkynyl, aryl, wherein R' is selected from H, $C_{1-4}$ alkyl,

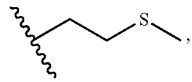

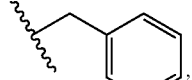

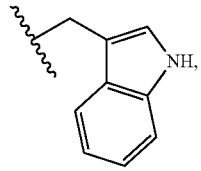

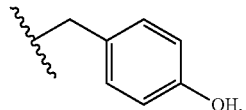

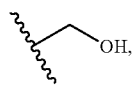

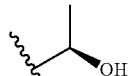

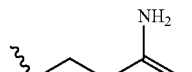

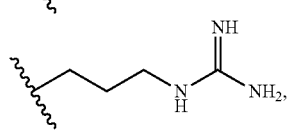

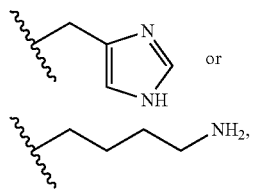

and R" is selected from H, $C_{1-4}$ alkyl or aryl.

In certain embodiments of the siNA molecules of the invention, A of Formula II is —$OCH_2$—, —$CH_2CH_2$— or —CH═CH—. In further embodiments, if A is —$OCH_2$—,

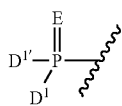

is not

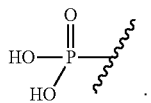

In further embodiments, A is —CH=CH—. In further embodiments, A is —CH=CH—, E is O, and $D^1$ and $D^{1'}$ are each hydroxyl.

In certain embodiments of the siNA molecules of the invention, B is uracil, thymine, cytosine, 5-methylcytosine, adenine or guanine. In further embodiments, B is thymine.

In certain embodiments of the siNA molecules of the invention, $D^1$ and $D^{1'}$ are independently selected from hydroxyl, —OCH$_3$ or —OCH$_2$CH$_3$. In certain embodiments, $D^1$ and $D^{1'}$ are independently hydroxyl. In certain embodiments, $D^1$ and $D^{1'}$ are independently —OCH$_3$. In certain embodiments, $D^1$ and $D^{1'}$ are independently —OCH$_2$CH$_3$.

In certain embodiments of the siNA molecules of the invention, E is O or S. In other embodiments, E is O.

In certain embodiments of the siNA molecules of the invention, J is a phosphodiester internucleoside linking group or a phosphorothioate internucleoside linking group.

In certain embodiments of the siNA molecules of the invention, $R^1$ is H or hydroxyl. In certain embodiments, $R^{1'}$ is H, hydroxyl, halogen or —OR$^6$. In certain embodiments, $R^{1'}$ is halogen, —OCH$_3$, —OCH$_2$F, —OCHF$_2$, —OCF$_3$, —OCH$_2$CH$_3$, —O(CH$_2$)$_2$F, —OCH$_2$CHF$_2$, —OCH$_2$CF$_3$, —OCH$_2$—CH=CH$_2$, —O(CH$_2$)$_2$—OCH$_3$, —O(CH$_2$)$_2$—SCH$_3$, —O(CH$_2$)$_2$—OCF$_3$, —OCH$_2$C(=O)—N(H)CH$_3$ or —OCH$_2$C(=O)—N(H)—(CH$_2$)$_2$—N(CH$_3$)$_2$. In certain embodiments, $R^{1'}$ is F or —OCH$_3$.

In certain embodiments, $R^2$ is H.

In certain embodiments, each of $R^1$, $R^{1'}$ and $R^2$ is H.

In certain embodiments of the siNA molecules of the invention, B is thymine and $R^1$, $R^{1'}$ and $R^2$ are each H.

In certain embodiments of the siNA molecules of the invention, the 5' modified nucleotide has is selected from:

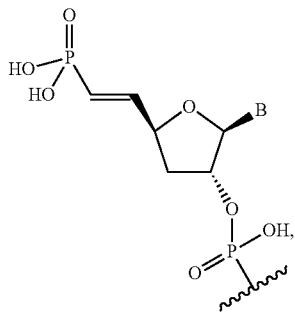

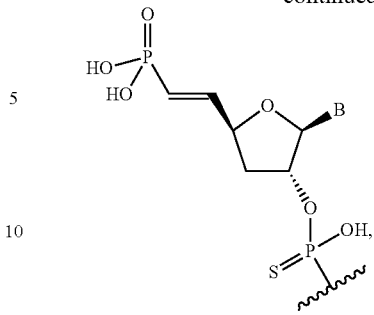

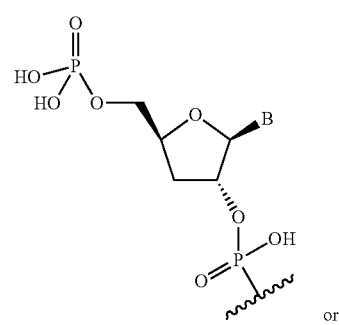

or

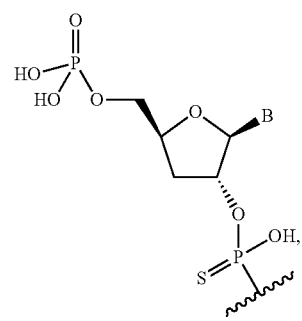

wherein B is uracil, thymine, cytosine, 5-methylcytosine, adenine or guanine. In further embodiments, B is thymine.

In certain embodiments of the siNA molecules of the invention, the 5' modified nucleotide is

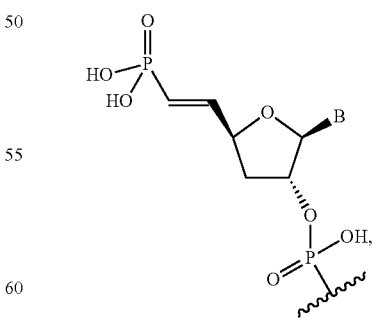

wherein B is uracil, thymine, cytosine, 5-methylcytosine, adenine or guanine. In further embodiments, B is thymine.

In certain embodiments of the siNA molecules of the invention, the 5' modified nucleotide is

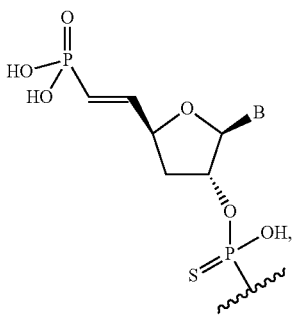

wherein B is uracil, thymine, cytosine, 5-methylcytosine, adenine or guanine. In further embodiments, B is thymine.

In certain embodiments of the siNA molecules of the invention, the 5' modified nucleotide is

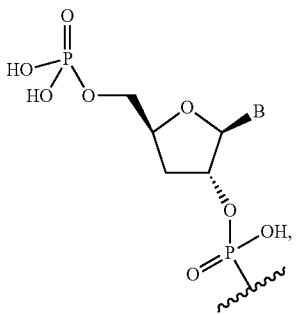

wherein B is uracil, thymine, cytosine, 5-methylcytosine, adenine or guanine. In further embodiments, B is thymine.

In certain embodiments of the siNA molecules of the invention, the 5' modified nucleotide is

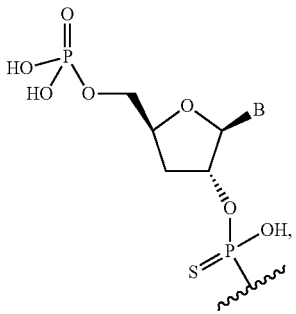

wherein B is uracil, thymine, cytosine, 5-methylcytosine, adenine or guanine. In further embodiments, B is thymine.

The siNA molecules of the invention can be single-stranded or double-stranded nucleic acid molecules. The nucleic acid molecules of the invention may modulate expression of a nucleic acid target in a cell or animal. In one embodiment, the siNA molecules of the invention inhibit or reduce expression of said nucleic acid target.

In one aspect, the invention provides single-stranded short interfering nucleic acid (siNA) molecules, wherein the single oligonucleotide strand comprises a sequence that is complementary to at least a part of a nucleic acid target sequence associated with gene expression. For purposes of this disclosure, the single strand of a single-stranded siNA molecule of the invention is referred to as the antisense strand.

In another aspect, the invention provides double-stranded short interfering nucleic acid (siNA) molecules, wherein a double-stranded siNA molecule comprises a sense and an antisense oligonucleotide strand. The antisense strand comprises a sequence that is complementary to at least a part of a nucleic acid target associated with gene expression, and the sense strand is complementary to the antisense strand. The double-stranded siNA molecules of the invention can comprise two distinct and separate strands that can be symmetric or asymmetric and are complementary, i.e., two single-stranded oligonucleotides, or can comprise one single-stranded oligonucleotide in which two complementary portions, e.g., a sense region and an antisense region (which, in this context, will be referred to herein as a sense strand and an antisense strand, respectively), are base-paired, and are covalently linked by one or more single-stranded "hairpin" areas (i.e. loops) resulting in, for example, a short-hairpin polynucleotide.

The linker can be polynucleotide linker or a non-nucleotide linker. In some embodiments, the linker is a non-nucleotide linker. In some embodiments, a hairpin siNA molecule of the invention contains one or more loop motifs, wherein at least one of the loop portions of the siNA molecule is biodegradable. For example, a short hairpin siNA molecule of the invention is designed such that degradation of the loop portion of the siNA molecule in vivo can generate a double-stranded siNA molecule with 3'-terminal overhangs, such as 3'-terminal nucleotide overhangs comprising 1, 2, 3 or 4 nucleotides.

The antisense strand of the siNA molecules of the invention is complementary to a portion of a target nucleic acid sequence. In some embodiments, the target nucleic acid is selected from a target mRNA, a target pre-mRNA, a target microRNA, and a target non-coding RNA. In certain embodiments, the antisense strand of the siNA molecules of the invention comprises a region that is 100% complementarity to a target nucleic acid sequence and wherein the region of 100% complementarity is at least 10 nucleobases. In certain embodiments, the region of 100% complementarity is at least 15 nucleobases. In certain embodiments, the region of 100% complementarity is at least 20 nucleobases. In certain embodiments, the region of 100% complementarity is at least 25 nucleobases. In certain embodiments, the region of 100% complementarity is at least 30 nucleobases. In certain embodiments, the antisense strand of the siNA molecules of the invention is at least 85% complementary to a target nucleic acid sequence. In certain embodiments, the antisense strand is at least 90% complementary to a target nucleic acid sequence. In certain embodiments, the antisense strand is at least 95% complementary to a target nucleic acid sequence. In certain embodiments, the antisense strand is at least 98% complementary to a target nucleic acid sequence. In certain embodiments, the antisense strand is 100% complementary to a target nucleic acid sequence. The complementary nucleotides may or may not be contiguous nucleotides. In one embodiment, the complementary nucleotides are contiguous nucleotides.

In certain embodiments, the siNA molecules of the invention have between about 15 to about 30 (e.g., about 15, 16, 17, 18, 19, 20, 21, 22, 23, 24, 25, 26, 27, 28, 29, or 30) nucleotides in the antisense strand that are complementary to a nucleotide sequence of a target nucleic acid molecule. In certain embodiments, the siNA molecules of the invention comprise an antisense strand having at least 15 nucleotides having sequence complementarity to a target sequence. In certain embodiments, the siNA molecules of the invention comprise an antisense strand having at least 18 nucleotides having sequence complementarity to a target sequence. In certain embodiments, the siNA molecules of the invention comprise an antisense strand having at least 19 nucleotides having sequence complementarity to a target sequence. In certain embodiments, the siNA molecules of the invention comprise an antisense strand having at least 20 nucleotides having sequence complementarity to a target sequence. In certain embodiments, the siNA molecules of the invention comprise an antisense strand having at least 21 nucleotides having sequence complementarity to a target sequence. In certain embodiments of this aspect of the invention, the complementary nucleotides are contiguous nucleotides.

In some embodiments, double-stranded siNA molecules of the invention have perfect complementarity between the sense strand or sense region and the antisense strand or antisense region of the siNA molecule, with the exception of any overhanging region.

In yet other embodiments, double-stranded siNA molecules of the invention have partial complementarity (i.e., less than 100% complementarity) between the sense strand or sense region and the antisense strand or antisense region of the siNA molecule. Thus, in some embodiments, the double-stranded nucleic acid molecules of the invention, have between about 15 to about 30 (e.g., about 15, 16, 17, 18, 19, 20, 21, 22, 23, 24, 25, 26, 27, 28, 29, or 30) nucleotides in one strand (e.g., sense strand) that are complementary to the nucleotides of the other strand (e.g., antisense strand). In certain embodiments, the double-stranded siNA molecules of the invention have 17 nucleotides in the sense region that are complementary to nucleotides of the antisense region of the nucleic acid molecule. In certain embodiments, the double-stranded siNA molecules of the invention have 18 nucleotides in the sense region that are complementary to nucleotides of the antisense region of the nucleic acid molecule. In certain embodiments, the double-stranded siNA molecules of the invention have 19 nucleotides in the sense region that are complementary to nucleotides of the antisense region of the nucleic acid molecule. In certain embodiments, the double-stranded siNA molecules of the invention have 20 nucleotides in the sense region that are complementary to nucleotides of the antisense region of the nucleic acid molecule. In certain embodiments of this aspect of the invention, the complementary nucleotides between the strands are contiguous nucleotides.

In symmetric siNA molecules of the invention, each strand, the sense (passenger) strand and antisense (guide) strand, are independently about 15 to about 30 (e.g., about 15, 16, 17, 18, 19, 20, 21, 22, 23, 24, 25, 26, 27, 28, 29, or 30) nucleotides in length. Generally, each strand of a symmetric siNA molecule of the invention is about 19-24 (e.g., about 19, 20, 21, 22, 23 or 24) nucleotides in length. In certain embodiments, each strand of a symmetric siNA molecule of the invention is 19 nucleotides in length. In certain embodiments, each strand of a symmetric siNA molecule of the invention is 20 nucleotides in length. In certain embodiments, each strand of a symmetric siNA molecule of the invention is 21 nucleotides in length. In certain embodiments, each strand of a symmetric siNA molecule of the invention is 22 nucleotides in length.

In asymmetric siNA molecules of the invention, the antisense strand of the molecule is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length. Generally, the antisense strand of an asymmetric siNA molecules of the invention is about 19-24 (e.g., about 19, 20, 21, 22, 23 or 24) nucleotides in length. In one embodiment, the sense strand of an asymmetric siNA molecule of the invention can be about 19-24 (e.g., about 19, 20, 21, 22, 23 or 24) nucleotides in length.

In yet other embodiments, siNA molecules of the invention comprise hairpin siNA molecules, wherein the siNA molecules are about 25 to about 70 (e.g., about 25, 26, 27, 28, 29, 30, 31, 32, 33, 34, 35, 36, 40, 45, 50, 55, 60, 65, or 70) nucleotides in length.

In certain embodiments, an siNA molecule of the invention is a microRNA mimetic, having a nucleotide sequence comprising a nucleotide portion that is fully or partially identical to a seed region of a microRNA. In certain embodiments, the nucleotide sequence of a microRNA mimetic has a nucleotide portion that is 100% identical to a seed region of a microRNA. In certain embodiments, the nucleotide sequence of a microRNA mimetic has a nucleotide portion that is at least 75% identical (e.g., about 75%, 80%, 85%, 90%, 95%, 96%, 97%, 98% or 99%) to a seed region of a microRNA. In certain embodiments, the nucleotide sequence of a microRNA mimetic has a nucleotide portion that is 75% identical to a seed region of a microRNA. In certain embodiments, the nucleotide sequence of a microRNA mimetic has a nucleotide portion that is 80% identical to a seed region of a microRNA. In certain embodiments, the nucleotide sequence of a microRNA mimetic has a nucleotide portion that is 90% identical to a seed region of a microRNA. In certain embodiments, the nucleotide sequence of a microRNA mimetic has a nucleotide portion that is 95% identical to a seed region of a microRNA.

In other embodiments, siNA molecules of the invention can contain one or more nucleotide deletions, substitutions, mismatches and/or additions (in reference to a target site sequence, or between strands of a duplex siNA molecule); provided, however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair. Thus, in some embodiments, for example, the double-stranded nucleic acid molecules of the invention, have one or more (e.g., 1, 2, 3, 4, 5, or 6) nucleotides in one strand or region (e.g., sense strand) that are mismatches or non-base-paired with the other strand or region (e.g., antisense strand). In certain embodiments, the siNA molecules of the invention contain no more than 3 mismatches. If the antisense strand of an siNA molecule contains mismatches to a target sequence, it is preferable that the area of mismatch is not located in the center of a contiguous region of complementarity.

In certain embodiments, the siNA molecules of the invention comprise overhangs of about 1 to about 4 (e.g., about 1, 2, 3 or 4) nucleotides. The nucleotides in the overhangs can be the same or different nucleotides. In some embodiments, the overhangs occur at the 3'-end (or the 3' terminus) of one or both strands of double-stranded nucleic acid molecules of the invention. For example, a double-stranded nucleic acid molecule of the invention can comprise a nucleotide or non-nucleotide overhang at the 3'-end of the antisense strand/region, at the 3'-end of the sense strand/region, or at the 3' ends of both the antisense strand/region and the sense strand/region. Overhanging nucleotides can be modified or unmodified.

In some embodiments, the nucleotides comprising the overhanging portion of an siNA molecule of the invention comprise sequences based on an target nucleic acid sequence in which the nucleotides comprising the overhanging portion of the antisense strand/region are complementary to nucleotides in the target polynucleotide sequence and/or the nucleotides comprising the overhanging portion of the sense strand/region comprise nucleotides from the target polynucleotide sequence. Thus, in some embodiments, the overhang comprises a two nucleotide overhang that is complementary to a portion of the target polynucleotide sequence. In other embodiments, however, the overhang comprises a two nucleotide overhang that is not complementary to a portion of the target nucleic acid sequence. In certain embodiments, the overhang comprises a 3'-UU overhang that is not complementary to a portion of the target nucleic acid sequence. In other embodiments, the overhang comprises a UU overhang at the 3' end of the antisense strand and a TT overhang at the 3' end of the sense strand.

In any of the embodiments of the siNA molecules described herein having 3'-end nucleotide overhangs, the overhangs are optionally chemically modified at one or more nucleic acid sugar, base, or backbone positions. Representative, but not limiting examples of modified nucleotides in the overhanging portion of a double-stranded siNA molecule of the invention include: 2'-O-alkyl (e.g., 2'-O-methyl), 2'-deoxy, 2'-deoxy-2'-fluoro, 2'-deoxy-2'-fluoroarabino (FANA), 4'-thio, 2'-O-trifluoromethyl, 2'-O-ethyl-trifluoromethoxy, 2'-O-difluoromethoxy-ethoxy, universal base, acyclic, or 5-C-methyl nucleotides. In more preferred embodiments, the overhang nucleotides are each independently, a 2'-O-alkyl nucleotide, a 2'-O-methyl nucleotide, a 2'-deoxy-2-fluoro nucleotide, or a 2'-deoxy ribonucleotide. In some instances the overhanging nucleotides are linked by one or more phosphorothioate linkages.

In yet other embodiments, siNA molecules of the invention comprise duplex nucleic acid molecules with blunt ends (i.e., without nucleotide overhangs), where both termini of the molecule are blunt, or alternatively, where one of the ends is blunt. In some embodiments, the siNA molecules of the invention comprise one blunt end, for example wherein the 5'-end of the antisense strand and the 3'-end of the sense strand do not have any overhanging nucleotides, or wherein the 3'-end of the antisense strand and the 5'-end of the sense strand do not have any overhanging nucleotides. In other embodiments, siNA molecules of the invention comprise two blunt ends, for example wherein the 3'-end of the antisense strand and the 5'-end of the sense strand, as well as the 5'-end of the antisense strand and 3'-end of the sense strand, do not have any overhanging nucleotides.

In any of the embodiments or aspects of the siNA molecules of the invention, the sense strand and/or the antisense strand can further have a cap, such as described herein or as known in the art. A cap can be present at the 3'-end of the antisense strand, the 5'-end of the sense strand, and/or the 3'-end of the sense strand. In the case of a hairpin siNA molecule, a cap can be present at the 3'-end of the polynucleotide. The cap at the 5'-end of the antisense strand of an siNA of the invention is encompassed by the 5' modified nucleotide as set forth by the structure of Formula I and II. In some embodiments, a cap is at one or both ends of the sense strand of a double-stranded siNA molecule. In other embodiments, a cap is at the 3'-end of antisense (guide) strand. In other embodiments, a cap is at the 3'-end of the sense strand and at the 5'-end of the sense strand. Representative but non-limiting examples of such terminal caps include an inverted abasic nucleotide and derivatives thereof (e.g., an inverted deoxy abasic nucleotide, a tetra-N-acethylgalactosamine aminohexyl phosphate inverted abasic nucleotide (e.g., tetraGalNAcLys-6amiL-iB-omeC; see Table 14, infra), an inverted nucleotide moiety, a glyceryl modification, an alkyl or cycloalkyl group, a heterocycle or any other cap as is generally known in the art.

Any of the embodiments of the siNA molecules of the invention can have a 5' phosphate terminus. In some embodiments, the siNA molecules lack terminal phosphates.

In certain embodiments, the double-stranded siNA molecules of the invention comprise about 3 to about 30 (e.g., about 3, 4, 5, 6, 7, 8, 9, 10, 11, 12, 13, 14, 15, 16, 17, 18, 19, 20, 21, 22, 23, 24, 25, 26, 27, 28, 29, or 30) base pairs. Generally, the duplex structure of siNAs of the invention is between 15 and 30 base pairs, more generally between 18 and 25 base pairs, yet more generally between 19 and 24 base pairs, and most generally between 19 and 21 base pairs in length. In one embodiment, a double-stranded siNA molecule of the invention comprises 19 base pairs. In one embodiment, a double-stranded siNA molecule of the invention comprises 20 base pairs. In one embodiment, a double-stranded siNA molecule of the invention comprises 21 base pairs. The double-stranded siNA molecules of this portion of the invention can be asymmetric or symmetric. In other embodiments of this aspect of the invention, the siNA duplex molecules are hairpin structures.

Any siNA molecule of the invention can comprise one or more chemically-modified nucleotides in addition to the 5' modified nucleotide of the antisense strand, as described in detail supra. Modifications can be used to improve in vitro or in vivo characteristics such as stability, activity, toxicity, immune response (e.g., prevent stimulation of an interferon response, an inflammatory or pro-inflammatory cytokine response, or a Toll-like Receptor response), and/or bioavailability. Various chemically modified siNA motifs disclosed herein have the potential to maintain an RNAi activity that is substantially similar to either unmodified or minimally-modified active siRNA (see for example Elbashir et al., 2001, *EMBO J.*, 20:6877-6888) while, at the same time, providing nuclease resistance and pharmacokinetic properties suitable for use in therapeutic applications.

In certain embodiments of the siNA molecules of the invention, wherein such siNA molecules comprise a 5' modified nucleotide having the structure of Formula II, any (e.g., one, more or all) additional nucleotides present in the antisense and/or sense strand may be modified nucleotides (e.g., wherein one additional nucleotide is modified, some additional nucleotides (i.e., a plurality or more than one) are modified, or all nucleotides of the molecule are modified nucleotides). Modifications include sugar modifications, base modifications, backbone (internucleoside linkage) modifications, non-nucleotide modifications, and/or any combination thereof. In certain embodiments, the siNA molecules of the invention further comprise one or more additional 2' internucleoside linkages (e.g., one or more additional 2'-5' internucleoside linkages).

Non-limiting examples of chemical modifications that are suitable for use in the siNA molecules of the invention are disclosed in U.S. Pat. No. 8,202,979 and U.S. patent application Ser. Nos. 10/981,966 and 12/064,014 (published as US 20050266422 and US 20090176725, respectively), and in references cited therein, and include sugar, base, and backbone modifications, non-nucleotide modifications, and/or any combination thereof. These U.S. Patents and Applications are incorporated hereby as references for the purpose of describing chemical modifications that are suitable for use with the siNA molecules of the invention.

The chemical modifications of nucleotides present within a single siNA molecule can be the same or different. In some embodiments, at least one strand of an siNA molecule of the invention has at least one chemical modification. In other embodiments, each strand has at least one chemical modification, which can be the same or different, such as sugar, base, or backbone (i.e., internucleotide linkage) modifications. In other embodiments, siNA molecules of the invention contain at least 2, 3, 4, 5, or more different chemical modifications.

In some embodiments, the siNA molecules of the invention are partially modified (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, or 59 nucleotides are modified) with chemical modifications. In some embodiments, an siNA molecule of the invention comprises at least about 8, 10, 12, 14, 16, 18, 20, 22, 24, 26, 28, 30, 32, 34, 36, 38, 40, 42, 44, 46, 48, 50, 52, 54, 56, 58, or 60 nucleotides that are modified nucleotides, excluding the 5' modified nucleotide of the antisense strand. In other embodiments, the siNA molecules of the invention are completely modified (100% modified) with chemical modifications, i.e., the siNA molecule does not contain any ribonucleotides. In some of embodiments, one or more of the nucleotides in the sense strand of the siNA molecules of the invention are modified. In the same or other embodiments, one or more of the nucleotides in the antisense strand of the siNA molecules of the invention are modified, excluding the 5' modified nucleotide of the antisense strand. In some embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of the nucleotide positions independently in either one or both strands of an siNA molecule of the invention are modified, excluding the 5' modified nucleotide of the antisense strand.

Modified nucleotides contained within the siNA molecules of the present invention include those with modifications at the 2'-carbon of a sugar moiety and/or the 3'-carbon of a sugar moiety of a nucleotide. In certain specific embodiments of the invention, at least one modified nucleotide is a 2'-deoxy-2-fluoro nucleotide, a 2'-deoxy nucleotide, a 2'-O-alkyl (e.g., 2'-O-methyl) nucleotide, a 2'-methoxyethoxy or a locked nucleic acid (LNA) nucleotide, as is generally recognized in the art.

In yet other embodiment of the invention, at least one nucleotide has a ribo-like, Northern or A form helix configuration (see e.g., Saenger, Principles of Nucleic Acid Structure, Springer-Verlag ed., 1984). Non-limiting examples of nucleotides having a Northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl nucleotides; 2'-deoxy-2'-fluoro nucleotides; 2'-deoxy-2'-chloro nucleotides; 2'-azido nucleotides; 2'-O-trifluoromethyl nucleotides; 2'-O-ethyl-trifluoromethoxy nucleotides; 2'-O-difluoromethoxy-ethoxy nucleotides; 4'-thio nucleotides; and 2'-O-methyl nucleotides. In various embodiments, a majority (e.g., greater than 50%) of the pyrimidine nucleotides present in a double-stranded siNA molecule comprises a sugar modification. In some of the same and/or other embodiments, a majority (e.g., greater than 50%) of the purine nucleotides present in a double-stranded siNA molecule comprises a sugar modification.

In certain instances, purine and pyrimidine nucleotides of the siNA molecules of the invention are differentially modified. In one example, purine and pyrimidine nucleotides can be differentially modified at the 2'-carbon of the sugar moiety (i.e., at least one purine has a different modification from at least one pyrimidine in the same or different strand at the 2'-carbon of the sugar moiety). In certain embodiments, the purines are unmodified in one or both strands, while the pyrimidines in one or both strands are modified. In certain other instances, the pyrimidines are unmodified in one or both strands, while the purines in one or both strands are modified. In certain instances, wherein the siNA molecules comprise one or more modifications as described herein, the nucleotides at positions 2 and 3 at the 5' end of the antisense (guide) strand are unmodified.

In some embodiments of the siNA molecules of the invention, the pyrimidine nucleotides in the antisense strand are 2'-O-methyl or 2'-deoxy-2'-fluoro pyrimidine nucleotides, and the purine nucleotides present in the antisense strand are 2'-O-methyl nucleotides or 2'-deoxy nucleotides. In certain embodiments, all of the pyrimidine nucleotides in a complementary region of an antisense strand of an siNA molecule of the invention are 2'-deoxy-2'-fluoro pyrimidine nucleotides. In certain embodiments, all of the purines in the complementary region on the antisense strand are 2'-O-methyl purine nucleotides.

In other embodiments of the siNA molecules of the invention, the pyrimidine nucleotides in the sense strand are 2'-deoxy-2'-fluoro pyrimidine nucleotides, and the purine nucleotides present in the sense strand are 2'-O-methyl or 2'-deoxy purine nucleotides. In certain embodiments of the invention, all the pyrimidine nucleotides in the complementary region on the sense strand are 2'-deoxy-2'-fluoro pyrimidine nucleotides. In certain embodiments, all the purine nucleotides in the complementary region on the sense strand are 2'-deoxy purine nucleotides.

In certain embodiments, all of the pyrimidine nucleotides in the complementary regions on the sense strand are 2'-deoxy-2'-fluoro pyrimidine nucleotides; all of the pyrimidine nucleotides in the complementary region of the antisense strand are 2'-deoxy-2'-fluoro pyrimidine nucleotides; all the purine nucleotides in the complementary region on the sense strand are 2'-deoxy purine nucleotides and all of the purines in the complementary region on the antisense strand are 2'-O-methyl purine nucleotides.

In some embodiments, at least 5 or more of the pyrimidine nucleotides in one or both strands of an siNA molecule of the invention are 2'-deoxy-2'-fluoro pyrimidine nucleotides. In some embodiments, at least 5 or more of the pyrimidine nucleotides in one or both strands are 2'-O-methyl pyrimidine nucleotides. In some embodiments, at least 5 or more of the purine nucleotides in one or both strands are 2'-deoxy-2'-fluoro purine nucleotides In some embodiments, at least 5 or more of the purine nucleotides in one or both strands are 2'-O-methyl purine nucleotides.

In certain embodiments, the siNA molecules of the invention comprise one or more modified internucleoside linking group (i.e., other than the 2' internucleoside linkage as set forth in the 5' modified nucleotide of Formula II). A modified internucleoside linking group is a linking group other than a phosphodiester 3'-5' internucleoside linking group, including but not limited to 2' internucleoside linking groups (e.g., phosphodiester and phosphorothioate 2'-5' internucleoside linkages). In certain embodiments, each internucleoside linking group is, independently, a 2' or 3' phosphodiester or phosphorothioate internucleoside linking group. In certain embodiments, the 5'-most internucleoside linking group on either or both strands of an siNA molecule of the invention is a phosphorothioate linking group. In certain embodiments, the siNA molecules of the invention comprise from 3 to 12 contiguous phosphorothioate linking groups, wherein the phosphorothioate linking groups are either 2' or 3' internucleoside linking groups. In certain embodiments, the siNA molecules of the invention comprise from 6 to 8 contiguous phosphorothioate linking groups, wherein the phosphorothioate linking groups are either 2' or 3' internucleoside linking groups. In certain embodiments, the 3' end of the antisense and/or sense strand of the siNA molecules of the invention comprises a phosphorothioate linking groups. In certain embodiments, the siNA molecules of the invention comprise from 6 to 8 contiguous phosphorothioate linking groups at the 3' end of the antisense and/or sense strand, wherein the phosphorothioate linking groups are either 2' or 3' internucleoside linking groups.

In certain embodiments, an siNA molecule of the invention does not contain any additional chemically-modified nucleotides with a 2'-5' internucleoside linkage (i.e., only the 5' modified nucleotide at position 1 of the antisense strand of an siNA molecule of the invention has a 2' internucleoside linkage, as described by the 5' modified nucleotide of Formula II). In further embodiments, any one or more additional chemically-modified nucleotides in the antisense strand and/or, optionally, the sense strand of either a single- or double-stranded siNA molecule of the invention does not have a 2'-5' internucleoside linkage. In one embodiment of the siNA molecules of the invention, the nucleotide at position two of the antisense strand does not contain a 2'-5' internucleoside linkage. In another embodiment, the nucleotide at position three of the antisense strand does not contain a 2'-5' internucleoside linkage. In a further embodiment, neither nucleotide at position two nor position 3 contain a 2'-5' internucleoside linkage.

In one embodiment, the siNA molecules of the invention, comprising an antisense strand having a 5' modified nucleotide of the structure of Formula II, comprise one or more additional nucleotides that are linked to an adjacent (consecutive) nucleotide through a 2' internucleoside linkage. In particular, in certain embodiments, the siNA molecules of the invention further comprise one or more additional nucleotides having the structure of Formula III:

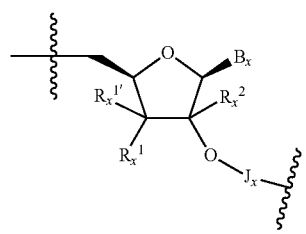

III wherein:
$B_x$ is any heterocyclic base moiety;
$J_x$ is an internucleoside linking group linking the nucleotide of Formula III to the sugar moiety of the adjacent (consecutive) nucleotide of the siNA molecule;
$R_x^1$ and $R_x^{1'}$ are independently selected from H, hydroxyl, halogen, $C_{1-6}$ alkyl, $-OR_x^3$, $-N(R_x^3)_2$, or together form $=O$ or $=CH_2$;
$R_x^2$ is H, $C_{1-6}$ alkyl or $C_{2-6}$ alkenyl;
$R_x^3$ is independently selected from H, $C_{1-6}$ alkyl (which is optionally substituted with $-OR_x^4$, $-SR_x^4$, $-N(R_x^5)_2$, (=O)$-NR_x^6$ or from one to three halogen), $C_{2-6}$ alkenyl, $C_{2-6}$ alkynyl, aryl,

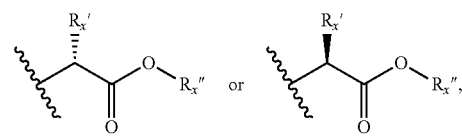

wherein $R_x'$ is selected from H or $C_{1-4}$ alkyl (which is optionally substituted with one to three substituents independently selected from $-SR_x^7$, aryl, heteroaryl, amino, hydroxyl, oxo, $-NH-C=(NH)NH_2$, wherein the aryl and heteroaryl are optionally substituted with hydroxyl), and $R_x''$ is selected from H, $C_{1-18}$ alkyl or aryl;
$R_x^4$ is methyl, $-CF_3$, $-N(R_x^5)_2$ or $-CH_2-N(R_x^5)_2$;
$R_x^5$ is independently selected from H or $C_{1-6}$ alkyl;
$R_x^6$ is $(R_x^5)_2$, $-R_x^5-(CH_2)_2-N(R_x^5)_2$ or $-R_x^5-C(=NR_x^5)[N(R_x^5)_2]$; and,
$R_x^7$ is H or $C_{1-4}$ alkyl.

In certain embodiments of this aspect of the invention, $B_x$ is uracil, thymine, cytosine, 5-methylcytosine, adenine or guanine.

In certain embodiments of this aspect of the invention, $J_x$ is a phosphodiester internucleoside linking group or a phosphorothioate internucleoside linking group.

In certain embodiments of this aspect of the invention, $R_x^1$ is H. In certain embodiments of this aspect of the invention, $R_x^{1'}$ is H, halogen or $-OR_x^3$. In other embodiments of this aspect of the invention, $R_x^{1'}$ is halogen, $-OCH_3$, $-OCH_2F$, $-OCHF_2$, $-OCF_3$, $-OCH_2CH_3$, $-O(CH_2)_2F$, $-OCH_2CHF_2$, $-OCH_2CF_3$, $-OCH_2-CH=CH_2$, $-O(CH_2)_2-OCH_3$, $-O(CH_2)_2-SCH_3$, $-O(CH_2)_2-OCF_3$, $-OCH_2C(=O)-N(H)CH_3$ or $-OCH_2C(=O)-N(H)-(CH_2)_2-N(CH_3)_2$. In other embodiments of this aspect of the invention, $R_x^{1'}$ is H, F, hydroxyl or $-OCH_3$.

In certain embodiments, the antisense strand of a single- or double-stranded siNA molecule of the invention may contain up to 9 (e.g., 0, 1, 2, 3, 4, 5, 6, 7, 8 or 9) additional chemically-modified nucleotides with 2'-5' internucleoside linkages, including but not limited to a nucleotide of Formula III. In a further embodiment, the antisense strand of a single- or double-stranded siNA molecule of the invention may contain up to 5 (e.g., 0, 1, 2, 3, 4 or 5) additional chemically-modified nucleotides with 2'-5' internucleoside linkages. In a further embodiment, the antisense strand of a single- or double-stranded siNA molecule of the invention may contain up to 3 (e.g., 0, 1, 2 or 3) additional chemically-modified nucleotides with 2'-5' internucleoside linkages. In another embodiment, the antisense strand of a single- or double-stranded siNA molecule of the invention may contain one additional chemically-modified nucleotide with a 2'-5' internucleoside linkage.

Any of the above described modifications, or combinations thereof, including those in the references cited, can be applied to any of the siNA molecules of the invention.

C. 5' Modified Nucleotides

The instant invention features 5' modified nucleotides that, when incorporated into an siNA molecule of the invention, are located at nucleotide position 1 at the 5' end of the antisense strand of the molecule, are linked to a nucleotide at position 2 of the antisense strand through a 2' internucleoside linkage, and may contain a modified 5' cap (i.e., other than a 5' phosphate cap). These 5' modified nucleotides can be used as reagents to generate the siNA molecules of the invention.

In particular, the instant invention features 5' modified nucleotides having the structure of Formula I:

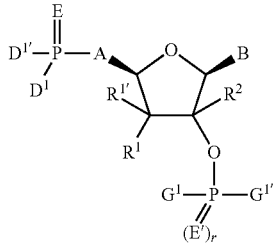

wherein:
A is —C(R$^3$)$_2$—, —C(R$^3$)$_2$C(R$^3$)$_2$— or —CR$^3$=CR$^3$—;
B is any heterocyclic base moiety;
D$^1$ and D$^{1'}$ are independently selected from hydroxyl, —OR$^4$, —SR$^4$, or —N(R$^4$)$_2$;
E and E' are independently selected from O, S, —NR$^5$, —N—N(R$^4$)$_2$ or —N—OR$^4$;
G$^1$ is hydroxyl or —OR$^6$;
G$^{1'}$ is hydroxyl, —OR$^6$ or —N(R$^6$)$_2$;
R$^1$ and R$^{1'}$ are independently selected from H, hydroxyl, halogen, C$_{1-6}$ alkyl, —OR$^7$, —N(R$^7$)$_2$, or together form =O or =CH$_2$;
R$^2$ is H, C$_{1-6}$ alkyl or C$_{2-6}$ alkenyl;
R$_3$ and R$_5$ are independently selected from H, hydroxyl, halogen, C$_{1-10}$ alkyl, C$_{2-6}$ alkenyl, C$_{2-6}$ alkynyl, aryl,

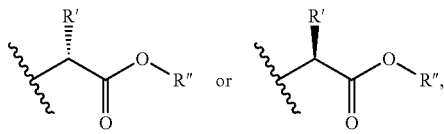

wherein R' is selected from H or C$_{1-4}$ alkyl (which is optionally substituted with one to three substituents independently selected from —SR$^{11}$, aryl, heteroaryl, amino, hydroxyl, oxo or —NH—C=(NH)NH$_2$, wherein the aryl and heteroaryl are optionally substituted with hydroxyl), and R" is selected from H, C$_{1-18}$ alkyl or aryl;
R$^4$ is independently selected from H, C$_{1-10}$ alkyl, C$_{2-6}$ alkenyl, C$_{2-6}$ alkynyl, aryl,

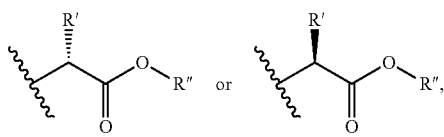

wherein R' is selected from H or C$_{1-4}$ alkyl (which is optionally substituted with one to three substituents independently selected from —SR$^{11}$, aryl, heteroaryl, amino, hydroxyl, oxo or —NH—C=(NH)NH$_2$, wherein the aryl and heteroaryl are optionally substituted with hydroxyl), and R" is selected from H, C$_{1-18}$ alkyl or aryl;
R$^6$ is independently C$_{1-6}$ alkyl, optionally substituted on the terminal carbon atom with cyano or a protecting group;
R$^7$ is independently selected from H, C$_{1-6}$ alkyl (which is optionally substituted with —OR$^8$, —SR$^8$, —N(R$^9$)$_2$, (=O)—NR$^{10}$ or from one to three halogen), C$_{2-6}$ alkenyl, C$_{2-6}$ alkynyl, aryl,

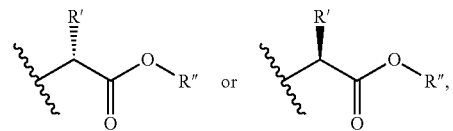

wherein R' is selected from H or C$_{1-4}$ alkyl (which is optionally substituted with one to three substituents independently selected from —SR$^{11}$, aryl, heteroaryl, amino, hydroxyl, oxo, —NH—C=(NH)NH$_2$, wherein the aryl and heteroaryl are optionally substituted with hydroxyl), and R" is selected from H, C$_{1-18}$ alkyl or aryl;
R$^8$ is methyl, —CF$_3$, —N(R$^9$)$_2$ or —CH$_2$—N(R$^9$)$_2$;
R$^9$ is independently selected from H or C$_{1-6}$ alkyl;
R$^{10}$ is (R$^9$)$_2$, —R$^9$—(CH$_2$)$_2$—N(R$^9$)$_2$ or —R$^9$—C(=NR$^9$)[N(R$^9$)$_2$];
R$^{11}$ is H or C$_{1-4}$ alkyl; and,
r is 0 or 1.

In certain embodiments, R$^3$ is independently selected from H, hydroxy, F, Cl, C$_{1-6}$ alkyl, C$_{2-6}$ alkenyl, C$_{2-6}$ alkynyl, aryl,

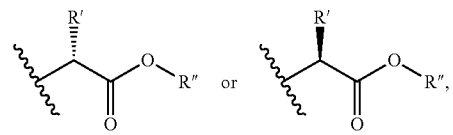

wherein R' is selected from H, C$_{1-4}$ alkyl (e.g., methyl, isopropyl, isobutyl, sec-butyl),

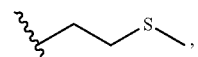

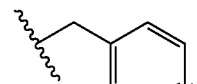

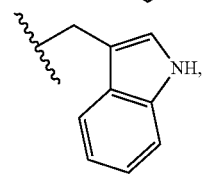

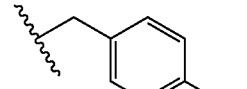

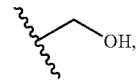

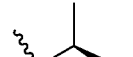

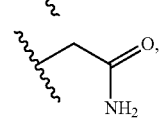

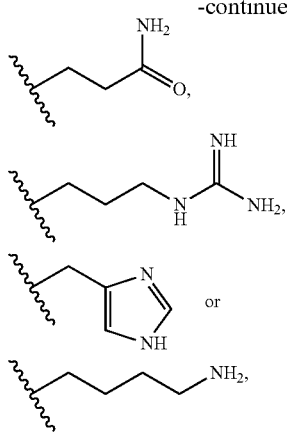

and R" is selected from H, $C_{1-4}$ alkyl (e.g., methyl, ethyl, n-propyl, isopropyl) or aryl.

In certain embodiments, A is —$CH_2CH_2$— or —CH=CH—. In certain embodiments, A is CH=CH—.

In certain embodiments, B is selected from uracil, thymine, cytosine, 5-methylcytosine, adenine or guanine. In certain embodiments, B is thymine.

In certain embodiments, $D^1$ and $D^{1'}$ is independently selected from hydroxyl, —$OCH_3$ or —$OCH_2CH_3$. In certain embodiments, $D^1$ and $D^{1'}$ is independently —$OCH_2CH_3$.

In certain embodiments, E is selected from O or S. In certain embodiments, E is O.

In certain embodiments, r is 1. In certain of these embodiments, where r is 1, $G^1$ and $G^{1'}$ are hydroxyl, and E' is O or S.

In certain embodiments, r is 0. In certain of these embodiments, wherein r is 0, $G^1$ is —$O(CH_2)_2CN$ and $G^{1'}$ is —$N[CH(CH_3)_2]_2$.

In certain embodiments, $R^1$ is H.

In certain embodiments, $R^{1'}$ is H, halogen or —$OR^7$. In certain embodiments, $R^{1'}$ is halogen, —$OCH_3$, —$OCH_2F$, —$OCHF_2$, —$OCF_3$, —$OCH_2CH_3$, —$O(CH_2)_2F$, —$OCH_2CHF_2$, —$OCH_2CF_3$, —$OCH_2$—CH=$CH_2$, —$O(CH_2)_2$—$OCH_3$, —$O(CH_2)_2$—$SCH_3$, —$O(CH_2)_2$—$OCF_3$, —$OCH_2C(=O)$—$N(H)CH_3$ or —$OCH_2C(=O)$—$N(H)$—$(CH_2)_2$—$N(CH_3)_2$. In certain embodiments, $R^{1'}$ is F or —$OCH_3$.

In certain embodiments, $R^2$ is H.

In certain embodiments, each of $R^1$, $R^{1'}$ and $R^2$ is H.

D. Generation/Synthesis of siNA Molecules

The siNA molecules of the invention can be obtained using a number of techniques known to those of skill in the art. For example the siNA molecules can be chemically synthesized using protocols known in the art (for example, as described in: Caruthers et al., 1992, *Methods in Enzymology* 211, 3-19; Thompson et al., International PCT Publication No. WO 99/54459; Wincott et al., 1995, *Nucleic Acids Res.* 23, 2677-2684; Wincott et al., 1997, *Methods Mol. Bio.*, 74, 59; Brennan et al., 1998, *Biotechnol Bioeng.*, 61, 33-45; Brennan, U.S. Pat. No. 6,001,311; Usman et al., 1987, *J. Am. Chem. Soc.*, 109, 7845; and Scaringe et al., 1990, *Nucleic Acids Res.*, 18, 5433). The syntheses of oligonucleotides described in the art makes use of common nucleic acid protecting and coupling groups, such as dimethoxytrityl at the 5'-end and phosphoramidites at the 3'- or 2'-end. These syntheses can also be used for certain siNA molecules of the invention.

In certain embodiments, the siNA molecules of the invention are synthesized, deprotected, and analyzed according to methods described in, for example, U.S. Pat. Nos. 6,995,259, 6,686,463, 6,673,918, 6,649,751, 6,989,442, and 7,205,399.

In a non-limiting synthesis example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides.

Alternatively, the siNA molecules of the present invention can be synthesized separately and joined together post-synthetically, for example, by ligation (e.g., Moore et al., 1992, *Science* 256, 9923; Draper et al., International PCT Publication No. WO 93/23569; Shabarova et al., 1991, *Nucleic Acids Research* 19, 4247; Bellon et al., 1997, *Nucleosides & Nucleotides,* 16, 951; and Bellon et al., 1997, *Bioconjugate Chem.* 8, 204), or by hybridization following synthesis and/or deprotection.

E. Carrier/Delivery Systems

The siNA molecules of the invention are added directly to target cells or tissues or complexed with various components (e.g., packaged within liposomes; coupled with single chemical entity targeting moieties) for delivery to target cells or tissues. Methods for the delivery of nucleic acid molecules are described in, for example, Akhtar et al., 1992, *Trends Cell Bio.,* 2, 139; *Delivery Strategies for Antisense Oligonucleotide Therapeutics*, ed Akhtar, 1995; Maurer et al., 1999, *Mol. Membr. Biol.,* 16, 129-140; Hofland and Huang, 1999, *Handb. Exp. Pharmacol.,* 137, 165-192; and Lee et al., 2000, *ACS Symp. Ser.,* 752, 184-192. Beigelman et al., U.S. Pat. No. 6,395,713, and Sullivan et al., PCT International application publication no. WO 94/02595, further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example, Gonzalez et al., 1999, *Bioconjugate Chem.,* 10, 1068-1074; Wang et al., International PCT Publication Nos. WO 03/47518 and WO 03/46185), poly(lactic-co-glycolic)acid (PLGA) and PLCA microspheres (see, e.g., U.S. Pat. No. 6,447,796 and US Patent Application Publication No. US 2002130430), biodegradable nanocapsules, and bioadhesive microspheres, or by proteinaceous vectors (e.g., O'Hare and Normand, International PCT Publication No. WO 00/53722).

In one aspect, the present invention provides carrier systems containing the siNA molecules described herein. In some embodiments, the carrier system is a lipid-based carrier system, cationic lipid, or liposome nucleic acid complexes, a liposome, a micelle, a virosome, a lipid nanoparticle or a mixture thereof. In other embodiments, the carrier system is a polymer-based carrier system such as a cationic polymer-nucleic acid complex. In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. In another embodiment, the carrier system is a lipid nanoparticle ("LNP") formulation.

In certain embodiments, the siNA molecules of the invention are formulated with a lipid nanoparticle composition such as is described in U.S. Pat. No. 7,514,099 and U.S. Pat. No. 7,404,969, U.S. patent application Ser. Nos. 13/059,491, 13/390,702, 13/699,451, 13/701,636 and 13/500,733, and PCT International Patent Appl. publication nos. WO 2010/080724, WO 2011/090965, WO 2010/021865, WO 2010/042877, WO 2010/105209, WO 2011/127255, WO 2012/040184, WO 2012/044638 and WO 2011/022460.

In other embodiments, the invention features conjugates and/or complexes of siNA molecules of the invention. Such conjugates and/or complexes can be used to facilitate delivery of siNA molecules into a biological system, such as a cell. The conjugates and complexes provided by the instant invention have the potential of imparting therapeutic activity by transferring therapeutic compounds across cellular membranes, altering the pharmacokinetics, and/or modulating the localization of nucleic acid molecules of the invention. Non-limiting, examples of such conjugates are described in U.S. Pat. Nos. 8,137,695, 7,833,992, 6,528,631, 6,335,434, 6,235,886, 6,153,737, 5,214,136, 5,138,045 and 7,816,337, and U.S. patent application Ser. No. 10/201,394 (e.g., CDM-LBA, CDM-Pip-LBA, CDM-PEG, CDM-NAG, etc.).

In various embodiments, polyethylene glycol (PEG) can be covalently attached to siNA compounds of the present invention. The attached PEG can be any molecular weight, preferably from about 100 to about 50,000 daltons (Da).

In yet other embodiments, the invention features compositions or formulations comprising surface-modified liposomes containing poly (ethylene glycol) lipids (PEG-modified, or long-circulating liposomes or stealth liposomes) and siNA molecules of the invention, such as is disclosed in for example, International PCT Publication Nos. WO 96/10391, WO 96/10390 and WO 96/10392.

In some embodiments, the siNA molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules of the invention are formulated as described in U.S. Patent Application publication no. 2003/0077829.

In other embodiments, siNA molecules of the invention are complexed with membrane disruptive agents such as those described in U.S. Pat. No. 6,835,393. In still other embodiments, the membrane disruptive agent or agents and the siNA molecule are also complexed with a cationic lipid or helper lipid molecule, such as those lipids described in U.S. Pat. No. 6,235,310.

In certain embodiments, siNA molecules of the invention are complexed with delivery systems as described in U.S. Patent Application publication nos. 2003/0077829; 2005/0287551; 2005/0191627; 2005/0118594; 2005/0153919; 2005/0085486; and 2003/0158133; and International PCT publication nos. WO 00/03683 and WO 02/087541.

In some embodiments, a liposomal formulation of the invention comprises an siNA molecule of the invention (e.g., siNA) formulated or complexed with compounds and compositions described in U.S. Pat. Nos. 6,858,224, 6,534,484, 6,287,591, 6,835,395, 6,586,410, 6,858,225, 6,815,432, 6,586,001, 6,120,798, 6,977,223, 6,998,115, 5,981,501, 5,976,567, 5,705,385; and U.S. Patent Application publication nos. 2006/0019912, 2006/0019258, 2006/0008909, 2005/0255153, 2005/0079212, 2005/0008689, 2003/0077829, 2005/0064595, 2005/0175682, 2005/0118253, 2004/0071654, 2005/0244504, 2005/0265961 and 2003/0077829.

F. Kits

The present invention also provides nucleic acids in kit form. The kit may comprise a container. The kit typically contains a nucleic acid of the invention with instructions for its administration. In certain instances, the nucleic acids may have a targeting moiety attached. Methods of attaching targeting moieties (e.g. antibodies, proteins) are known to those of skill in the art. In certain instances, the nucleic acids are chemically modified. In other embodiments, the kit contains more than one siNA molecule of the invention. The kits may comprise an siNA molecule of the invention with a pharmaceutically acceptable carrier or diluent. The kits may further comprise excipients.

G. Uses siNA molecules of the present invention are useful to modulate (e g, inhibit) the expression of a target nucleic acid by an RNAi interference mechanism. Thus, one aspect of the present invention relates to methods of inhibiting gene expression by target-specific RNA interference in a cell comprising contact said cell with an siNA molecule, or a composition thereof, or the invention. The methods of inhibiting gene expression of the invention may occur in vitro or in vivo. In certain embodiments, the cell is an animal cell (e.g., a mammalian cell). In certain embodiments, the cell is a mammalian cell. In further embodiments, the mammalian cell is inside the animal.

The siNA molecules of the invention may be useful to regulate the expression and/or activity of a target nucleic acid (i.e., a target gene) and, thus, have the potential of being used in assays for diagnostic purposes and/or in therapeutic regimens to treat one or more disease states. For example, the one or more disease states having the potential of being diagnosed and/or treated with an siNA of the invention may be associated with the expression of a particular gene target to which the siNA is directed. Thus, in this example, the siNA molecules of the invention have the potential to degrade a target-related mRNA, the gene expression of which is associated with a particular disease state.

In one embodiment, inhibition of a disease may be evaluated by directly measuring the progress of the disease in a subject. For example, it may also be inferred through observing a change or reversal in a condition associated with the disease. siNA molecules of the invention also have the potential of being used as a prophylaxis. Thus, use of the siNA molecules and pharmaceutical compositions of the invention have the potential of ameliorating, treating, preventing, and/or curing diseases states associated with regulation of gene expression of a particular target.

One aspect of the invention comprises a method of decreasing the expression of a gene in a subject suffering from a condition or disease which is mediated by the action, or by loss of action, of said target gene, which method comprises administering to said subject an effective amount of an siNA molecule of the invention. In one embodiment, the siNA molecule is directed to the gene (i.e., the target gene). In another embodiment, the siNA molecule is directed to a target within the expression and/or activity pathway of gene (i.e., a pathway target gene). In one embodiment, the subject is a human subject.

In one embodiment, a subject to which an siNA molecule of the invention, or composition thereof, may be administered is suffering from cancer or a condition associated with cancer. Thus, the siNA molecules of the present invention have the potential of being useful to treat cancer, including but not limited to the potential modulation of the metastases of cancer cells and/or conditions associated with cancer. Examples of cancers that have the potential of being treated according to this aspect of the invention may include bladder cancer, bladder transitional cell carcinoma, urothelial carcinoma, brain cancer, gliomas, astrocytomas, breast cancer, breast carcinoma, cervical cancer, colorectal cancer, rectal cancer, colorectal carcinoma, colon cancer, hereditary non-polyposis colorectal cancer, endometrial carcinoma, esophageal cancer, esophageal squamous cell carcinoma, ocular melanoma, uveal melanoma, intraocular melanoma, primary intraocular lymphoma, renal cell carcinoma, clear cell renal cell carcinoma, papillary renal cell carcinoma, leukemia, acute lymocytic leukemia (ALL), acute myeloid leukemia (AML), chronic myeloid (CML), chronic myelomonocytic (CMML), liver cancer, hepatoma, hepatocellular carcinoma, cholangiocarcinoma, lung cancer, small cell lung cancer (SCLC), non-small cell lung cancer (NSCLC), Non-Hodgkin lymphoma, B-cell lymphomas, T-cell lymphomas, precursor T-lymphoblastic lymphoma/leukemia, multiple myeloma, ovarian carcinoma, pancreatic cancer, pancreatic ductal adenocarcinoma, prostate cancer, prostate adenocarcinoma, rhabdomyosarcoma, embryonal rhabdomyosarcoma, skin cancer, melanoma, malignant melanoma, cutaneous melanoma, mucosal melanoma, small intestine carcinomas, stomach cancer, gastric carcinoma, testicular cancer, testicular seminomas, testicular non-seminomas, thyroid cancer, papillary thyroid carcinoma, and papillary adenocarcinomas.

siNA molecules of the invention have the potential of being useful as reagents in ex vivo applications. For example, siNA molecules may be introduced into tissue or cells that are transplanted into a subject for a potential therapeutic effect. The cells and/or tissue can be derived from an organism or subject that later receives the explant, or can be derived from another organism or subject prior to transplantation. In this context, the siNA molecules may modulate the expression of one or more genes in the cells or tissue, such that the cells or tissue obtain a desired phenotype or are able to perform a function when transplanted in vivo.

H. Pharmaceutical Compositions

The siNA molecules of the instant invention have the potential of providing useful reagents for use in methods related to a variety of therapeutic, prophylactic, veterinary, diagnostic, target validation, genomic discovery, genetic engineering, and pharmacogenomic applications.

1. Formulations

The present invention provides for pharmaceutical compositions of the siNA molecules described, i.e., compositions in a pharmaceutically acceptable carrier or diluent. These formulations or compositions can comprise a pharmaceutically acceptable carrier or diluent as is generally known in the art.

The siNA molecules of the invention are preferably formulated as pharmaceutical compositions prior to administering to a subject, according to techniques known in the art. Pharmaceutical compositions of the present invention are characterized as being at least sterile and pyrogen-free. Methods for preparing pharmaceutical compositions of the invention are within the skill in the art for example as described in *Remington's Pharmaceutical Science*, 17th ed., Mack Publishing Company, Easton, Pa. (1985).

In some embodiments, pharmaceutical compositions of the invention (e.g., siNA and/or LNP formulations thereof) further comprise conventional pharmaceutical excipients and/or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, e.g., DTPA or DTPA-bisamide) or calcium chelate complexes (e.g. calcium DTPA, CaNaDTPA-bisamide), or, optionally, additions of calcium or sodium salts (e.g., calcium chloride, calcium ascorbate, calcium gluconate or calcium lactate). In addition, antioxidants and suspending agents can be used.

Non-limiting examples of various types of formulations for local administration include ointments, lotions, creams, gels, foams, preparations for delivery by transdermal patches, powders, sprays, aerosols, capsules or cartridges for use in an inhaler or insufflator or drops (e.g., eye or nose drops), solutions/suspensions for nebulization, suppositories, pessaries, retention enemas and chewable or suckable tablets or pellets (e.g., for the treatment of aphthous ulcers) or liposome or microencapsulation preparations.

Ointments, creams and gels, can, for example, can be formulated with an aqueous or oily base with the addition of suitable thickening and/or gelling agent and/or solvents. Non-limiting examples of such bases can thus, e.g., include water and/or an oil (such as liquid paraffin) or a vegetable oil (such as arachis oil or castor oil), or a solvent (such as polyethylene glycol). Various thickening agents and gelling agents can be used depending on the nature of the base. Non-limiting examples of such agents include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

In one embodiment, lotions can be formulated with an aqueous or oily base and will in general also contain one or more emulsifying agents, stabilizing agents, dispersing agents, suspending agents or thickening agents.

In one embodiment, powders for external application can be formed with the aid of any suitable powder base, e.g., talc, lactose or starch. Drops can be formulated with an aqueous or non-aqueous base also comprising one or more dispersing agents, solubilizing agents, suspending agents or preservatives.

Compositions intended for oral use can be prepared according to any method known to the art for the manufacture of pharmaceutical compositions, and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, e.g., inert diluents (such as calcium carbonate, sodium carbonate, lactose, calcium phosphate or sodium phosphate), granulating and disintegrating agents (e.g., corn starch, or alginic acid), binding agents (e.g., starch, gelatin or acacia), and lubricating agents (e.g., magnesium stearate, stearic acid or talc). The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, e.g., calcium carbonate, calcium phosphate or kaolin, or as soft gelatin capsules wherein the active ingredient is mixed with water or an oil medium, e.g., peanut oil, liquid paraffin or olive oil.

Aqueous suspensions contain the active materials in a mixture with excipients suitable for the manufacture of aqueous suspensions. Such excipients are suspending agents, e.g., sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, e.g., lecithin, or condensation products of an alkylene oxide with fatty acids, e.g., polyoxyethylene stearate; or condensation products of ethylene oxide with long chain aliphatic alcohols, e.g., heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, e.g., polyethylene sorbitan monooleate. The aqueous suspensions can also contain one or more preservatives, e.g. ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, e.g. arachis oil, olive oil, sesame oil or coconut oil, or in a mineral oil such as liquid paraffin. The oily suspensions can contain a thickening agent, e.g. beeswax, hard paraffin or cetyl alcohol. Sweetening agents and flavoring agents can be added to provide palatable oral preparations. These compositions can be preserved by the addition of an anti-oxidant such as ascorbic acid Pharmaceutical compositions of the invention can also be in the form of oil-in-water emulsions. The oily phase can be a vegetable oil or a mineral oil or mixtures of these. Suitable emulsifying agents can be naturally-occurring gums, e.g. gum acacia or gum tragacanth, naturally-occurring phosphatides, e.g. soy bean, lecithin, and esters or partial esters derived from fatty acids and hexitol, anhydrides, for example sorbitan monooleate, and condensation products of the said partial esters with ethylene oxide, e.g. polyoxyethylene sorbitan monooleate. The emulsions can also contain sweetening and flavoring agents.

Syrups and elixirs can be formulated with sweetening agents, e.g. glycerol, propylene glycol, sorbitol, glucose or sucrose. Such formulations can also contain a demulcent, a preservative, and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The siNA molecules of the invention can take the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

siNA molecules of the invention can be formulated in a sterile medium for parenteral administration. The molecule, depending on the vehicle and concentration used, can either be suspended or dissolved in the vehicle. Advantageously, adjuvants such as local anesthetics, preservatives and buffering agents can be dissolved in the vehicle.

In other embodiments, siNA molecule formulations provided herein for use in pulmonary delivery further comprise one or more surfactants. Suitable surfactants or surfactant components for enhancing the uptake of the compositions of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, and/or choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

In one embodiment, the siNA molecules of the invention can be formulated for administration via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the siNA compositions of the invention can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Spray compositions comprising siNA molecules of the invention can, for example, be formulated as aqueous solutions or suspensions or as aerosols delivered from pressurized packs, such as a metered dose inhaler, with the use of a suitable liquefied propellant. In one embodiment, aerosol compositions of the invention suitable for inhalation can be either a suspension or a solution and generally contain an siNA molecule of the invention and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition can optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment, a pharmaceutical aerosol formulation of the invention comprising a compound of the invention and a fluorocarbon or hydrogen-containing chlorofluorocarbon or mixtures thereof as propellant, optionally in combination with a surfactant and/or a co-solvent.

The aerosol formulations of the invention can be buffered by the addition of suitable buffering agents.

Aerosol formulations can include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions of the invention (e.g., siNA and/or LNP formulations thereof). In another embodiment, a device comprising a nebulizer delivers a composition of the invention (e.g., siNA and/or LNP formulations thereof) comprising fluorochemicals that are bacteriostatic thereby decreasing the potential for microbial growth in compatible devices.

Capsules and cartridges comprising the composition of the invention for use in an inhaler or insufflator, of for example gelatin, can be formulated containing a powder mix for inhalation of a compound of the invention and a suitable powder base such as lactose or starch. In one embodiment, each capsule or cartridge contains an siNA molecule of the invention and one or more excipients. In another embodiment, the compound of the invention can be presented without excipients such as lactose.

The siNA molecules can also be formulated as a fluid formulation for delivery from a fluid dispenser, such as those described and illustrated in WO05/044354.

2. Combinations

The siNA molecules and pharmaceutical formulations according to the invention can be administered to a subject alone or used in combination with one or more other therapies, including known therapeutic agents, treatments, or procedures to prevent or treat diseases, disorders, conditions, and traits. A person of ordinary skill in the art would be able to discern which combinations of therapeutic agents would be useful based on the particular characteristics of the drug components and the disease indication/state involved, including but not limited cancer.

A combination can conveniently be presented for use in the form of a pharmaceutical composition, wherein the pharmaceutical composition comprises a combination that includes an siNA molecule of the invention, a pharmaceutically acceptable diluent or carrier, and one or more additional therapeutic agents. Alternatively, the individual components of such combinations can be administered either sequentially or simultaneously in separate or combined pharmaceutical formulations.

I. Administration

Compositions or formulations may be administered in a variety of ways. In certain embodiments, the administration of an siNA molecule is via local administration or systemic administration, either alone as a monotherapy or in combination with additional therapies described herein or as are known in the art.

Local administration can include, for example, inhalation, nebulization, catheterization, implantation, direct injection, dermal/transdermal application, patches, stenting, ear/eye drops, or portal vein administration to relevant tissues, or any other local administration technique, method or procedure, as is generally known in the art. Systemic administration can include, for example, pulmonary (inhalation, nebulization etc.) intravenous, subcutaneous, intramuscular, catheterization, nasopharyngeal, transdermal, or oral/gastrointestinal administration as is generally known in the art. Further non-limiting examples of administration methods of the invention include buccal, sublingual, parenteral (i.e., intraarticularly, intravenously, intraperitoneally, subcutaneously, or intramuscularly), local rectal administration or other local administration. In one embodiment, the composition of the invention can be administered by insufflation and inhalation.

In one embodiment, the siNA molecules of the invention and formulations or compositions thereof are administered to the liver via methods generally known in the art (see, e.g., Wen et al., 2004, *World J Gastroenterol.*, 10, 244-9; Murao et al., 2002, *Pharm Res.*, 19, 1808-14; Liu et al., 2003, *gene Ther.*, 10, 180-7; Hong et al., 2003, *J Pharm Pharmacol.*, 54, 51-8; Herrmann et al., 2004, *Arch Virol.*, 149, 1611-7; and Matsuno et al., 2003, *gene Ther.*, 10, 1559-66).

In one embodiment, the invention features the use of methods to deliver the siNA molecules of the instant invention and compositions thereof to hematopoietic cells, including monocytes and lymphocytes. These methods are described in detail by Hartmann et al., 1998, *J. Pharmacol. Exp. Ther.*, 285(2), 920-928; Kronenwett et al., 1998, *Blood*, 91(3), 852-862; Filion and Phillips, 1997, *Biochim. Biophys. Acta.*, 1329(2), 345-356; Ma and Wei, 1996, *Leuk. Res.*, 20(11/12), 925-930; and Bongartz et al., 1994, *Nucleic Acids Research*, 22(22), 4681-8.

In one embodiment, the siNA molecules of the invention and formulations or compositions thereof are administered directly or topically (e.g., locally) to the dermis or follicles via methods generally known in the art (see, e.g., Brand, 2001, *Curr. Opin. Mol. Ther.*, 3, 244-8; Regnier et al., 1998, *J. Drug Target*, 5, 275-89; Kanikkannan, 2002, *BioDrugs*, 16, 339-47; Wraight et al., 2001, *Pharmacol. Ther.*, 90, 89-104; and Preat and Dujardin, 2001, STP PharmaSciences, 11, 57-68). In one embodiment, the siNA molecules of the invention and formulations or compositions thereof are administered directly or topically using a hydroalcoholic gel formulation comprising an alcohol (e.g., ethanol or isopropanol), water, and optionally including additional agents such isopropyl myristate and carbomer 980. In other embodiments, the siNA molecules and compositions are administered topically to the nasal cavity. Topical preparations can be administered by one or more applications per day to the affected area. Continuous or prolonged delivery can be achieved by an adhesive reservoir system.

In one embodiment, an siNA molecule of the invention or a composition thereof is administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In some embodiments, the pharmaceutical compositions are administered intravenously or intraperitoneally by a bolus injection (see, e.g., U.S. Pat. No. 5,286,634). Lipid nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71(1994)).

For therapeutic applications, a pharmaceutically effective dose of the siNA molecules or pharmaceutical compositions of the invention is administered to the subject. A pharmaceutically effective dose is that dose required to prevent, inhibit the occurrence, or treat (alleviate a symptom to some extent, preferably all of the symptoms) a disease state. One skilled in the art can readily determine a therapeutically effective dose of an siNA molecule of the invention to be administered to a given subject, e.g., by taking into account factors, such as the size and weight of the subject, the extent of the disease progression or penetration, the age, health, and sex of the subject, the route of administration, and whether the administration is regional or systemic. Generally, an amount between 0.1 μg/kg and 100 mg/kg body weight/day of active ingredients is administered dependent upon potency of the negatively charged polymer. Optimal dosing schedules can be calculated from measurements of drug accumulation in the body of the patient. The siNA molecules of the invention can be administered in a single dose or in multiple doses.

siNA molecules of the instant invention can be administered once monthly, once weekly, once daily (QD), or divided into multiple monthly, weekly, or daily doses, such as, for example, twice daily (BID), three times daily (TID), once every two weeks. Thus, administration can be accomplished via single or divided doses. Persons of ordinary skill in the art can easily estimate repetition rates for dosing based on measured residence times and concentrations of the drug in bodily fluids or tissues.

In addition, the administration can be continuous, e.g., every day, or intermittently. For example, intermittent administration of an siNA molecule of the instant invention may be administration one to six days per week, administration in cycles (e.g., daily administration for two to eight consecutive weeks, then a rest period with no administration for up to one week), or administration on alternate days.

The compositions of the present invention, either alone or in combination with other suitable components, can be made into aerosol formulations (i.e., they can be "nebulized") to be administered via inhalation (e.g., intranasally or intratracheally) (see, Brigham et al., Am. J. Sci., 298:278 (1989)). Aerosol formulations can be placed into pressurized acceptable propellants, such as dichlorodifluoromethane, propane, nitrogen, and the like.

The aerosol compositions of the present invention can be administered into the respiratory system as a formulation that includes particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range can be from 1 to 5 microns. In another embodiment, the particulate range can be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

In some embodiments, an siNA composition of the invention is administered topically to the nose for example, for the treatment of rhinitis, via pressurized aerosol formulations, aqueous formulations administered to the nose by pressurized pump or by nebulization.

Solid particle aerosols comprising an siNA molecule or formulation of the invention and surfactant can be produced with any solid particulate aerosol generator. One type of solid particle aerosol generator used with the siNA molecules of the invention is an insufflator. A second type of illustrative aerosol generator comprises a metered dose inhaler ("MDI"). MDIs containing siNA molecules or formulations taught herein can be prepared by methods of the art (for example, see Byron, above and WO96/32099).

Thus, in certain embodiments of the invention, nebulizer devices are used in applications for conscious, spontaneously breathing subjects, and for controlled ventilated subjects of all ages. The nebulizer devices can be used for targeted topical and systemic drug delivery to the lung. In one embodiment, a device comprising a nebulizer is used to deliver an siNA molecule or formulation of the invention locally to lung or pulmonary tissues. In another embodiment, a device comprising a nebulizer is used to deliver an siNA molecule or formulation of the invention systemically.

J. Other Applications/Uses of siNA Molecules of the Invention

The siNA molecules of the invention can also be used for diagnostic applications, research applications, and/or manufacture of medicaments.

In one aspect, the invention features a method for diagnosing a disease, trait, or condition in a subject comprising administering to the subject a composition of the invention under conditions suitable for the diagnosis of the disease, trait, or condition in the subject.

In another embodiment, the invention comprises use of a double-stranded nucleic acid according to the invention for use in the manufacture of a medicament. In an embodiment, the medicament is for use in treating a condition that is mediated by the action, or by loss of action, of a gene or protein.

EXAMPLES

Examples provided are intended to assist in a further understanding of the invention. Particular materials employed, species and conditions are intended to be illustrative of the invention and not limiting of the reasonable scope thereof. Certain starting materials and reagents are either commercially available or known in the chemical scientific or patent literature.

The abbreviations used herein have the following tabulated meanings (see Table 1). Abbreviations not tabulated below have their meanings as commonly used unless specifically stated otherwise.

TABLE 1

| Abbreviations | |
|---|---|
| TBDMSC1 | t-butyldimethylchlorosilane |
| DMTrCl | 4,4'-dimethyloxytrityl chloride |
| DCM | dichloromethane |
| DMAP | 4-dimethylaminopyridine |
| EtOAc | ethylacetate |
| $Na_2SO_4$ | sodium sulfate |
| AIBN | azobisisobutyronitrile |
| $SnH(Bu)_3$ | tri-n-butyltin hydride |
| DCAA | dichloroacetic acid |
| $MgSO_4$ | magnesium sulfate |
| TFA | trifluoroacetic acid |
| DMSO | dimethyl sulfoxide |
| DCC | N,N'-dicyclohexylcarbodiimide |
| THF | tetrahydrofuran |
| KOtBu | potassium t-butoxide |
| $NH_4Cl$ | ammonium chloride |
| ACN or MeCN | acetonitrile |
| DIPEA | N,N'-diisopropylethylamine |
| $NaHCO_3$ | sodium bicarbonate |
| NaOH | sodium hydroxide |
| TBSCl | tert-butylchlorodimethylsilane |
| TBAF | tetrabutylammoniumfluoride |
| $Et_3N$ | triethylamine |

General Schemes

Scheme 1

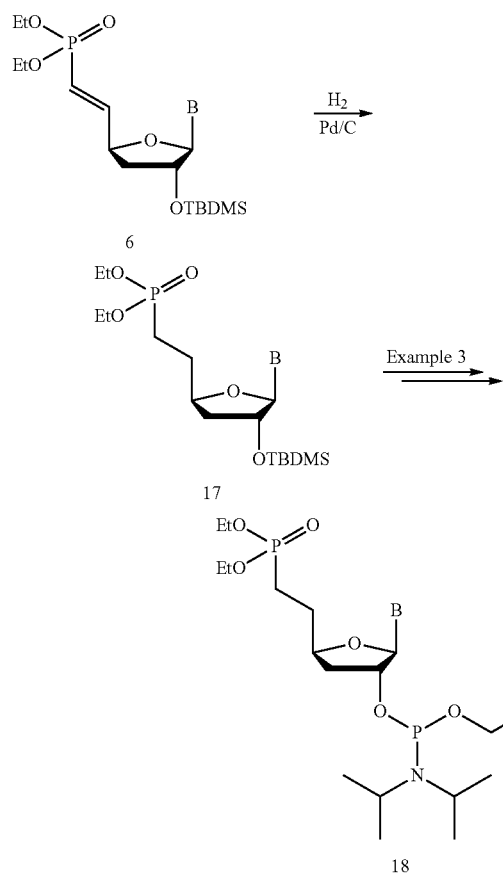

Generic Scheme 1 can be used to generate 5' modified nucleotides of Formula I, wherein A is —C(R$^3$)$_2$C(R$^3$)$_2$— and R$^3$ is H. B can be any heterocyclic base moiety (e.g., uracil, thymine, cytosine, 5-methylcytosine, guanine etc.). These phosphoramidites can be used to make siNA molecules of the invention.

Scheme 2

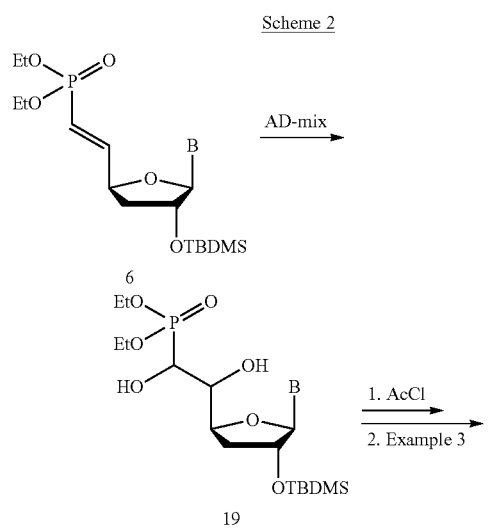

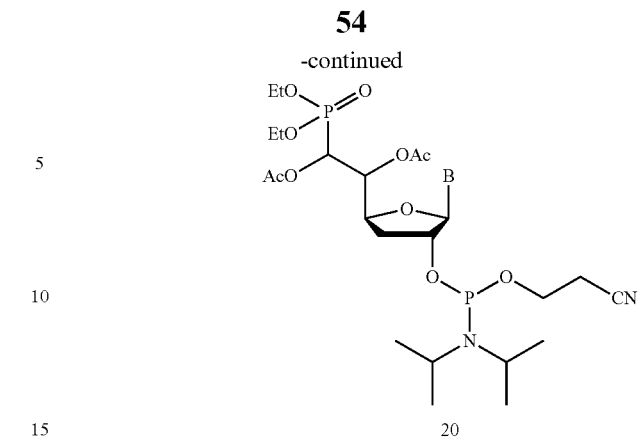

Generic Scheme 2 can be used to generate 5' modified nucleotides of Formula I, wherein A is —C(R$^3$)$_2$C(R$^3$)$_2$— and R$^3$ is OAc. B can be any heterocyclic base moiety (e.g., uracil, thymine, cytosine, 5-methylcytosine, guanine etc.). These phosphoramidites can be used to make siNA molecules of the invention.

Scheme 3

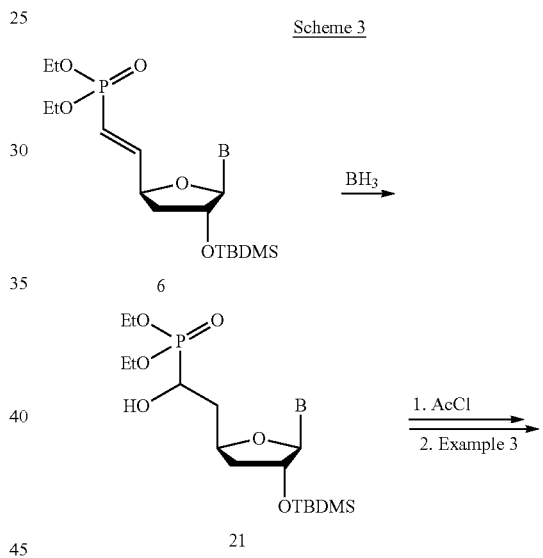

Generic Scheme 3 can be used to generate 5' modified nucleotides of Formula I, wherein A is —C(R$^3$)$_2$C(R$^3$)$_2$— and R$^3$ is OAc or H. B can be any heterocyclic base moiety (e.g., uracil, thymine, cytosine, 5-methylcytosine, guanine etc.). These phosphoramidites can be used to make siNA molecules of the invention.

Scheme 4
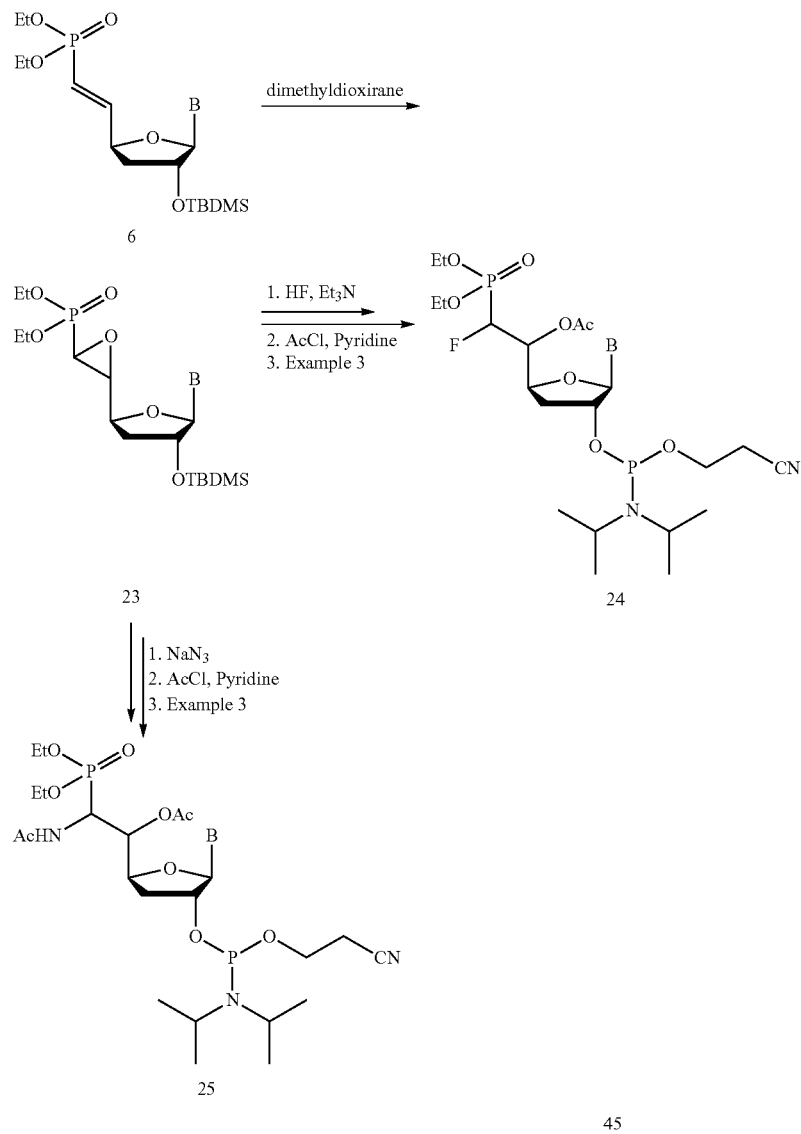
Generic Scheme 4 can be used to generate 5' modified nucleotides of Formula I, wherein A is —C($R^3$)$_2$C($R^3$)$_2$— and $R^3$ is —OAc, —NHAc or F. B can be any heterocyclic base moiety (e.g., uracil, thymine, cytosine, 5-methylcytosine, guanine etc.). These phosphoramidites can be used to make siNA molecules of the invention.
Scheme 5
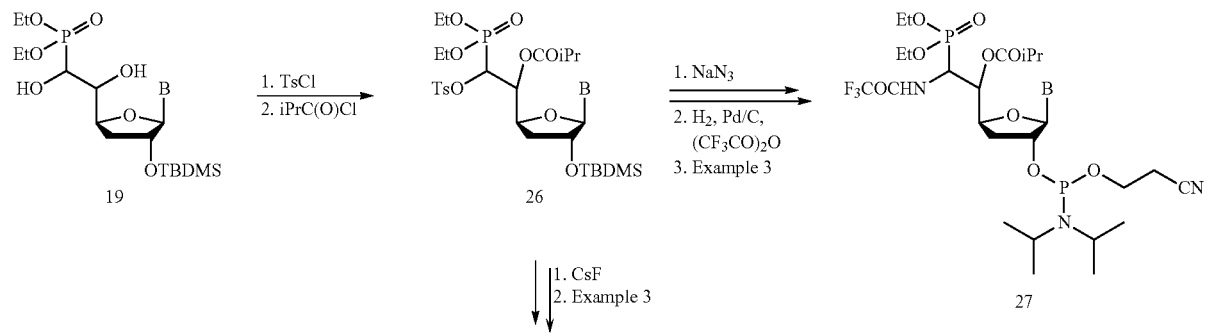

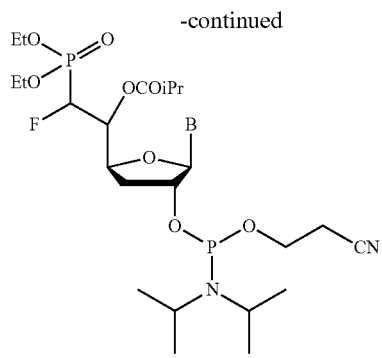

28

Generic Scheme 5 can be used to generate 5' modified nucleotides of Formula I, wherein A is —C(R³)₂C(R³)₂— and R³ is —OC(O)iPr, —NHC(O)CF₃ or F. B can be any heterocyclic base moiety (e.g., uracil, thymine, cytosine, 5-methylcytosine, guanine etc.). These phosphoramidites can be used to make siNA molecules of the invention.

Scheme 6

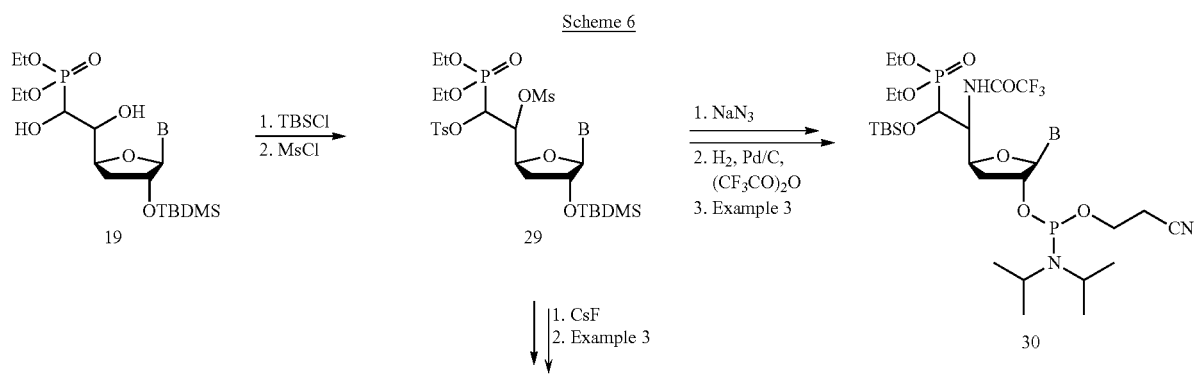

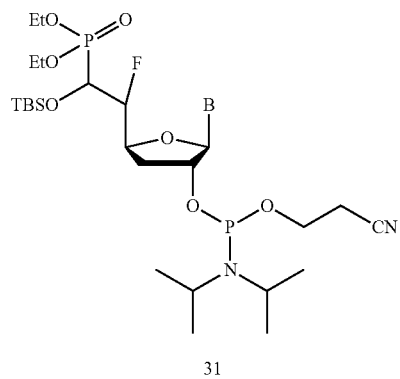

31

Generic Scheme 6 can be used to generate 5' modified nucleotides of Formula I, wherein A is —C(R³)₂C(R³)₂— and R³ is —OTBS, —NHC(O)CF₃ or F. B can be any heterocyclic base moiety (e.g., uracil, thymine, cytosine, 5-methylcytosine, guanine etc.). These phosphoramidites can be used to make siNA molecules of the invention.

Scheme 7
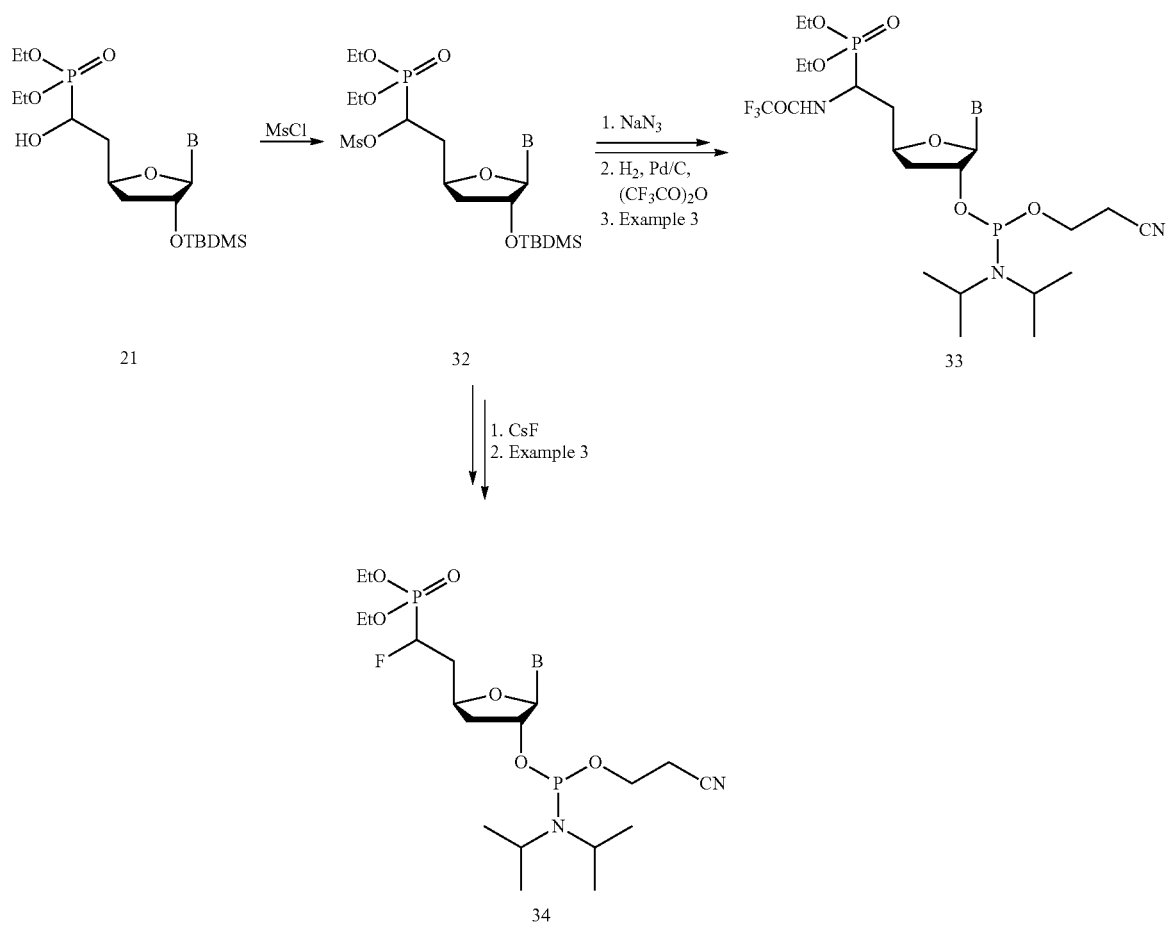
Generic Scheme 7 can be used to generate 5' modified nucleotides of Formula I, wherein A is —C(R$^3$)$_2$C(R$^3$)$_2$— and R$^3$ is NHC(O)CF$_3$ or F. B can be any heterocyclic base moiety (e.g., uracil, thymine, cytosine, 5-methylcytosine, guanine etc.). These phosphoramidites can be used to make siNA molecules of the invention.
Scheme 8
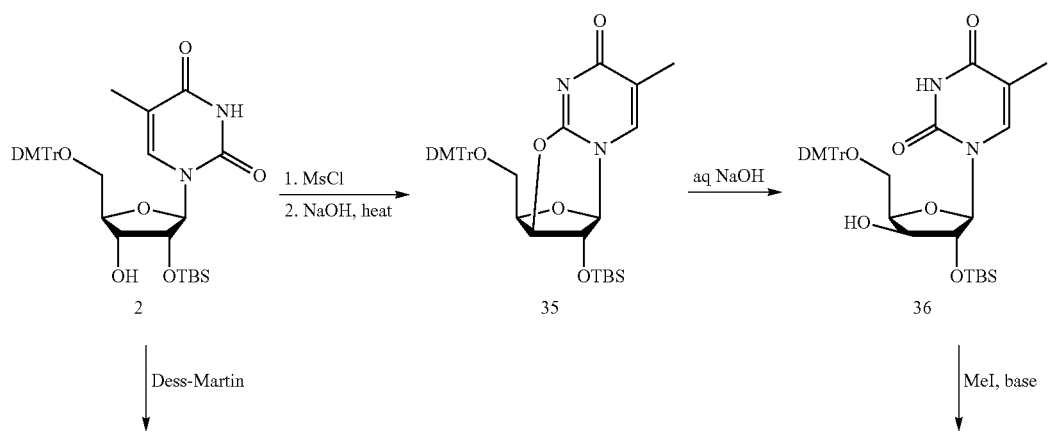

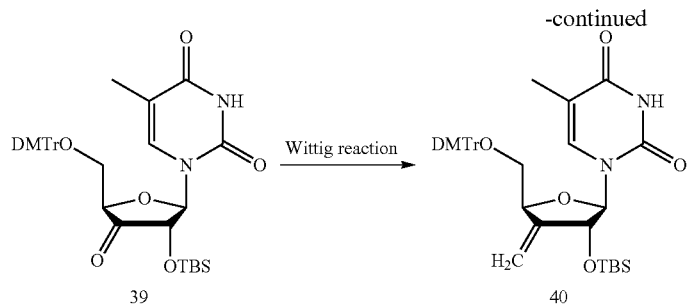
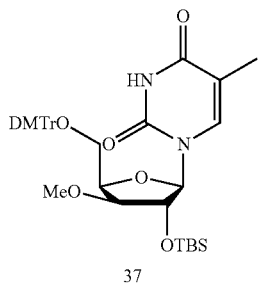
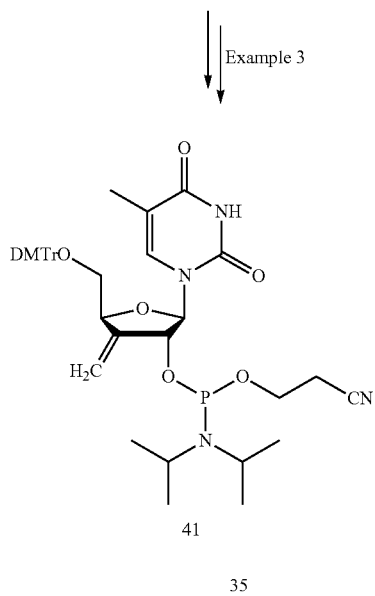
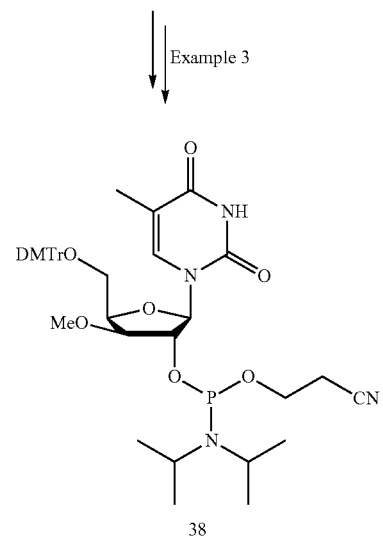

Generic Scheme 8 can be used to generate 5' modified nucleotides of Formula I, wherein A is —OC($R^3$)$_2$—, $R^3$ is H, and $R^1$ and $R^{1'}$ are H, —OMe, —OH or together =CH$_2$. These phosphoramidites can be used to make siNA molecules of the invention.

Example 1: Synthesis of Compound 8

Compound 8 is a phosphoramidite that can be used to generate single- and/or double-stranded siNA molecules comprising a "vinylP3dT" or "vinylP3dTs" nucleotide at the first nucleotide position of the molecule (position 1, which includes a 5' cap; also referred to herein as "5'-position 1"). The chemical structure for vinylP3dT and vinylP3dTs can be found within Table 14, infra. Generally, a similar synthesis procedure can be used to make phosphoramidites that are used to generate single and/or double-stranded siNA molecules comprising vinylP3dX or vinylP3dXs at position 1, wherein X is any heterocyclic base moiety.

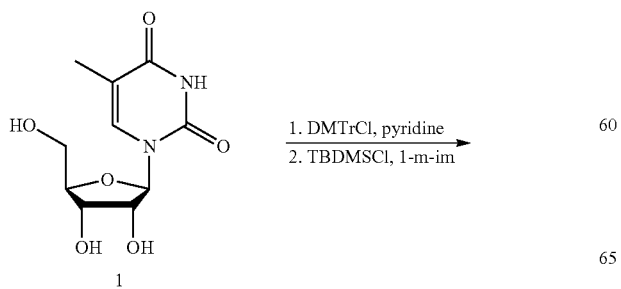
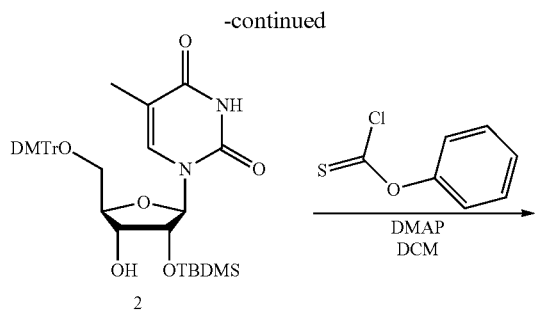
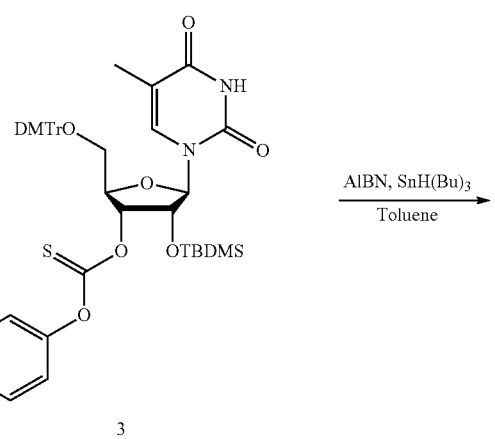

1.1. Preparation of Compound 2

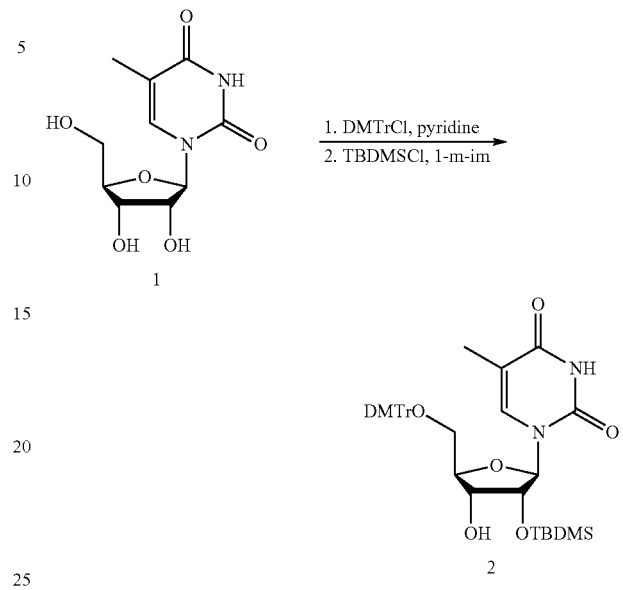

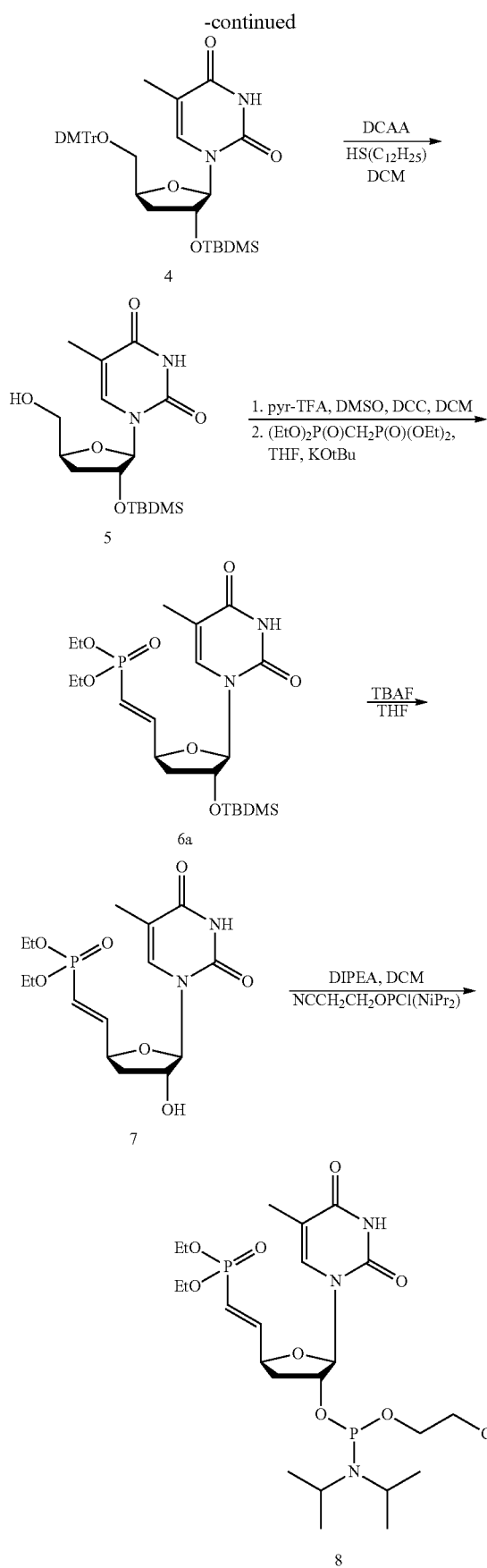

To a solution of 5-methyluridine (50 g, 194 mmol) 1 in anhydrous pyridine (300 mL) at rt was added 4,4'-dimethyloxytriyl chloride (66.9 g, 197 mmol) over 5 minutes. The resulting mixture was stirred at rt for 2 h followed by the addition of t-butyldimethylchlorosilane (30.3 g, 201 mmol) over 10 min. The resulting mixture was stirred for 12 h and 1-methylimidazole (3.09 mL, 38.7 mmol) and excess of t-butyldimethylchlorosiliane (20.4 g, mmol) were added. The resulting mixture was stirred for 8 h and then filtered. The filtrate was concentrated, diluted with EtOAC, washed with brine twice, dried over $Na_2SO_4$ and concentrated. The crude product was loaded onto a silica column (pre-equilibrated with Hex). It was eluted with 0 to 40% EtOAc in Hex to give the DMTr-TBDMS protected 5-methyluridine analog 2 as a white foam. $^1$H NMR (400 MHz, $CD_3CN$) δ=9.10 (s, 1H); 7.50 (d, J=1.2 Hz, 1H); 7.49-7.42 (m, 2H); 7.34-7.30 (m, 6H); 7.27-7.23 (m, 1H); 6.90-6.86 (m, 4H); 5.89 (d, J=5.6 Hz, 1H); 4.42 (t, J=5.3 Hz, 1H); 4.23 (dd, J=8.6, 0.8 Hz, 1H); 4.07-4.03 (m, 1H); 3.77 (s, 6H); 3.36-3.29 (m, 2H); 3.12 (d, J=4.8 Hz 1H); 1.41 (d, J=1.1 Hz, 3H); 0.91 (s, 9H); 0.13 (d, J=11.4 Hz, 6H)

1.2. Preparation of Compound 3

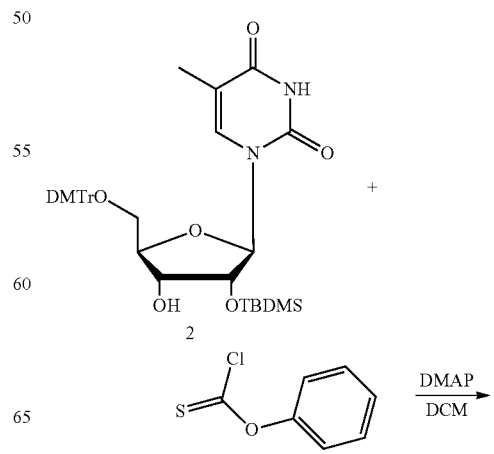

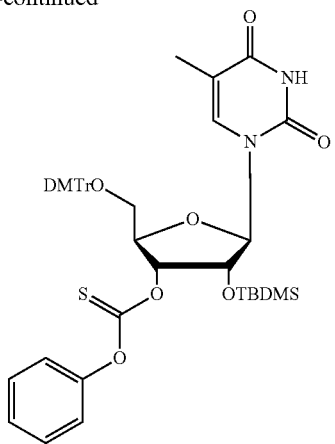

3

To a solution of compound 2 (28.16 g, 41.7 mmol) in anhydrous DCM (170 mL) at rt was added 4-dimethylaminopyridine (15.29 g, 125 mmol). The resulting mixture was stirred until all solids fully dissolved. Phenyl chlorothionocarbonate (10.13 mL, 75 mmol) was added to the reaction mixture over 5 minutes. The resulting mixture was stirred at rt for 24 h. The crude reaction was concentrated under reduced pressure. The crude product was dissolved in minimal amount of $CH_2Cl_2$ and loaded to silica column (pre-equilibriated with Hex). It was eluted with 0 to 30% EtOAc in Hex to give compound 3 as off-white foam. $^1$H NMR (400 MHz, $CDCl_3$) δ=8.39 (s, 1H); 7.68 (d, J=1.1 Hz, 1H); 7.46-7.42 (m, 4H); 7.33-7.29 (m, 8H); 7.09-7.07 (m, 2H); 6.87-6.84 (m, 4H); 6.15 (d, J=5.8 Hz, 1H); 6.00 (dd, J=5.0, 3.4 Hz, 1H); 4.74 (t, J=5.5 Hz, 1H); 4.43-4.41 (m, 1H); 3.80 (d, J=1.7 Hz, 6H); 3.56-3.49 (m, 2H); 1.45 (d, J=0.9 Hz, 3H); 0.93 (s, 9H); 0.15 (d, J=13.6 Hz, 6H).

1.3. Preparation of Compound 4

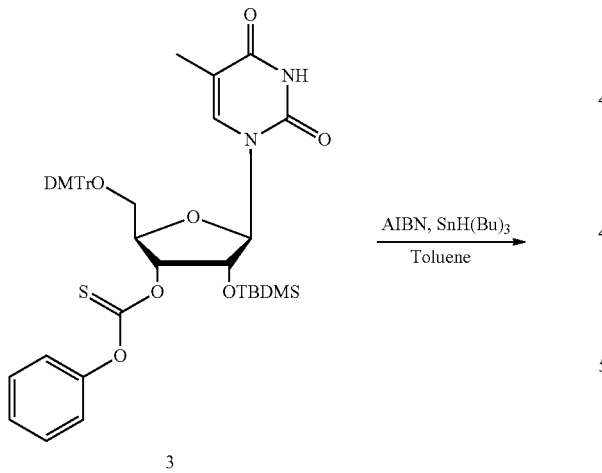

Compound 3 (18.44 g, 22.74 mmol) and AIBN (3.88 g, 23.65 mmol) were dissolved in anhydrous, degassed toluene (180 mL). To the resulting mixture was added Tri-n-butyltin hydride (11.7 mL, 43.7 mmol) over 3 minutes at rt. The resulting mixture was heated to 95° C. for 1 hour, cooled to rt, concentrated, and loaded to a silica column. The crude product was eluted with 0 to 40% EtOAc in Hex to give compound 4 as a white foam. $^1$H NMR (400 MHz, $CDCl_3$) δ=8.44 (s, 1H); 7.72 (d, J=1.2 Hz, 1H); 7.45-7.42 (m, 2H); 7.35-7.25 (m, 7H); 6.87-6.83 (m, 4H); 5.76 (d, J=1.52 Hz, 1H); 4.58-4.54 (m, 1H); 4.47-4.46 (m, 1H); 3.80 (d, J=0.4 Hz, 6H); 3.61 (dd, J=10.9, 2.2 Hz, 1H); 3.31-3.22 (m, 1H); 2.24-2.17 (m, 1H); 1.89-1.84 (m, 1H); 1.40 (d, J=1.0 Hz, 3H); 0.90 (s, 9H); 0.17 (d, J=22.0 Hz, 6H).

1.4. Preparation of Compound 5

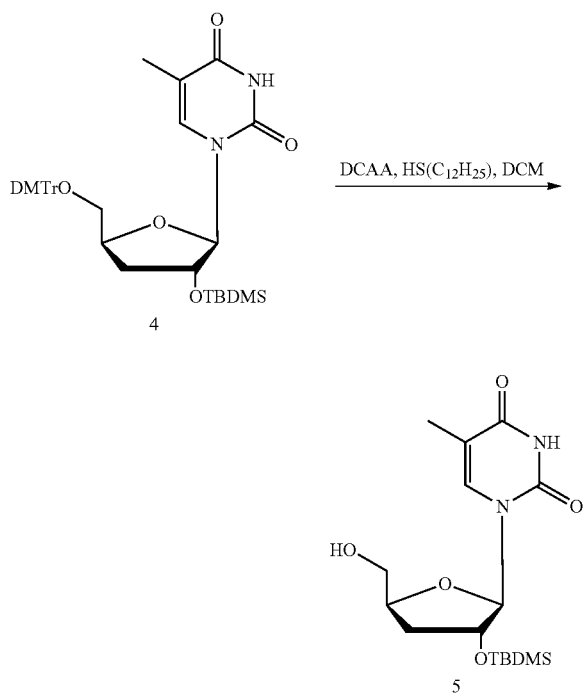

To a solution of compound 4 (4.9 g, 7.44 mmol) in anhydrous DCM (50 mL) was added dichloroacetic acid (1.66 mL, 20.08 mmol) and dodecanethiol (1.781 mL, 7.44 mmol). The resulting mixture was stirred at rt for 25 min followed by the addition of 0.6 M sodium bicarbonate solution (37.2 mL, 22.31 mmol). The aqueous layer was extracted once with DCM, dried over $MgSO_4$ and concentrated under reduced pressure. The crude product was loaded onto a silica column (pre-equilibrated with Hex). It was eluted with 0 to 50% EtOAc in Hex to give compound 5 as a colorless oil. $^1$H NMR (400 MHz, $CDCl_3$) δ=8.95 (s, 1H); 7.61 (s, 1H); 5.62 (d, J=1.9 Hz, 1H); 4.50-4.47 (m, 2H); 4.09 (dd, J=12.2, 2.24 Hz, 1H); 3.74 (dd, J=12.2, 3.1 Hz, 1H); 2.19-2.12 (m, 1H); 1.89 (s, 3H); 1.87-1.81 (m, 1H); 0.88 (s, 9H); 0.11 (d, J=13.2 Hz, 6H).

1.5. Preparation of Compound 6a

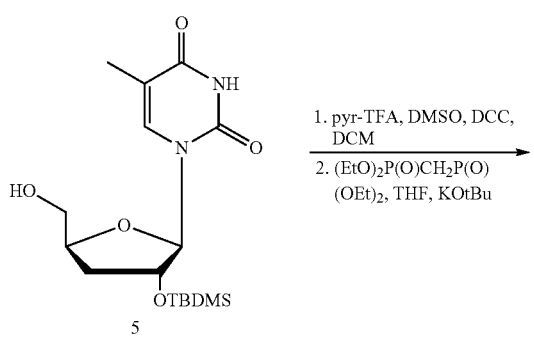

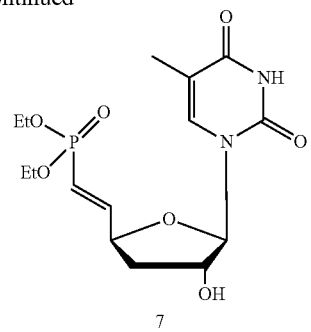

To a solution of compound 5 (2.16 g, 6.07 mmol) and pyridine-TFA (0.586 g, 3.04 mmol) in anhydrous DMSO (4 mL) at 0-5° C. was added DCC (1.0 M solution in DCM, 18.22 mL, 18.22 mmol) over 3 min. The resulting mixture was stirred at rt for 1 h. The crude aldehyde solution was used in the following reaction without further purification. In a separate reaction vessel, tetraethyl methylenediphosphonate (2.411 mL, 9.70 mmol) was dissolved in anhydrous THF (10 mL) and cooled to 0° C., followed by addition of potassium t-butoxide (1.0 M, 9.10 mL) and agitated at rt for 30 min and then cooled to 0° C. The solution containing aldehyde was added to this solution at 0° C. and agitated for 15 min. The resulting mixture was quenched into a mixture of brine and EtOAC, and pH adjusted to ~8 with NH$_4$Cl. The organic layer was washed twice with brine, dried over MgSO$_4$ and concentrated under reduced pressure. The crude product was loaded onto a silica column (pre-equilibrated with Hex). It was eluted with 0 to 80% EtOAc in Hex to give 6a as white foam. $^1$H NMR (400 MHz, CDCl$_3$) δ=8.84 (s, 1H); 7.13 (d, J=1.2 Hz, 1H); 6.97 (dt, J=22.0, 4.3 Hz, 1H); 6.12 (dt, J=18.9, 1.76 Hz, 1H); 5.77 (d, J=0.6 HZ, 1H); 5.01-4.97 (m, 1H); 4.39 (d, J=4.2 Hz, 1H); 4.17-4.08 (m, 4H); 4.09-4.05 (m, 1H); 2.11-2.06 (m, 2H); 1.90 (d, J=1.1 Hz, 3H); 1.81-1.74 (m, 1H); 1.37-1.33 (m, 6H); 0.90 (s, 9H); 0.16 (d, J=21.5 Hz, 6H).

1.6. Preparation of Compound 7

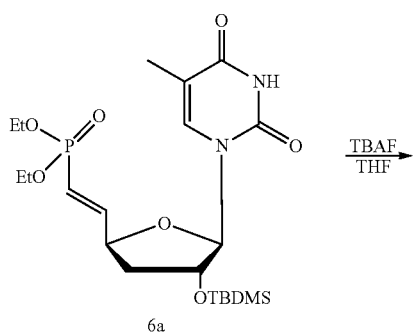

To a solution of compound 6a (10.3 g, 21.08 mmol) in THF (50 mL) was added TBAF (1.0 M in THF, 25.3 mL, 25.3 mmol). The solution was stirred at rt for 1 h and concentrated to oil under reduced pressure. The crude product was loaded onto a C18 column and eluted with 5 to 50% ACN in water to afford compound 7. $^1$H NMR (400 MHz, CDCl$_3$) δ=10.64 (s, 1H); 7.24 (d, J=0.9 Hz, 1H); 6.98 (dt, J=21.9, 4.4 Hz, 1H); 6.12 (dt, J=18.8, 1.6 Hz, 1H); 5.85 (s, 1H); 5.10-5.07 (m, 1H); 4.48-4.5 (d, J=4.8 Hz, 1H); 4.16-4.07 (m, 4H); 2.34-2.29 (dd, J=13.2, 5.6 Hz, 1H); 1.87 (s, 3H); 1.83-1.76 (m, 1H); 1.36-1.32 (m, 6H).

1.7. Preparation of Compound 8

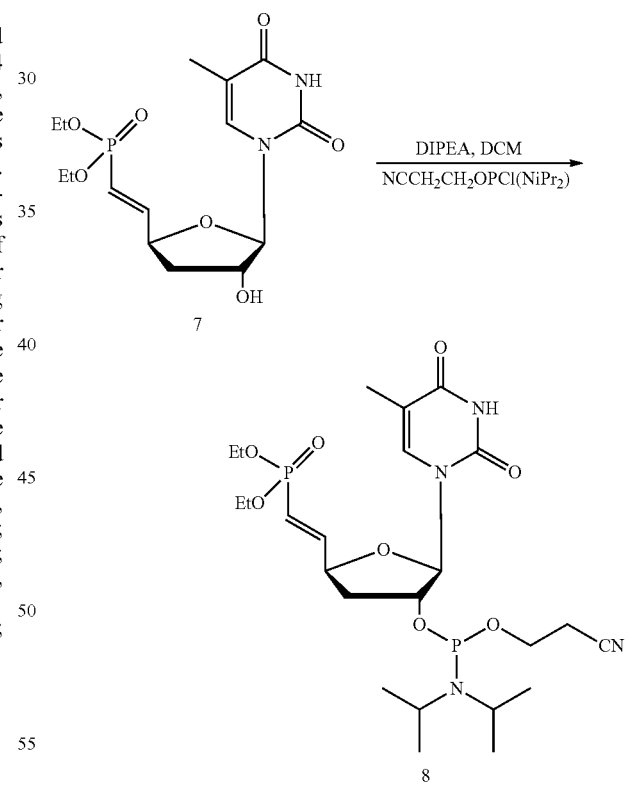

To a solution of compound 7 (4.49 g, 18.97 mmol) and DIPEA (6.63 mL, 37.9 mmol) in DCM (15 mL) at 0° C. was added 2-cyanoethyl N,N-diisopropylchlorophosphoramidite (4.23 mL, 18.97 mmol). The mixture was stirred at room temperature for 30 min, concentrated and loaded onto a cyano column. The sample was eluted with 0 to 50% EtOAC in HEX with TEA (0.15%) to afford compound 8 as white foam. $^1$H NMR (500 MHz, CDCl$_3$) δ=8.76 (s, 1H); 7.11 (t, J=1.0 Hz, 1H); 6.95-6.88 (m, 1H); 6.10-6.01 (m, 1H); 5.96 (d, J=7.4 Hz, 1H); 4.95-4.92 (m, 1H); 4.60-4.57 (m, 1H);

4.16-4.08 (m, 4H); 3.94-3.75 (m, 2H); 3.66-3.60 (m, 2H); 2.68-2.64 (m, 2H); 2.40-2.24 (m, 1H); 1.91 (dd, J=2.7, 1.1 Hz, 3H); 1.36 (dt, J=7.2, 1.6 Hz, 6H); 1.33-1.17 (m, 12H).

Example 2: Synthesis of Compound 12

Compound 12 is a phosphoramidite that can be used to generate single- and/or double-stranded siNA molecules comprising a "3daraT" or "3daraTs" nucleotide at the first nucleotide position of the molecule (position 1, which includes a 5' cap; also referred to herein as "5-position 1"). The chemical structure for 3daraT or 3daraTs can be found within Table 14, infra.

2.1. Preparation of Compound 9

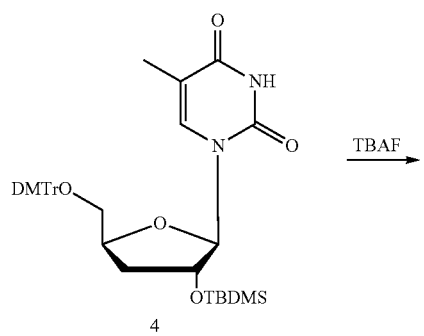

To the solution of compound 4 (2.2 g, 3.34 mmol) in THF (10 ml) was charged with 1.0 M TBAF in THF (4.01 ml, 4.01 mmol) at rt. The batch was agitated for 1 h and then concentrated. The crude product was purified by silica with 0 to 95% EtOAC in Hex to afford compound 9 as colorless oil. $^1$H NMR (400 MHz, CD$_3$CN) δ=7.47-7.43 (m, 3H), 7.34-7.29 (m, 6H), 7.26-7.22 (m, 1H), 6.89-6.85 (m, 4H), 5.70 (d, J=2.2 Hz, 1H), 4.48-4.43 (m, 1H), 4.39-4.36 (m, 1H), 3.34-3.24 (m, 2H), 2.23-2.15 (m, 2H), 1.46 (d, J=1.2 Hz, 3H)

2.2. Preparation of Compound 10

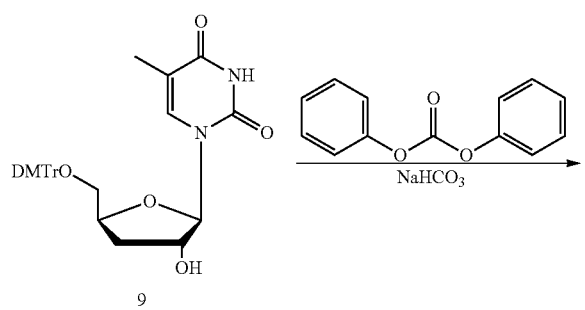

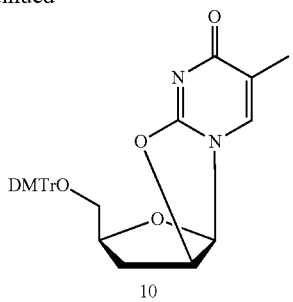

To the solution of compound 9 (455 mg, 0.835 mmol) in 2 ml DMF was charged diphenyl carbonate (197 mg, 0.919 mmol) and sodium bicarbonate (2.11 mg, 0.025 mmol) at rt. It was agitated till all solid dissolve. The batch was heat at 100° C. for 1 hour and then quenched to mixture of EtOAc and Brine. The aqueous was back extracted with EtOAC twice. The combined organic was concentrated to oil and purified by silica with 0 to 100% acetone in Hex to afford compound 10 as white solid. $^1$H NMR (400 MHz, CD$_3$CN) δ=7.44-7.43 (m, 1H), 7.35-7.33 (m, 2H), 7.28-7.17 (m, 7H), 6.82-6.79 (m, 4H), 6.08 (d, J=5.6 Hz, 1H), 5.40 (m, 1H), 4.60-4.54 (m, 1H), 2.96-2.77 (m, 2H), 2.52-2.44 (m, 1H), 2.22-2.17 (m, 1H), 1.83 (d, J=1.2 Hz, 3H).

2.3. Preparation of Compound 11

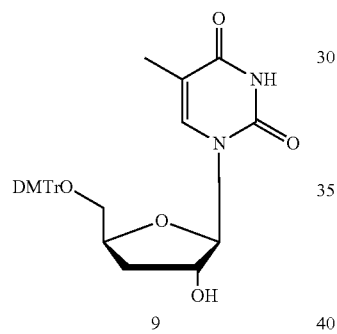

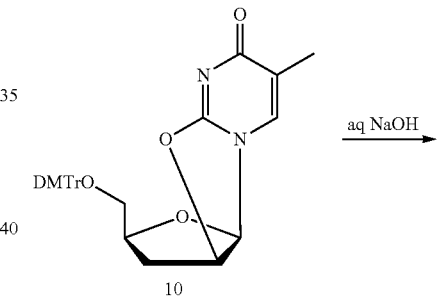

To the compound 10 (410 mg, 0.779 mmol) in 1 ml ethanol was charged 1.0 M NaOH solution (2.34 ml, 2.34 mmol). The mixture was agitated at rt for 3 h, quenched with acetic acid (0.080 ml, 1.4 mmol). The crude product was directly loaded on C18 column and purified with 0 to 75% MeCN in water to afford compound 11 as white solid. $^1$H NMR (400 MHz, CD$_3$CN) δ=9.27 (s, 1H) 7.48-7.45 (m, 3H), 7.34-7.29 (m, 6H), 7.26-7.21 (m, 1H), 6.89-6.85 (m, 4H), 5.94 (d, J=4.7 Hz, 1H), 4.44 (dd, J=11.4, 5.0 Hz, 1H), 4.21-4.15 (m, 1H), 3.33-3.25 (m, 2H), 2.27-2.30 (m, 2H), 1.65 (d, J=1.1 Hz, 3H)

2.4. Preparation of Compound 12

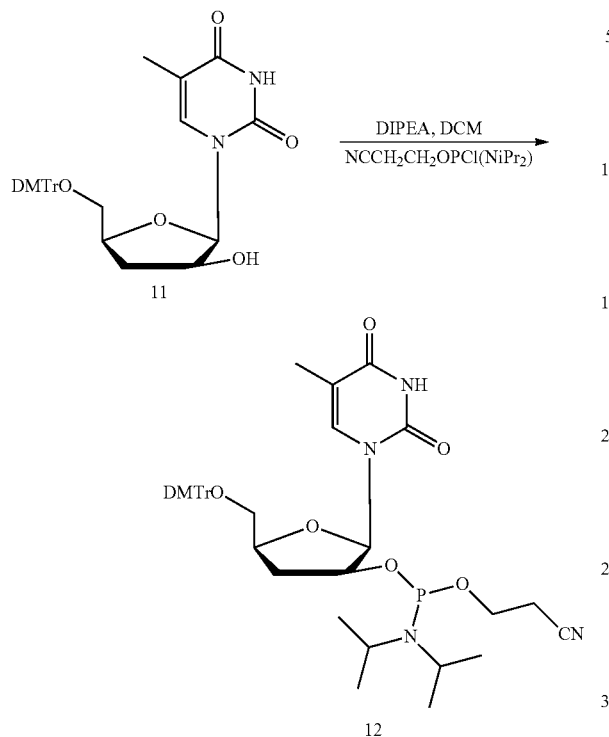

To the solution of compound 11 (379 mg, 0.696 mmol) and DIPEA (0.486 ml, 2.78 mmol) in 2 ml DCM was charged 2-Cyanoethyl N,N-diisopropylchlorophosphoramidite (0.310 ml, 1.39 mmol). The mixture was agitated at rt for 40 min and purified by cyano column with 0 to 85% EtOAC in Hex (0.15% Et$_3$N) to afford compound 12 as a white foam. $^1$H NMR (500 MHz, CD$_3$CN) δ=9.00 (s, 1H) 7.48-7.45 (m, 2H), 7.37-7.29 (m, 7H), 7.26-7.22 (m, 1H), 6.88-6.85 (m, 4H), 6.05, 6.02 (d, J=5.1 Hz, 1H), 4.62-4.55 (m, 1H), 4.28-4.19 (m, 1H), 3.67-3.55 (m, 2H), 3.48-3.39 (m, 2H), 3.35-3.26 (m, 2H), 2.59, 2.42 (m, 2H), 2.56-2.27 (m, 1H), 2.07-1.96 (m, 1H), 1.66, 1.64 (d, J=1.1 Hz, 3H), 1.11-0.93 (m, 12H)

Example 3: Synthesis of Compound 14

Compound 14 is a phosphoramidite precursor that can be used to generate single- and/or double-stranded siNA molecules comprising a "3rT" or "3rTs" nucleotide at the first nucleotide position of the molecule (position 1, which includes a 5' cap; also referred to herein as "5-position 1"). The chemical structure for 3rT or 3rTs can be found within Table 14, infra. Generally, the same synthesis procedure can be used to make phosphoramidites that are used to generate single and/or double-stranded siNA molecules comprising 3rX or 3rXs at position one, wherein X is any heterocyclic base moiety.

3.1. Preparation of Compound 2a

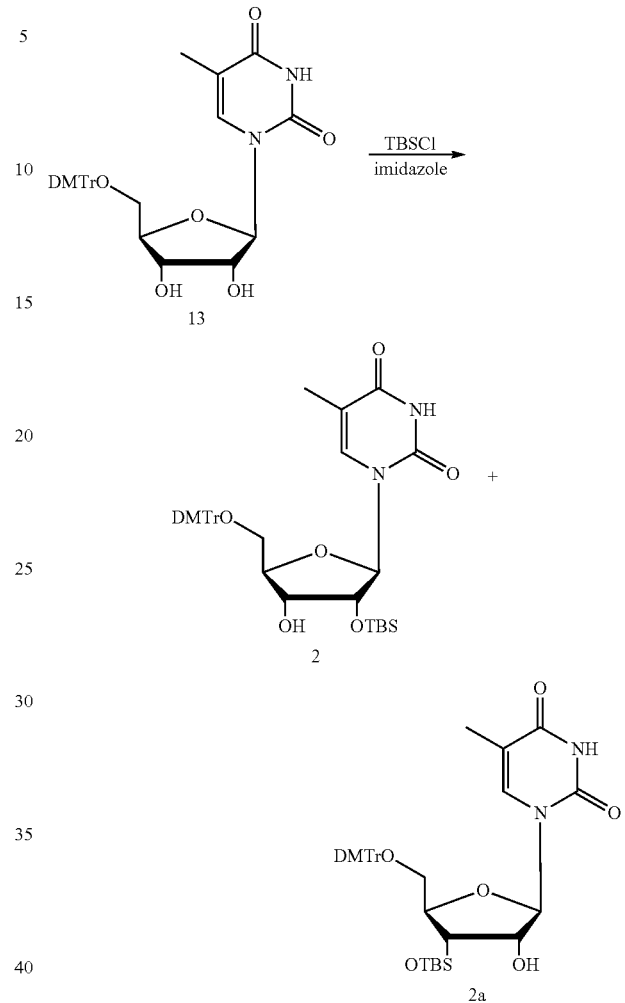

To a solution of 1-((2R,3R,4S,5R)-5-((bis(4-methoxyphenyl)(phenyl)methoxy)methyl)-3,4-dihydroxytetrahydrofuran-2-yl)-5-methylpyrimidine-2,4(1H,3H)-dione 13 (4.00 g, 7.14 mmol) in anhydrous pyridine (30 ml) at rt was added TBSCl (1.13 g, 7.49 mmol) and imidazole (1.21 g, 17.84 mmol). The resulting mixture was stirred at rt for 18 h. Then, it was concentrated under reduced pressure. EtOAc (50 ml), sat aq sodium citrate mono basic (20 ml) and water (10 ml) were added. Layers were separated and the aq layer was extracted with EtOAc (5 ml×2). Combined organic solution was washed with brine (5 ml), dried (MgSO$_4$), and concentrated. The crude was dissolved in minimal amount of CH$_2$Cl$_2$ and loaded to silica column (120 g, pre-equilibriated with Hex). It was eluted with 0 to 25% EtOAc in Hex to give 2'-OTBS product 2, and further elution with up to 40% EtOAc in Hex provided 3'-OTBS product 2a. $^1$H NMR (500 MHz, CDCl$_3$) δ 7.97 (s, 1H), 7.59 (s, 1H), 7.40-7.25 (m, 9H), 6.84 (d, J=10 Hz, 4H), 5.97 (d, J=5 Hz, 1H), 4.38 (m, 1H), 4.27 (m, 1H), 4.05 (m, 1H), 3.79 (s, 6H), 3.54 (d, J=5 Hz, 1H), 3.25 (d, J=10 Hz, 1H), 2.79 (d, J=10 Hz, 1H), 1.48 (s, 3H), 0.86 (s, 9H), 0.06 (s, 3H), −0.03 (s, 3H).

3.2. Preparation of Compound 14

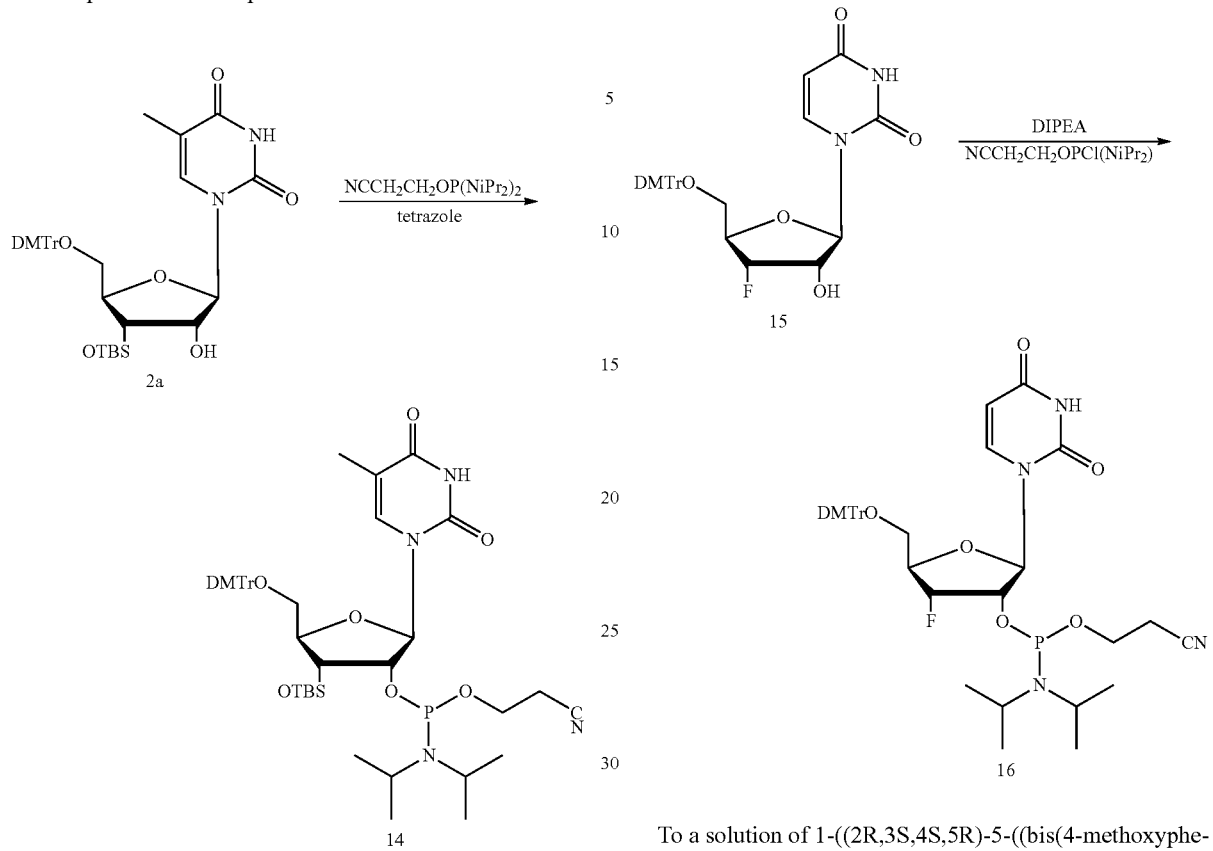

To a solution of 3'-OTBS-5'-ODMTr-5-methyluridine 2a (1.30 g, 1.93 mmol) in DCM (15 ml) at 0° C. was added tetrazole (54 mg, 0.771 mmol) and 2-cyanoethyl N,N,N',N'-tetraisopropylphosphoroamidite (0.795 ml, 2.50 mmol). The reaction was warmed to rt and stirred for 60 h. Then, DCM (30 ml) and sat aq NaHCO$_3$ (20 ml) were added. Layers were separated and the aq layer was extracted with DCM (2×10 ml). Combined organics were dried (MgSO$_4$), concentrated, and purified by column chromatography (eluted with 0 to 35% EtOAc) to give amidite 14 as a solid. $^1$H NMR (500 MHz, CDCl$_3$) δ 8.18 (s, 1H), 7.62 (s, 1H), 7.42-7.24 (m, 9H), 6.83 (d, J=10 Hz, 4H), 6.17 (d, J=5 Hz, 1H), 4.28 (m, 2H), 4.09 (d, J=5 Hz, 1H), 3.79 (m, 1H), 3.79 (s, 6H), 3.77 (m, 1H), 3.63 (m, 2H), 3.52 (d, J=10 Hz, 1H), 3.26 (d, J=10 Hz, 1H), 2.60 (m, 2H), 1.59 (s, 3H), 1.16-1.14 (m, 12H), 0.80 (s, 9H), 0.07 (s, 3H), −0.03 (s, 3H).

Example 4: Synthesis of Compound 16

Compound 16 is a phosphoramidite precursor that can be used to generate single- and/or double-stranded siNA molecules comprising a "3fluU" or "3fluUs" nucleotide at the first nucleotide position of the molecule (position 1, which includes a 5' cap; also referred to herein as "5-position 1"). The chemical structure for 3fluU or 3fluUs can be found within Table 13, infra. Generally, the same synthesis procedure can be used to make phosphoramidites that are used to generate single and/or double-stranded siNA molecules comprising 3fluX or 3fluXs at position one, wherein X is any heterocyclic base moiety.

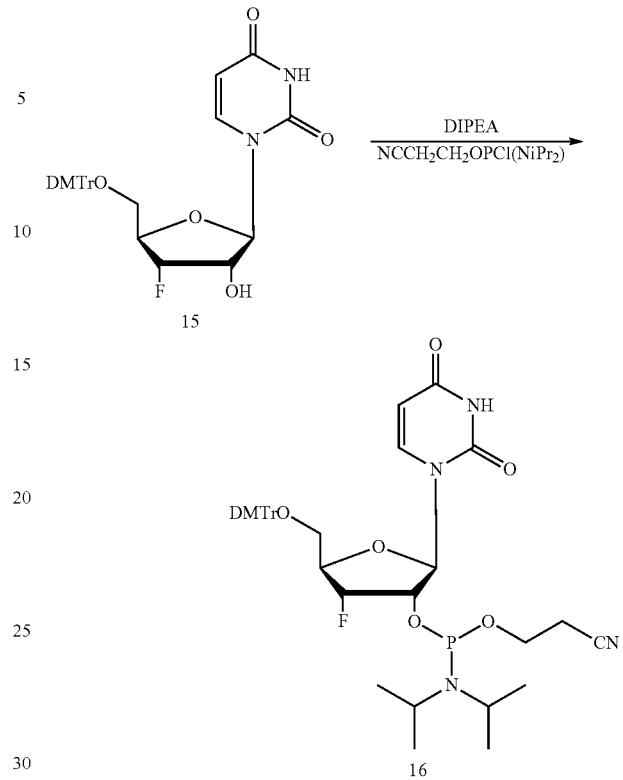

To a solution of 1-((2R,3S,4S,5R)-5-((bis(4-methoxyphenyl)(phenyl)methoxy)methyl)-4-fluoro-3-hydroxytetrahydrofuran-2-yl)pyrimidine-2,4(1H,3H)-dione 15 (0.78 g, 1.422 mmol) in anhydrous, degassed DCM (10 mL) at rt was added N,N-diisopropylethyl amine (0.551 g, 4.27 mmol) and 2-cyanoethyl N,N-diisopropylchlorophosphoramidite (0.673 g, 2.84 mmol). The resulting mixture was stirred at rt for 30 min. Then, it was concentrated under reduced pressure. The crude product was dissolved in minimal amount of CH$_2$Cl$_2$ and loaded to silica column (40 g, pre-equilibriated with Hex). It was eluted with 0 to 60% EtOAc in Hex to give amidite 16 as a white solid. $^1$H NMR (400 MHz, CD$_3$CN) δ 1.08 (d, J=6.8 Hz, 3H); 1.19-1.18 (m, 9H); 2.62 (dt, J=24.1, 6.0 Hz, 2H); 3.33 (dd, J=11.0, 3.1 Hz, 1H); 3.45 (ddd, J=11.0, 7.3, 3.3 Hz, 1H); 3.63-3.62 (m, 2H); 3.74 (dt, J=8.1, 6.1 Hz, 1H); 3.78 (s, 6H); 3.83-3.82 (m, 1H); 4.31-4.28, 4.38-4.35 (m, 1H); $^1$ 4.61-4.60 (m, 1H); 5.09-5.07, 5.22-5.20 (m, 1H); $^1$ 5.41 (t, J=8.1 Hz, 1H); 6.05 (t, J=6.3 Hz, 1H); 6.89-6.88 (m, 4H); 7.31-7.30 (m, 7H); 7.41 (d, J=7.8 Hz, 2H); 7.55 (dd, J=8.2, 4.7 Hz, 1H); 9.02 (s, 1H). $^{31}$P NMR (162 MHz, CD$_3$CN) δ 151.8, 151.9.

Example 5: Oligonucleotide Synthesis: General Protocol

Oligonucleotide duplexes were prepared by individual synthesis of two complementary oligonucleotide sense and antisense strands. The complementary strands of each duplex of a target sequence were synthesized on solid support, such as on controlled pore glass. After cleavage of each strand from the solid support and deprotection of all oligonucleotide protecting groups, each strand was purified chromatographically with a reversed phase (C18) or anion exchange (SAX) resin. After purification, each sense strand was annealed with its corresponding antisense strand and lyophilized to dryness.

The synthesis of each sense and antisense strand was accomplished on a solid support, such as controlled pore glass, using commercially available automated oligosynthesizers. The solid support was obtained pre-loaded with the first (3') nucleotide unit of the desired sequence and placed in an appropriate column for the oligosynthesizer. The first nucleotide was linked to the solid support via a succinate linkage and contained a suitable acid sensitive protecting group (e.g., trityl, dimethoxytrityl) on the 5'-terminal hydroxyl group. The solid-phase oligosynthesis employed synthetic procedures that are generally known in the art. Elongation of the desired oligomeric sequence went through a cycle of four steps: 1) acidic deprotection of the 5'-trityl protecting group; 2) coupling of the next nucleotide unit as the 5'-trityl (or dimethoxytrityl) protected phosphoramidite in the presence of an activating agent, such as S-ethyl-tetrazole; 3) oxidation of the P(III) phosphite triester to the P(V) phosphate triester by an oxidizing agent, such as iodine; and, 4) capping any remaining unreacted alcohol groups through esterification with an acylating agent, such as acetic anhydride. The phosphoramidites used were either derived from naturally occurring nucleotide units or from chemical modified versions of these nucleotides. Typically, all phosphoramidites were prepared in solutions of acetonitrile (or other suitable solvents or solvent mixtures, such as acetonitrile with some percentage of dimethyl formamide). The activator for phosphoramidite coupling was typically dissolved in acetonitrile. An oxidizing agent, such as iodine, was dissolved in a suitable solvent mixture, such as acetonitrile, pyridine and water. Acidic detritylation reagents, such as dichloroacetic acid or trichloroacetic acid, were dissolved in appropriate solvents, such as toluene or dichloromethane. Acylating capping reagents were, for example, a mixture of acetic anhydride, 2,6-lutidine and N-methyl-imidazole in acetonitrile. In place of the oxidation of the phosphite triester to the phosphate triester, the P(III) intermediate may be converted to the phosphorothioate analog with a sulfurizing reagent, such as phenyl-acetyl-disulfide, in a suitable solvent, such as a mixture of acetonitrile and pyridine. In between each step of the oligonucleotide elongation, acetonitrile (or another suitable solvent) was used to remove excess reagents and wash the solid support.

Oligonucleotide synthesis cycles were continued until the last (5') nucleotide unit was installed onto the extended oligomer. After the final cycle, the 5'-trityl protecting group may or may not be removed from the oligonucleotide while it remains on the solid support. In some instances, the 5'-terminal trityl was first removed by treatment with an acidic solution. After this deprotection, the solid support was treated with an appropriate base, such as aqueous methyl amine (at either room temperature or with mild heating) in order to cleave the oligonucleotide from the support, remove the cyanoethyl protecting groups on the phosphates and deprotect the acyl protecting groups on the nucleotide bases. Purification of these oligonucleotides would then be accomplished by SAX chromatography. Typically, the oligonucleotide was eluted from the SAX resin with a gradient of an inorganic salt, such as sodium chloride. Salt was removed from the purified samples by dialysis or tangential flow filtration. The desalted material was then lyophilized or annealed directly with the corresponding complementary strand. Alternatively, the purified single strands were annealed prior to removal of salt and then dialyzed after duplex formation.

In other instances, the 5'-trityl protecting group was left on the oligonucleotide during basic cleavage from the solid support and deprotection of the oligonucleotide protecting groups. In this case, the oligonucleotide was purified with a reversed phase resin, such as C18. The presence of the trityl group allowed for the desired full length oligonucleotide to be retained on the resin, while undesired truncated products that were acylated during the capping reaction were washed from the resin. These undesired oligonucleotides were removed from the resin with a lower percentage of an organic solvent, such as acetonitrile. After this removal of failure products, the trityl group was removed by acidic treatment (aqueous trifluoroacetic acid) while still on the C18 resin. After a salt exchange and extensive washing of the resin with water, the desired deprotected product was eluted with a higher percentage of organic solvent in water. These purified oligonucleotides were then either lyophilized or annealed directly with the corresponding complementary strand.

If the oligonucleotide contained any ribose (2'-hydroxyl) nucleotides, a modified procedure was required to remove the silyl 2'-hydroxyl protecting groups. After cleaving the oligonucleotide from the solid support with aqueous base, the column was further washed with an appropriate solvent, such as DMSO, to remove any material remaining on the column. After basic deprotection of the oligonucleotide, the reaction mixture then was treated with an appropriate fluoride reagent, such as triethylamine-hydrogen fluoride, to cleave all of the silyl ethers and expose the desired alcohols. After silyl deprotection was complete, an appropriate buffer was added to each sample in order to neutralize the solution prior to purification (either by SAX or C18).

In certain cases, a 5'-phosphonate-3'-phosphoramidite was coupled to the 5'-terminus of an oligonucleotide. The oxidation reagent for this incorporation was t-butyl hydroperoxide rather than iodine. When an oligonucleotide contained a 5'-phosphonate moiety, the methyl (or ethyl) phosphate esters were deprotected with an appropriate reagent, such as iodotrimethylsilane in pyridine/acetonitrile, while the oligonucleotide was still on the solid support. After washing the support with acetonitrile, the oligonucleotide was treated with β-mercaptoethanol in triethylamine/acetonitrile. After further washing with acetonitrile, the oligonucleotide product was cleaved from the solid support and fully deprotected with aqueous methylamine. The 5'-phosphonate oligonucleotides were purified by either SAX or C18 chromatography.

Each purified oligonucleotide was analyzed for purity by appropriate methods, including reversed phase HPLC, SAX HPLC and capillary gel electrophoresis. The identity of the oligonucleotide was confirmed by mass spectrometry, using an ionization technique such as ESI or MALDI. The yields of each oligonucleotide were assessed by UV (260 nm) with a theoretically derived extinction coefficient.

The corresponding sense and antisense strands were annealed by mixing equimolar amounts of each material. The appropriate amounts of each strand were approximated by UV (260 nm) measurements and theoretical extinction coefficients. After the annealing process, the extent of duplex formation and the presence of any excess single strand material were assessed by an appropriate chromatographic method, such as RP-HPLC or SAX. When appropriate, the sample was adjusted with additional amounts of one of the two strands in order to completely anneal the remaining excess single strand. The final duplex material was lyophilized prior to delivery for further biochemical or biological testing.

Example 6: Single-Stranded siNA Molecules Containing Modifications at 5'-Position 1

Table 2 shows various chemically-modified single-stranded siNA molecules synthesized using the protocol provided in Example 2 to 5. The single-stranded siNA molecules within Table 2 are comprised of 21 nucleotides (position 1 (5') to position 21 (3')) and contain differential modifications at nucleotide position 1. The name of each siNA molecule is provided in column 1 and corresponds to the composition of the nucleotide at position 1. An "siNA name" designated for an siNA molecule in Table 2 is used in other Tables and Figures to represent that particular siNA molecule. Column 2 ("5'-position 1 nucleotide") describes position 1 of each siNA molecule, comprising a nucleotide with a 5' cap. The chemical structure of each of the 5'-position 1 nucleotides is provided in Table 14, infra. For example, the 5'-position 1 nucleotide of the benchmark ("BM") siNA molecule, "p-omeU," comprises a chemically-modified uracil nucleotide with an O-methyl group at the 2' position of the sugar and a natural 5' phosphate cap. The nucleotide sequence spanning positions 2-20 for each of the siNA molecules is described in column 3 of Table 2, wherein the individual nucleotides are separated by a semicolon. The chemical structure of each nucleotide indicated within column 3 is provided for in Table 15, infra. For example, the chemical structure of the nucleotide located at position 2 of the BM siNA molecule, "flu," is a chemically-modified uracil nucleotide with a fluoro group at the 2' position of the sugar. The sequence of nucleotide positions 2-20 of each of the siNA molecules of Table 2 are the same (i.e., "(same)" with column 3). The 4$^{th}$ column of Table 2, "Nucleotide position 21-3'," represents the 3' most nucleotide of the siNA molecules of Table 2, each represented by "omeUSup". The structure of omeUSup is provided in Table 16, infra. The SEQ ID NO: for each siNA molecule of Table 2 (nucleotide positions 1-21) is provided in column 5.

TABLE 2

Single-stranded siNA molecules that are 21 nucleotides in length and contain differential modifications at position 1.

| siNA name | 5'-position 1 nucleotide | Nucleotide sequence - position 2 to position 20 | Nucleotide position 21-3' | SEQ ID NO. |
|---|---|---|---|---|
| BM | p-omeU | fluU; omeU; fluC; omeG; fluA; omeA; fluU; omeC; fluA; omeA; fluU; omeC; fluC; omeA; fluA; omeC; fluA; omeG; omeU | omeUSup | 1 |
| BMs | p-omeUs | (same) | (same) | 2 |
| dT | p-dT | (same) | (same) | 3 |
| dTs | p-dTs | (same) | (same) | 4 |
| 3dT | p-3dT | (same) | (same) | 5 |
| 3dTs | p-3dTs | (same) | (same) | 6 |
| 3dA | p-3dA | (same) | (same) | 7 |
| 3dAs | p-3dAs | (same) | (same) | 8 |
| 3dC | p-3dC | (same) | (same) | 9 |
| 3dCs | p-3dCs | (same) | (same) | 10 |
| 3dG | p-3dG | (same) | (same) | 11 |
| 3dGs | p-3dGs | (same) | (same) | 12 |
| 3priomeU | p-3priomeU | (same) | (same) | 13 |
| 3priomeUs | p-3priomeUs | (same) | (same) | 14 |
| 3fluU | p-3fluU | (same) | (same) | 15 |
| 3fluUs | p-3fluUs | (same) | (same) | 16 |
| 3daraT | p-3daraT | (same) | (same) | 17 |
| 3daraTs | p-3daraTs | (same) | (same) | 18 |
| 3rT | p-3rT | (same) | (same) | 19 |
| 3rTs | p-3rTs | (same) | (same) | 20 |
| vinylPmoeTs | vinylPmoeTs | (same) | (same) | 21 |
| vinylP3dT | vinylP3dT | (same) | (same) | 22 |
| vinylP3dTs | vinylP3dTs | (same) | (same) | 23 |

In Vitro Assay Targeting CTNNB1 (96-Well Plate Transfections)—

Cell Culture Preparation:

Mouse hepatoma cell line, Hepa1-6, was grown in Dulbecco's Modified Eagle's Medium that was supplemented with 10% fetal bovine serum, 100 µg/mL streptomycin, 100 U/mL penicillin, and 1% sodium pyruvate.

Transfection and Screening:

Cells were plated in all wells of tissue-culture treated, 96-well plates at a final count of 3500 cells/well in 100 µL, of the complete culture media. The cells were cultured overnight after plating at 37° C. in the presence of 5% $CO_2$.

On the next day, complexes containing siNA and Lipofectamine™ RNAiMax (Invitrogen) were created as follows. A solution of RNAiMax diluted 33-fold in OPTI-MEM was prepared. In parallel, solutions of the siNAs for testing were prepared to a final concentration of 120 nM in OPTI-MEM. After incubation of RNAiMax/OPTI-MEM solution at room temperature for 5 min, an equal volume of the siNA solution and the RNAiMax solution were added together for each of the siNAs.

Mixing resulted in a solution of siNA/RNAiMax where the concentration of siNA was 60 nM. This solution was incubated at room temperature for 15 minutes. After incubation, 20 µl of the solution was added to each of the relevant wells. The final concentration of siNA in each well was 10 nM and the final volume of RNAiMax in each well was 0.45 µL.

For low concentration screens, siNAs were transfected at 1000, 100 or 10 pM per well. For 12-point dose response curve studies, the siNA series are 6-fold serial dilution starting at 30 nM or 4-fold serial dilution starting at 40 nM. All transfections were set up as multiple biological replicates.

The time of incubation with the RNAiMax-siRNA complexes was 24 hours and there was no change in media between transfection and harvesting for screening and dose response curve studies.

Cells-to-Ct and Reverse Transcription Reactions:

The culture medium was aspirated and discarded from the wells of the culture plates at the desired time points. The transfected cells were washed once with 100 µL DPBS solution per well. Fifty microliters per well of the Lysis Solution from the TaqMan® Gene Expression Cells-to-CT™ Kit (Invitrogen, Cat#4399002) supplemented with DNase I was added directly to the plates to lyse the cells. Five microliters per well of Stop Solution from the same kit was added to the plates 5 minutes later. The lysis plates were incubated for at least 2 minutes at room temperature. The plates can be stored for 2 hours at 4° C., or −80° C. for two months.

Each well of the reverse transcription plate required 10 µL, of 2× reverse transcriptase buffer, 1 µL, of 20× reverse transcription enzyme and 2 µL, of nuclease-free water. The reverse transcription master mix was prepared by mixing 2× reverse transcription buffer, 20× reverse transcription enzyme mix, and nuclease-free water. 13 µL, of the reverse transcription master mix was dispensed into each well of the reverse transcription plate (semi-skirted). A separate reverse transcription plate was prepared for each cell plate. Seven microliters per lysate from the cell lysis procedure described above was added into each well of the reverse transcription plate. The plate was sealed and spun on a centrifuge (1000 rpm for 30 seconds) to settle the contents to the bottom of the reverse transcription plate. The plate was placed in a thermocycler at 37° C. for 60 min, 95° C. for 5 min, and 4°

C. until the plate is removed from the thermocycler. Upon removal, if not used immediately, the plate was frozen at −20° C.

Quantitative RT-PCR (Taqman):

A series of probes and primers were used to detect the various mRNA transcripts of the genes of CTNNB1 and GAPDH. All Taqman probes and primers for the experiments here-in described were supplied as pre-validated sets by Applied Biosystems, Inc. (see Table 3).

TABLE 3

Probes and primers used to carry out Real-Time RT/PCR (Taqman) reactions for CTNNB1 mRNA analysis.

| Species | Gene | ABI Cat.# |
|---|---|---|
| Human | CTNNB1 | Hs00355045_m1 |
| Human | GAPDH | 4310884E |
| Mouse | CTNNB1 | Mm00483033_m1 |
| Mouse | GAPDH | 4352339E |

The assays were performed on an ABI 7900HT instrument, according to the manufacturer's instructions. A Taq-Man Gene Expression Master Mix (provided in the CellstoCT™ Kit, Invitrogen, Cat #4399002) was used. The PCR reactions were carried out at 50° C. for 2 min, 95° C. for 20 sec followed by 40 cycles at 95° C. for 1 min and 60° C. for 20 sec.

Within each experiment, the baseline was set in the exponential phase of the amplification curve, and based on the intersection point of the baselines with the amplification curve; a Ct value was assigned by the instrument.

Calculations:

The expression level of the gene of interest and % inhibition of gene expression (% KD) was calculated using Comparative Ct method:

$$\Delta Ct = Ct_{Target} - Ct_{GAPDH}$$

$$\Delta\Delta Ct(\log 2(\text{fold change})) = \Delta Ct_{(Target\ siNA)} - \Delta Ct_{(NTC)}$$

Relative expression level $= 2^{-\Delta\Delta Ct}$ $$\% KD = 100 \times (1 - 2^{-\Delta\Delta Ct})$$

The non-targeting control siNA was, unless otherwise indicated, chosen as the value against which to calculate the percent inhibition (knock-down) of gene expression, because it is the most relevant control.

Additionally, only normalized data, which reflects the general health of the cell and quality of the RNA extraction, was examined. This was done by looking at the level of two different mRNAs in the treated cells, the first being the target mRNA and the second being the normalizer mRNA. This allowed for elimination of siNAs that might be potentially toxic to cells rather than solely knocking down the gene of interest. This was done by comparing the Ct for GAPDH in each well relative to the GAPDH Ct for the entire plate.

All calculations of IC50s were performed using R.2.9.2 software. The data were analyzed using the sigmoidal dose-response (variable slope) equation for simple ligand binding. In all of the calculations of the percent inhibition (knock-down), the calculation was made relative to the normalized level of expression of the gene of interest in the samples treated with the non-targeting control (Ctrl siRNA) unless otherwise indicated.

Results—

Subsets of the single-stranded siNA molecules of Table 2 were screened in Hepa1-6 cells transfected with RNAiMax.

Table 4 and FIG. 1A summarize the knock-down activities of regular 3'-5' linked single-stranded siNA molecules such as BM (benchmark), BMs, dT, and dTs, and new 2'-5 linked single-stranded siNA molecules such as 3dX and 3dXs, where X is T, A, C or G. The "s" designation within the siNA name indicates a phosphorothioate internucleotide linkage between nucleotide position 1 and 2 of the molecule. The "d" designation within the siNA name indicates a deoxy modification at nucleotide position 1 of the molecule (e.g., dT siNA has a deoxy modification at the $2^{nd}$ carbon position of the sugar at nucleotide position 1 and a 3'-5' phosphodiester internucleotide linkage between nucleotide positions 1 and 2; 3dT siNA has 2 H at the $3^{rd}$ carbon position of the sugar at nucleotide position 1 and a 2'-5' phosphodiester internucleotide linkage between nucleotide positions 1 and 2).

Each of the 2'-5' linked 3dX and 3dXs siNA molecules showed knock-down in this assay. In particular, the 2'-5' linked 3dT and 3dTs siNA molecules showed higher knock-down activities than the 3'-5' linked BM, BMs, dT, and dTs at all four concentrations (100 nM, 10 nM, 1 nM, and 0.1 nM). Among 2'-5' linked single-stranded siNA molecules, 3dT and 3dTs showed higher knock down activities than other 3dX and 3dXs, where X was A, C or G at all four concentrations (100 nM, 10 nM, 1 nM, and 0.1 nM). The 3dA, 3dAs, 3dC and 3dCs siNA molecules displayed knock-down activity that was slightly better or the same as benchmark molecules.

TABLE 4

In vitro transfection-based knock down activity for a subset of the single-stranded siNA molecules provided in Table 2 (see also FIG. 1A).

| siNA name | ddCT (100 nM) | ddCT (10 nM) | ddCT (1 nM) | ddCT (0.1 nM) |
|---|---|---|---|---|
| BM | 1.324 | 0.796 | 0.164 | −0.115 |
| BMs | 1.073 | 1.474 | 0.246 | 0.005 |
| dT | 2.553 | 2.854 | 0.996 | 0.350 |
| dTs | 1.543 | 2.159 | 0.636 | 0.175 |
| 3dT | 3.168 | 3.474 | 2.316 | 1.45 |
| 3dTs | 2.593 | 3.519 | 2.291 | 0.92 |
| 3dA | 1.667 | 1.074 | 0.139 | −0.008 |
| 3dAs | 1.484 | 1.331 | 0.249 | 0.040 |
| 3dC | 1.462 | 1.421 | 0.262 | 0.118 |
| 3dCs | 1.239 | 1.494 | 0.269 | 0.115 |
| 3dG | 0.614 | 0.191 | −0.043 | −0.003 |
| 3dGs | 0.459 | 0.229 | 0.004 | −0.013 |

Figure 1B:
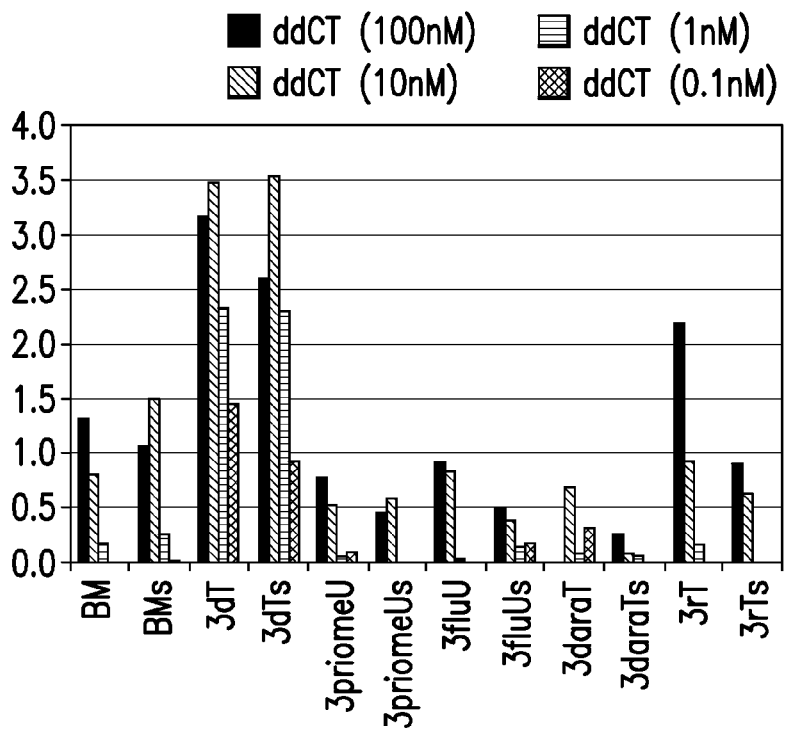
FIG. 1B compares the activity of single-stranded siNA molecules, each having a 2'-5' internucleoside linkage at position 1 and various additional structural changes at that position.

Table 5 and FIG. 1B summarize the knock-down activities for another subset of the siNA molecules shown in Table 2, comparing the activities of 2'-5' linked single-stranded siNA molecules with various structural changes in the nucleotide at position 1. Each of the 2'-5' linked single-stranded siNA molecules displayed knock-down activity in the assay. In particular, 3dT and 3dTs siNA molecules showed higher knock down activities than 3priomeU, 3priomeUs, 3fluU, 3fluUs, 3daraT, 3daraTs, 3rT, and 3rTs at all four concentrations (100 nM, 10 nM, 1 nM, and 0.1 nM).

TABLE 5

In vitro transfection-based knock down activity for a subset of the single-stranded siNA molecules provided in Table 2 (see also FIG. 1B).

| siNA name | ddCT (100 nM) | ddCT (10 nM) | ddCT (1 nM) | ddCT (0.1 nM) |
|---|---|---|---|---|
| BM | 1.324 | 0.796 | 0.164 | −0.115 |
| BMs | 1.073 | 1.474 | 0.246 | 0.005 |

TABLE 5-continued

In vitro transfection-based knock down activity for a subset of the
single-stranded siNA molecules provided in Table 2 (see also FIG. 1B).

| siNA name | ddCT (100 nM) | ddCT (10 nM) | ddCT (1 nM) | ddCT (0.1 nM) |
|---|---|---|---|---|
| 3dT | 3.168 | 3.474 | 2.316 | 1.45 |
| 3dTs | 2.593 | 3.519 | 2.291 | 0.92 |
| 3priomeU | 0.768 | 0.514 | 0.051 | 0.085 |
| 3priomeUs | 0.448 | 0.579 | −0.024 | −0.090 |
| 3fluU | 0.921 | 0.825 | 0.021 | −0.333 |
| 3fluUs | 0.481 | 0.373 | 0.126 | 0.155 |
| 3daraT | −0.046 | 0.669 | 0.070 | 0.289 |
| 3daraTs | 0.249 | 0.074 | 0.040 | −0.001 |
| 3rT | 2.188 | 0.919 | 0.135 | −0.245 |
| 3rTs | 0.908 | 0.614 | −0.095 | −0.350 |

Subsets of the single-stranded siNA molecules of Table 2 were assayed further for 12-point dose response curve. Table 6 summarizes the knock down activity of the single-stranded siNA molecules. 3dT and 3dTs showed lower IC50 values (column 2) and higher maximum knock-down activity (column 3) than other single-stranded siNA molecules, such as BM, BMs, dT, dTs, vinylPmoeTs, vinylP3dT, and vinylP3dTs.

TABLE 6

Dose-response in vitro transfection-based knock down activity for a
subset of the single-stranded siNA molecules provided in Table 2.

| siNA name | IC50 (nM) | Max KD (ddCT) |
|---|---|---|
| BM | 2.189 | −2.428 |
| BMs | 4.250 | −1.899 |
| dT | 0.813 | −2.779 |
| dTs | 0.848 | −2.167 |
| 3dT | 0.355 | −2.915 |
| 3dTs | 0.580 | −2.834 |
| vinylPmoeTs | 5.831 | −1.582 |

TABLE 6-continued

Dose-response in vitro transfection-based knock down activity for a
subset of the single-stranded siNA molecules provided in Table 2.

| siNA name | IC50 (nM) | Max KD (ddCT) |
|---|---|---|
| vinylP3dT | 3.341 | −1.994 |
| vinylP3dTs | 4.196 | −1.950 |

Example 7: Single-Stranded siNA Molecules Containing Internal 3dX Nucleotide Modifications The single-stranded siNA molecules within Table 7 are comprised of 21 nucleotides (position 1 (5') to position 21 (3')), and each molecule contains a single 3dX nucleotide, wherein X is base A, T, C, or G, located at different nucleotide positions. The name of each siNA molecule is provided in column 1 and corresponds to the nucleotide position containing the 3dX nucleotide and the base used at that position (e.g., "2(T)" indicates a 3dT nucleotide at position 2). An "siNA name" designated for an siNA molecule in Table 7 is used in other Tables and Figures to represent that particular siNA molecule. Column 2 of Table 7, "5'-position 1 nucleotide", represents the 5' most nucleotide of the siNA molecules of Table 7, each represented by "p-omeU" (see Table 14, infra, for the p-omeU structure). The nucleotide sequence spanning positions 2-20 for each of the siNA molecules is described in column 3 of Table 7, wherein the individual nucleotides are separated by a semicolon. The chemical structure of each nucleotide indicated within column 3 is provided for in Table 15, infra. The 3dX nucleotides within column 3 are underlined. The 4th column of Table 7, "Nucleotide position 21-3'", represents the 3' most nucleotide of the siNA molecules of Table 7, each represented by "omeUSup" (see Table 16, infra, for the omeUSup structure). The SEQ ID NO: for each siNA molecule of Table 7 (positions 1-21) is provided in column 5.

TABLE 7

Single-stranded siNA molecules containing a single, internal 3dX nucleotide
(underlined in column 3).

| siNA name | 5'-position 1 nucleotide | Nucleotide sequence - position 2 to position 20 | Nucleotide position 21-3' | SEQ ID NO. |
|---|---|---|---|---|
| 2(T) | p-omeU | 3dT; omeU; fluC; omeG; fluA; omeA; fluU; omeC; fluA; omeA; fluU; omeC; fluC; omeA; fluA; omeC; fluA; omeG; omeUs | omeUSup | 24 |
| 3(T) | (same) | fluU; 3dT; fluC; omeG; fluA; omeA; fluU; omeC; fluA; omeA; fluU; omeC; fluC; omeA; fluA; omeC; fluA; omeG; omeUs | (same) | 25 |
| 4(C) | (same) | fluU; omeU; 3dC; omeG; fluA; omeA; fluU; omeC; fluA; omeA; fluU; omeC; fluC; omeA; fluA; omeC; fluA; omeG; omeUs | (same) | 26 |
| 5(G) | (same) | fluU; omeU; fluC; 3dG; fluA; omeA; fluU; omeC; fluA; omeA; fluU; omeC; fluC; omeA; fluA; omeC; fluA; omeG; omeUs | (same) | 27 |
| 6(A) | (same) | fluU; omeU; fluC; omeG; 3dA; omeA; fluU; omeC; fluA; omeA; fluU; omeC; fluC; omeA; fluA; omeC; fluA; omeG; omeUs | (same) | 28 |
| 8(T) | (same) | fluU; omeU; fluC; omeG; fluA; omeA; 3dT; omeC; fluA; omeA; fluU; omeC; fluC; omeA; fluA; omeC; fluA; omeG; omeUs | (same) | 29 |
| 9(C) | (same) | fluU; omeU; fluC; omeG; fluA; omeA; fluU; 3dC; fluA; omeA; fluU; omeC; fluC; omeA; fluA; omeC; fluA; omeG; omeUs | (same) | 30 |
| 10(A) | (same) | fluU; omeU; fluC; omeG; fluA; omeA; fluU; omeC; 3dA; omeA; fluU; omeC; fluC; omeA; fluA; omeC; fluA; omeG; omeUs | (same) | 31 |
| 12(T) | (same) | fluU; omeU; fluC; omeG; fluA; omeA; fluU; omeC; fluA; omeA; 3dT; omeC; fluC; omeA; fluA; omeC; fluA; omeG; omeUs | (same) | 32 |
| 13(C) | (same) | fluU; omeU; fluC; omeG; fluA; omeA; fluU; omeC; fluA; omeA; fluU; 3dC; fluC; omeA; fluA; omeC; fluA; omeG; omeUs | (same) | 33 |
| 14(C) | (same) | fluU; omeU; fluC; omeG; fluA; omeA; fluU; omeC; fluA; omeA; fluU; omeC; 3dC; omeA; fluA; omeC; fluA; omeG; omeUs | (same) | 34 |
| 15(A) | (same) | fluU; omeU; fluC; omeG; fluA; omeA; fluU; omeC; fluA; omeA; fluU; omeC; fluC; 3dA; fluA; omeC; fluA; omeG; omeUs | (same) | 35 |

TABLE 7-continued

Single-stranded siNA molecules containing a single, internal 3dX nucleotide (underlined in column 3).

| siNA name | 5'-position 1 nucleotide | Nucleotide sequence - position 2 to position 20 | Nucleotide position 21-3' | SEQ ID NO. |
|---|---|---|---|---|
| 16(A) | (same) | fluU; omeU; fluC; omeG; fluA; omeA; fluU; omeC; fluA; omeA; fluU; omeC; fluC; omeA; <u>3dA</u>; omeC; fluA; omeG; omeUs | (same) | 36 |
| 17(C) | (same) | fluU; omeU; fluC; omeG; fluA; omeA; fluU; omeC; fluA; omeA; fluU; omeC; fluC; omeA; fluA; <u>3dC</u>; fluA; omeG; omeUs | (same) | 37 |
| 18(A) | (same) | fluU; omeU; fluC; omeG; fluA; omeA; fluU; omeC; fluA; omeA; fluU; omeC; fluC; omeA; fluA; omeC; <u>3dA</u>; omeG; omeUs | (same) | 38 |
| 19(G) | (same) | fluU; omeU; fluC; omeG; fluA; omeA; fluU; omeC; fluA; omeA; fluU; omeC; fluC; omeA; fluA; omeC; fluA; <u>3dG</u>; omeUs | (same) | 39 |
| 20(T) | (same) | fluU; omeU; fluC; omeG; fluA; omeA; fluU; omeC; fluA; omeA; fluU; omeC; fluC; omeA; fluA; omeC; fluA; omeG; <u>3dTs</u> | (same) | 40 |

Results—

Figure 2A:
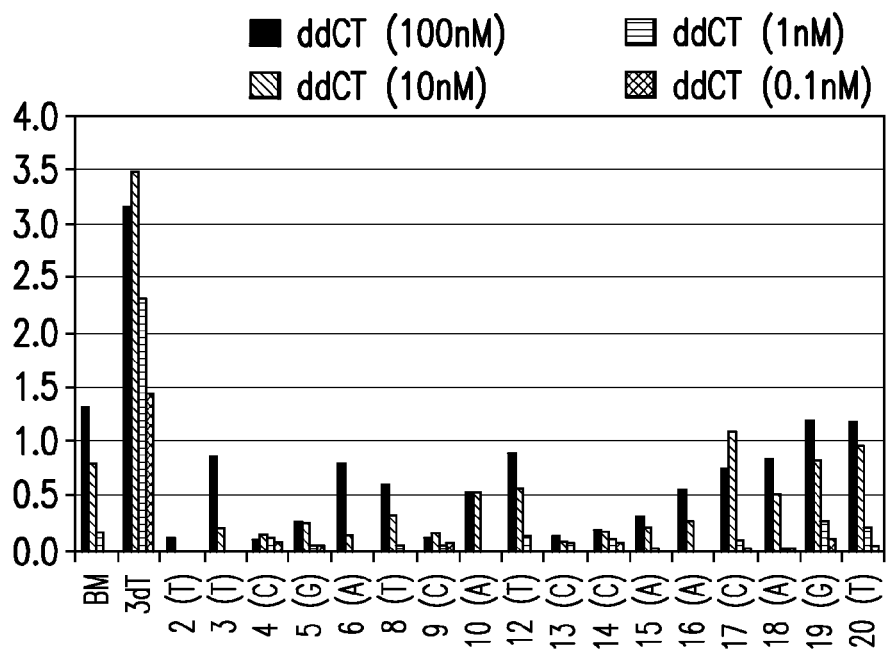
FIG. 2A compares knock-down activity (ddCT) of the single-stranded siNA molecules described in Table 8 at differing concentrations (100 nM, 10 nM, 1 nM and 0.1 nM). The knock-down activity was screened in Hepa1-6 cells transfected with RNAiMax (see Examples 6 and 7). The siNA molecules shown in this figure each contain internal nucleotides with 2'-5' internucleoside linkages.

The single-stranded siNA molecules of Table 7 were screened in Hepa1-6 cells transfected with RNAiMax, as in Example 6. Table 8 and FIG. 2A summarize the knock-down activities of these single-stranded siNA molecules containing internal 3dX nucleotide modifications. Each of the single-stranded siNA molecules tested displayed knock-down activity in the assay. In particular, the 3dT siNA molecule showed higher knock-down activity than the other single-stranded siNA molecules with internal 3dX, wherein X was base A, T, C, or G, at all four concentrations (100 nM, 10 nM, 1 nM, and 0.1 nM).

TABLE 8

In vitro transfection-based knock down activity for each of the single-stranded siNA molecules provided in Table 7, and the BM and 3dT siNA molecules (see Table 2) (see also FIG. 2A).

| siNA name | ddCT (100 nM) | ddCT (10 nM) | ddCT (1 nM) | ddCT (0.1 nM) |
|---|---|---|---|---|
| BM | 1.324 | 0.796 | 0.164 | −0.115 |
| 3dT | 3.168 | 3.474 | 2.316 | 1.45 |
| 2 (T) | 0.107 | −0.194 | −0.043 | −0.080 |
| 3 (T) | 0.854 | 0.199 | −0.163 | −0.175 |
| 4 (C) | 0.097 | 0.141 | 0.114 | 0.077 |
| 5 (G) | 0.259 | 0.234 | 0.044 | 0.048 |
| 6 (A) | 0.797 | 0.139 | −0.086 | −0.043 |
| 8 (T) | 0.604 | 0.316 | 0.039 | −0.035 |
| 9 (C) | 0.122 | 0.164 | 0.039 | 0.055 |
| 10 (A) | 0.539 | 0.526 | −0.026 | −0.133 |
| 12 (T) | 0.892 | 0.564 | 0.122 | −0.042 |
| 13 (C) | 0.134 | 0.084 | 0.064 | −0.050 |
| 14 (C) | 0.184 | 0.174 | 0.099 | 0.062 |
| 15 (A) | 0.317 | 0.201 | 0.004 | −0.042 |
| 16 (A) | 0.562 | 0.259 | −0.053 | −0.025 |
| 17 (C) | 0.752 | 1.079 | 0.089 | 0.005 |
| 18 (A) | 0.837 | 0.519 | 0.022 | 0.025 |
| 19 (G) | 1.199 | 0.826 | 0.257 | 0.107 |
| 20 (T) | 1.177 | 0.951 | 0.209 | 0.043 |

Example 8: Single-Stranded siNA Molecules Containing a 3dT-Related Nucleotide at Position 1 and Multiple Phosphorothioate Internucleotide Linkages Table 9 shows various chemically-modified single-stranded siNA molecules synthesized using the protocol provided in Example 5. The single-stranded siNA molecules within Table 9 are comprised of 21 nucleotides (position 1 (5') to position 21 (3')), each containing a single 3dT or 3dTs nucleotide at position 1 and multiple phosphorothioate internucleotide linkages. A 3dTs nucleotide contains a phosphorothioate internucleotide linking group. The name of each siNA molecule is provided in column 1 and corresponds to the number of phosphorothioate internucleotide linkages contained within an siNA molecule (e.g., the "14S" siNA molecule contains 14 phosphorothioate internucleotide linkages). An "siNA name" designated for an siNA molecule in Table 9 is used in other Tables and Figures to represent that particular siNA molecule. Column 2 of Table 9, "5'-position 1 nucleotide", represents the 5' most nucleotide of the siNA molecules of Table 9, each represented by either "p-3dT" or "p-3dTs" (for structures, see Table 14, infra). The nucleotide sequence spanning positions 2-20 for each of the siNA molecules is described in column 3 of Table 9, wherein the individual nucleotides are separated by a semicolon. The chemical structure of each nucleotide indicated within column 3 is provided for in Table 15, infra. The phosphorothioate internucleotide linking groups are indicated with an "s", and the nucleotide positions of the phosphorothioate internucleotide linkages are indicated in column 4. The 5th column of Table 9, "Nucleotide position 21-3'", represents the 3' most nucleotide of the siNA molecules of Table 9, each represented by "omeUSup" (for structure, see Table 16, infra). The SEQ ID NO: for each siNA molecule of Table 9 (positions 1-21) is provided in column 6.

TABLE 9

Single-stranded siNA molecules containing a 3dT or 3dTs nucleotide at position 1 and multiple phosphorothioate internucleotide linkages ("S-linkage").

| siNA name | 5'-position 1 nucleotide | Nucleotide sequence - position 2 to position 20 | Nucleotide position 21-3' | S-linkage nucleotide positions | SEQ ID NO. |
|---|---|---|---|---|---|
| 14S | p-3dTs | fluUs; omeU; fluCs; omeG; fluAs; omeA; fluUs; omeC; fluAs; omeA; fluUs; omeC; fluCs; omeAs; fluAs; omeCs; fluAs; omeGs; omeUs | omeUSup | 1, 2, 4, 6, 8, 10, 12, 14-20 | 41 |

TABLE 9-continued

Single-stranded siNA molecules containing a 3dT or 3dTs nucleotide at position 1 and multiple phosphorothioate internucleotide linkages ("S-linkage").

| siNA name | 5'-siNA position 1 nucleotide | Nucleotide sequence - position 2 to position 20 | Nucleotide position 21-3' | S-linkage nucleotide positions | SEQ ID NO. |
|---|---|---|---|---|---|
| 13S | p-3dTs | fluU; omeU; fluCs; omeG; fluAs; omeA; fluUs; omeC; fluAs; omeA; fluUs; omeC; fluCs; omeAs; fluAs; omeCs; fluAs; omeGs; omeUs | (same) | 1, 4, 6, 8, 10, 12, 14-20 | 42 |
| 12S | p-3dT | fluU; omeU; fluCs; omeG; fluAs; omeA; fluUs; omeC; fluAs; omeA; fluUs; omeC; fluCs; omeAs; fluAs; omeCs; fluAs; omeGs; omeUs | (same) | 4, 6, 8, 10, 12, 14-20 | 43 |
| 10S | p-3dT | fluU; omeU; fluC; omeG; fluA; omeA; fluU; omeC; fluA; omeAs; fluUs; omeCs; fluCs; omeAs; fluAs; omeCs; fluAs; omeGs; omeUs | (same) | 11-20 | 44 |
| 8S | p-3dT | fluU; omeU; fluC; omeG; fluA; omeA; fluU; omeC; fluA; omeA; fluU; omeCs; fluCs; omeAs; fluAs; omeCs; fluAs; omeGs; omeUs | (same) | 13-20 | 45 |
| 6S | p-3dT | fluU; omeU; fluC; omeG; fluA; omeA; fluU; omeC; fluA; omeA; fluU; omeC; fluC; omeAs; fluAs; omeCs; fluAs; omeGs; omeUs | (same) | 15-20 | 46 |
| 4S | p-3dT | fluU; omeU; fluC; omeG; fluA; omeA; fluU; omeC; fluA; omeA; fluU; omeC; fluC; omeA; fluA; omeCs; fluAs; omeGs; omeUs | (same) | 17-20 | 47 |

Results—

Figure 2B:
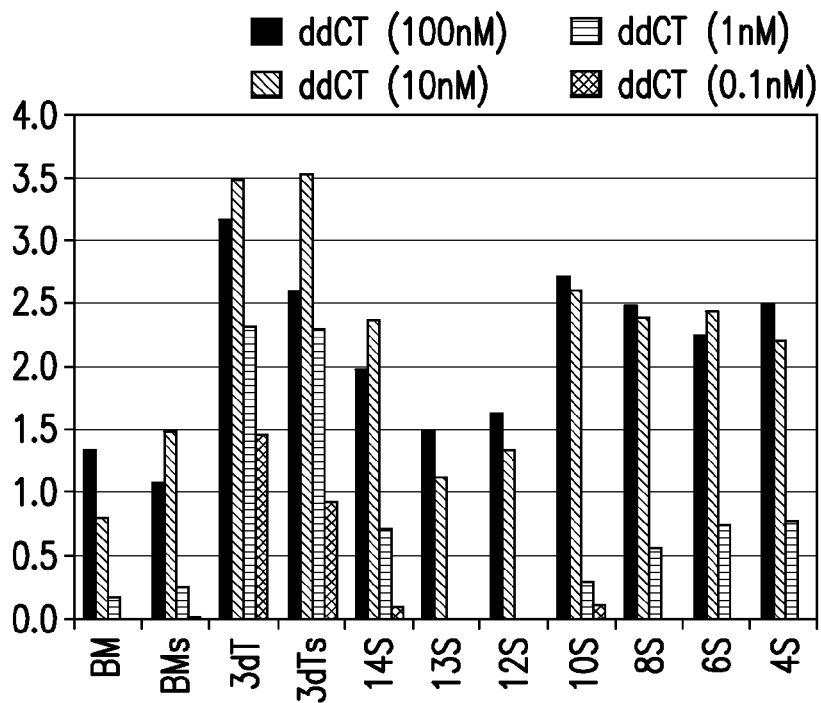
FIG. 2B compares knock-down activity (ddCT) of the single-stranded siNA molecules described in Table 10 at differing concentrations (100 nM, 10 nM, 1 nM and 0.1 nM). The knock-down activity was screened in Hepa1-6 cells transfected with RNAiMax (see Examples 6 and 8). The siNA molecules shown in this figure each contain a 2'-5' internucleoside linkage at position 1 and multiple phosphorothioate linkages.

The single-stranded siNA molecules of Table 9 were screened in Hepa1-6 cells transfected with RNAiMax, as in Example 6. Table 10 and FIG. 2B summarize the knock-down activities of these single-stranded siNA molecules containing multiple phosphorothioate incorporations and a 2'-5' linkage at position 1. Each of the single-stranded siNA molecules displayed knock-down activity in the assay that was equal to or better than that of the benchmark siNA molecules (BM, BMs). In particular, the 3dT and 3dTs siNA molecules showed higher knock down activities than any other single-stranded siNA molecules with multiple phosphorothioate incorporations at all four concentrations (100 nM, 10 nM, 1 nM, and 0.1 nM).

TABLE 10

In vitro transfection-based knock down activity for each of the single-stranded siNA molecules provided in Table 8, and BM, BMs, 3dT and 3dTs siNA molecules (see also FIG. 2B).

| siNA name | ddCT (100 nM) | ddCT (10 nM) | ddCT (1 nM) | ddCT (0.1 nM) |
|---|---|---|---|---|
| BM | 1.324 | 0.796 | 0.164 | −0.115 |
| BMs | 1.073 | 1.474 | 0.246 | 0.005 |
| 3dT | 3.168 | 3.474 | 2.316 | 1.45 |
| 3dTs | 2.593 | 3.519 | 2.291 | 0.92 |
| 14S | 1.982 | 2.376 | 0.717 | 0.095 |
| 13S | 1.479 | 1.114 | −0.048 | −0.040 |
| 12S | 1.642 | 1.336 | −0.016 | −0.055 |
| 10S | 2.729 | 2.609 | 0.309 | 0.115 |
| 8S | 2.477 | 2.391 | 0.579 | −0.017 |
| 6S | 2.274 | 2.449 | 0.754 | −0.022 |
| 4S | 2.504 | 2.216 | 0.794 | −0.023 |

Example 9: Double-Stranded siNA Molecules Containing Modifications at 5'-Position 1

Table 11 shows various chemically-modified double-stranded siNA molecules synthesized using the protocol provided in Examples 1 and 5. The double-stranded siNA molecules within Table 11 contain a sense strand (also known as the passenger strand) and an antisense strand (also known as the guide strand), wherein each strand is comprised of 21 nucleotides (position 1 (5') to position 21 (3')) and contains differential modifications at position 1. The name of each siNA molecule is provided in column 1 and corresponds to the composition of the nucleotide at position 1 of the sense and/or antisense strand of the duplex. Column 2 of Table 11, "Strand", indicates whether the particular sequence is the sense (S) or antisense (A/S) strand of the duplex. Column 3 of Table 11, "5-position 1 nucleotide", describes position 1 of the sense and antisense strands of the double-stranded siNA molecules of Table 11, each comprising of a nucleotide with a 5' cap. The chemical structure of each of the 5'-position 1 nucleotides is provided in Table 14, infra. The nucleotide sequence spanning positions 2-20 for each of the sense and antisense strands of the duplex siNA molecules is described in column 4 of Table 11, wherein the individual nucleotides are separated by a semicolon. The chemical structure of each nucleotide indicated within column 4 is provided for in Table 15, infra. The 5th column of Table 11, "Nucleotide position 21-3'", represents the 3' most nucleotide of the sense or antisense strand of the double-stranded siNA molecules, each represented by "omeU-iB-Sup" or "omeUSup" (for structures, see Table 16, infra). The SEQ ID NO: for each strand of the double-stranded siNA molecules of Table 11 (positions 1-21) is provided in column 6. Each siNA molecule in Table 11 has 3' overhangs at both ends of the molecule.

TABLE 11

Double-stranded siNA molecules, each containing a sense (S) and an antisense (A/S) strand that are 21 nucleotides in length and contain differential modifications at position 1.

| siNA name | Strand | 5'-position 1 nucleotide | Nucleotide sequence - position 2 to position 20 | Nucleotide position 21-3' | SEQ ID NO: |
|---|---|---|---|---|---|
| ds TGN BMs | S | tetraGalNAcLys-6amiL-iB-omeC | omeU; fluG; omeU; omeU; fluG; fluG; fluA; omeU; omeU; fluG; fluA; omeU; omeU; omeC; fluG; fluA; fluA; fluA; omeUs; | omeU-iBSup | 49 |

TABLE 11-continued

Double-stranded siNA molecules, each containing a sense (S) and an antisense (A/S) strand that are 21 nucleotides in length and contain differential modifications at position 1.

| siNA name | Strand | 5'-position 1 nucleotide | Nucleotide sequence - position 2 to position 20 | Nucleotide position 21-3' | SEQ ID NO: |
|---|---|---|---|---|---|
| | A/S | omeUs | fluUs; omeUs; fluC; omeG; fluA; omeA; fluU; omeC; fluA; omeA; fluU; omeC; fluC; omeA; fluA; omeC; fluA; omeG; omeUs | omeUSup | 48 |
| ds BMs | S | iB-omeC | (same as ds TGN BMs S strand) | omeU-iBSup | 50 |
| | A/S | p-omeUs | (same as ds TGN BMs A/S strand) | omeUSup | 51 |
| ds 3dT | S | iB-omeC | (same as ds TGN BMs S strand) | omeU-iBSup | 50 |
| | A/S | p-3dT | (same as ds TGN BMs A/S strand) | omeUSup | 52 |
| ds 3dTs | S | iB-omeC | (same as ds TGN BMs S strand) | omeU-iBSup | 50 |
| | A/S | p-3dTs | (same as ds TGN BMs A/S strand) | omeUSup | 53 |
| ds dT | S | iB-omeC | (same as ds TGN BMs S strand) | omeU-iBSup | 50 |
| | A/S | p-dT | (same as ds TGN BMs A/S strand) | omeUSup | 54 |
| ds dTs | S | iB-omeC | (same as ds TGN BMs S strand) | omeU-iBSup | 50 |
| | A/S | p-dTs | (same as ds TGN BMs A/S strand) | omeUSup | 55 |
| ds TGN vinylP-omeU | S | tetraGalNAcLys-6amiL-iB-omeC | (same as ds TGN BMs S strand) | omeU-iBSup | 49 |
| | A/S | vinylP-omeU | (same as ds TGN BMs A/S strand) | omeUSup | 56 |
| ds TGN vinylP-omeUs | S | tetraGalNAcLys-6amiL-iB-omeC | (same as ds TGN BMs S strand) | omeU-iBSup | 49 |
| | A/S | vinylP-omeUs | (same as ds TGN BMs A/S strand) | omeUSup | 57 |
| ds TGN vinylP-3dT | S | tetraGalNAcLys-6amiL-iB-omeC | (same as ds TGN BMs S strand) | omeU-iBSup | 49 |
| | A/S | vinylP3dT | (same as ds TGN BMs A/S strand) | omeUSup | 58 |
| ds TGN vinylP-3dTs | S | tetraGalNAcLys-6amiL-iB-omeC | (same as ds TGN BMs S strand) | omeU-iBSup | 49 |
| | A/S | vinylP-3dTs | (same as ds TGN BMs A/S strand) | omeUSup | 59 |
| ds TGN vinylP-moeT | S | tetraGalNAcLys-6amiL-iB-omeC | (same as ds TGN BMs S strand) | omeU-iBSup | 49 |
| | A/S | vinylP-moeT | (same as ds TGN BMs A/S strand) | omeUSup | 60 |

Results—

The double-stranded siNA molecules of Table 11 were assayed in vitro for 12-point dose response curve as described in Example 6. Table 12 summarizes the knock-down activity of the double-stranded siNA molecules. New siNA molecules with 2'-5' linked nucleotides at position 1 of the antisense strand, such as ds 3dTs, ds TGN vinylP3dT, and ds TGN vinylP3dTs showed sub pico molar knock-down activity (IC50), which was at least 10 times more potent than siNA molecules with regular 3'-5' linked nucleotides at position 1 of the antisense strand, such as ds TGN BMs, ds BMs, and ds dTs. This high knock-down activity of the siNA molecules with 2'-5' linked nucleotides at position 1 of the antisense strand was even comparable to regular 3'-5' linked siNA molecules (position 1 of antisense strand) with non-hydrolysable phosphonic acid at 5'-end of anti-sense strand, such as ds TGN vinylPomeU and ds TGN vinylPomeUs,

TABLE 12

In vitro transfection-based knock down activity for a subset of the double-stranded siNA molecules provided in Table 11.

| siNA name | IC50 (pM) | Max KD (ddCT) |
|---|---|---|
| ds TGN BMs | 62 | −2.96 |
| ds BMs | 5.63 | −3.57 |
| ds 3dT | 0.68 | −3.48 |
| ds 3dTs | 0.17 | −3.51 |
| ds dTs | 5.38 | −3.66 |
| ds TGN vinylPomeU | 0.18 | −3.57 |
| ds TGN vinylPomeUs | 0.14 | −3.49 |
| ds TGN vinylP3dT | 0.33 | −3.49 |
| ds TGN vinylP3dTs | 0.36 | −3.68 |

Example 10: In Vivo Studies (Mice) with Double-Stranded siNA Molecules Containing Modifications at 5'-Position 1

Mice were dosed via subcutaneous injection with PBS control or GalNAc-conjugated siNAs at 5 mg/kg or 1 mg/kg. The animals were sacrificed 72 hrs after the dosing. Liver punches were collected for RNA purification. Total RNA was purified using RNeasy 96 kit (Qiagen, Cat#74182). cDNA is generated from total RNA using High Capacity cDNA Reverse Transcription Kit (Invitrogen Cat#: 4368813). Quantitative PCR reactions are performed with TaqMan Universal PCR Master Mix (Cat#: 4304437). Mouse CTNNBI TaqMan Gene Expression Assay (Mm00483033_ml) and mouse GAPDH TaqMan Gene Expression Assay were used to monitor the mRNA levels of both transcripts in liver tissue. The expression level of CTNNB 1 was normalized against GAPDH.

Results—

Subsets of the double-stranded siNA molecules of Table 11 were assayed in vivo (mice). The sense strands of these siNA molecules were linked to tetraGalNAc Lys which targets the asialoglycoprotein receptor expressed on the surface of hepatoma cell lines. Table 13 summarizes the knock-down activities of the siNA molecules. ds TGN BMs which was not linked to non-hydrolysable phosphorus showed low activity in both 5 mg/kg and 1 mg/kg dose regimen. Among the siNA molecules which were linked to non-hydrolysable phosphorus, both the siNA molecules with regular 3'-5' linked oligonucleotides at position 1, such as ds TGN vinylPmoeT, ds TGN vinylPomeU, and ds TGN vinyl-PomeUs, and the siNA molecules with new 2'-5' linked oligonucleotides, such as ds TGN vinylP3dT and ds TGN vinylP3dTs, showed comparably high knock down activity in both 5 mg/kg and 1 mg/kg dose regimen.

TABLE 13

In vivo mouse knock down activity (subcutaneous dose) for a subset of the double-stranded siNA molecules provided in Table 11.

| | % KD | |
| --- | --- | --- |
| siNA name | at 5 mg/kg | at 1 mg/kg |
| ds TGN BMs | 43.65 | 19.51 |
| ds TGN vinylPmoeT | 62.97 | 27.35 |
| ds TGN vinylP3dT | 62.64 | 22.04 |
| ds TGN vinylP3dTs | 64.21 | 21.03 |
| ds TGN vinylPomeU | 69.43 | 14.80 |
| ds TGN vinylPomeUs | 70.64 | 38.12 |

Example 11

Chemical structures of the chemically-modified nucleotides used to generate the single- and double-stranded siNA molecules exemplified in Examples 6-10.

TABLE 14

Structure of 5'-position 1 nucleotides contained within the single- or double-stranded siNA molecules exemplified in Tables 2, 7, 9 and/or 11.

| 5'-position 1 nucleotide | Structure |
| --- | --- |
| p-omeU | 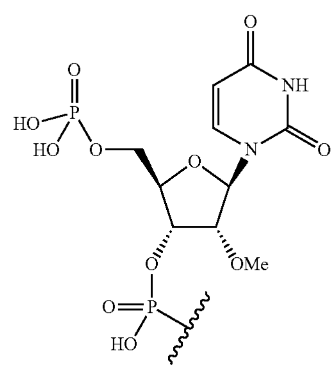 [SMILES: *P(=O)(O)O[C@H]1[C@@H](OC)[C@H](n2ccc(=O)[nH]c2=O)O[C@@H]1COP(=O)(O)O] |
| p-omeUs | 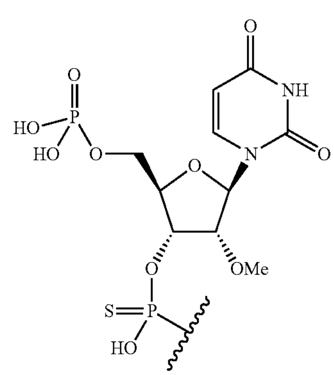 [SMILES: *P(O)(=S)O[C@H]1[C@@H](OC)[C@H](n2ccc(=O)[nH]c2=O)O[C@@H]1COP(=O)(O)O] |

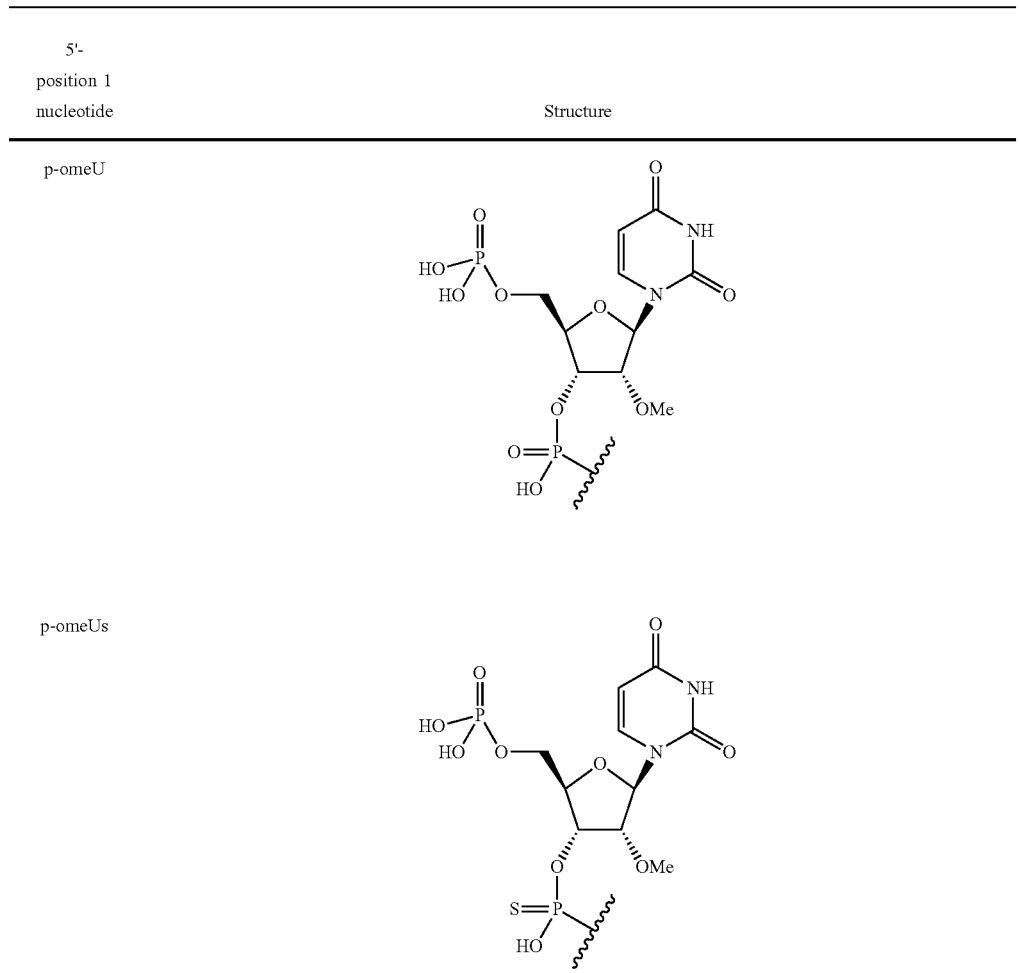

TABLE 14-continued

Structure of 5'-position 1 nucleotides contained within the single- or double-stranded siNA molecules exemplified in Tables 2, 7, 9 and/or 11.

| 5'-position 1 nucleotide | Structure |
|---|---|
| p-3dX<br>B = Base T, A, C, G | |
| p-3dXs<br>B = Base T, A, C, G | |
| p-dT | 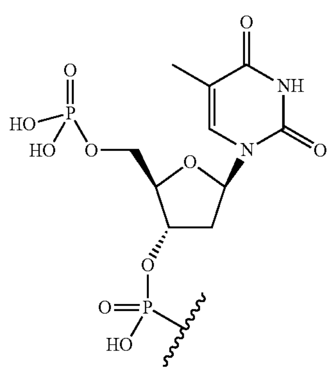 [SMILES: *P(=O)(O)O[C@H]1C[C@H](n2cc(C)c(=O)[nH]c2=O)O[C@@H]1COP(=O)(O)O] |
| p-dTs | 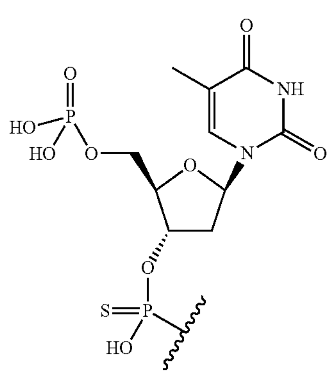 [SMILES: *P(O)(=S)O[C@H]1C[C@H](n2cc(C)c(=O)[nH]c2=O)O[C@@H]1COP(=O)(O)O] |

TABLE 14-continued

Structure of 5'-position 1 nucleotides contained within the single- or double-stranded siNA molecules exemplified in Tables 2, 7, 9 and/or 11.

| 5'-position 1 nucleotide | Structure |
|---|---|
| p-3priomeU | 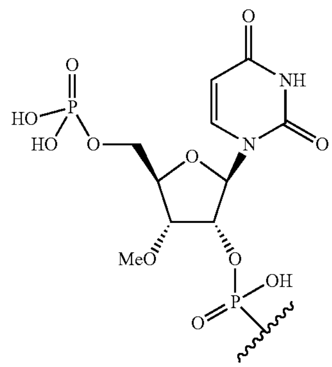 [SMILES: *P(=O)(O)O[C@@H]1[C@H](OC)[C@@H](COP(=O)(O)O)O[C@H]1n1ccc(=O)[nH]c1=O] |
| p-3priomeUs | 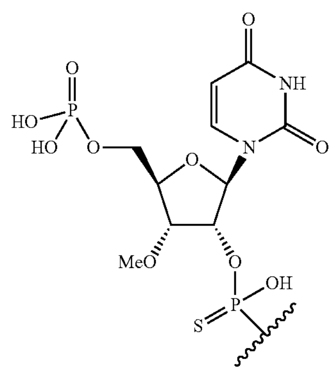 [SMILES: *P(O)(=S)O[C@@H]1[C@H](OC)[C@@H](COP(=O)(O)O)O[C@H]1n1ccc(=O)[nH]c1=O] |
| p-3fluU | 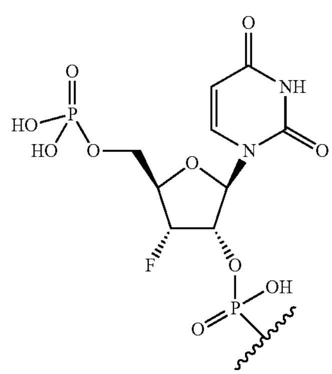 [SMILES: *P(=O)(O)O[C@@H]1[C@H](F)[C@@H](COP(=O)(O)O)O[C@H]1n1ccc(=O)[nH]c1=O] |
| p-3fluUs | 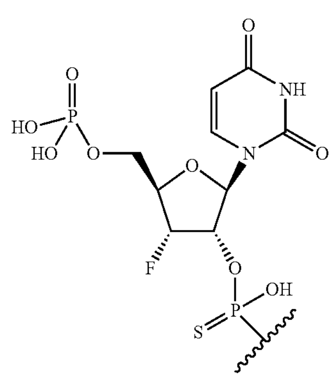 [SMILES: *P(O)(=S)O[C@@H]1[C@H](F)[C@@H](COP(=O)(O)O)O[C@H]1n1ccc(=O)[nH]c1=O] |

TABLE 14-continued
Structure of 5'-position 1 nucleotides contained within the single- or double-stranded siNA molecules exemplified in Tables 2, 7, 9 and/or 11.
| 5'-position 1 nucleotide | Structure |
|---|---|
| p-3daraT | 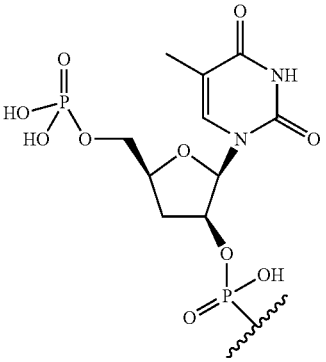 |
| p-3daraTs | 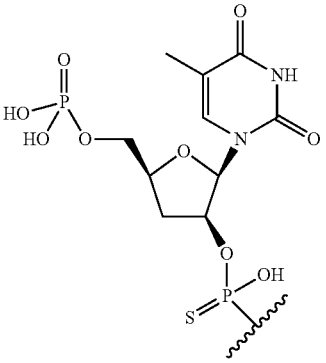 [SMILES: *P(=O)(O)O[C@H]1C[C@@H](COP(=O)(O)O)O[C@H]1n1cc(C)c(=O)[nH]c1=O] |
| p-3rT | 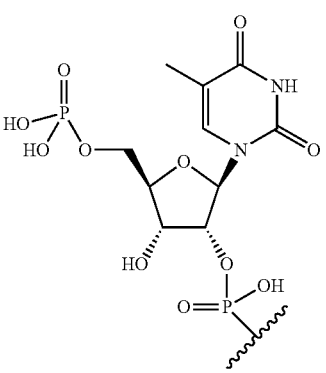 [SMILES: *P(O)(=S)O[C@@H]1[C@H](O)[C@@H](COP(=O)(O)O)O[C@H]1n1cc(C)c(=O)[nH]c1=O] |
| p-3rTs | 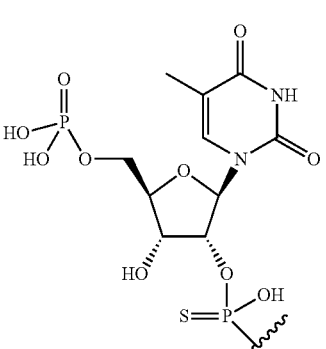 |

TABLE 14-continued
Structure of 5'-position 1 nucleotides contained within the single- or double-stranded siNA molecules exemplified in Tables 2, 7, 9 and/or 11.
| 5'-position 1 nucleotide | Structure |
|---|---|
| vinylP3dT | 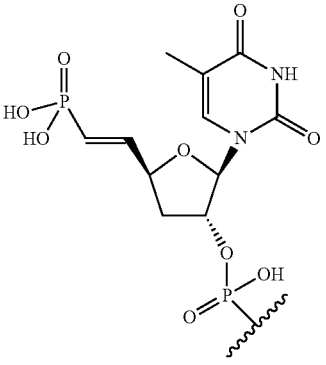 [SMILES: *P(=O)(O)O[C@@H]1C[C@@H](/C=C/P(=O)(O)O)O[C@H]1n1cc(C)c(=O)[nH]c1=O] |
| vinylP3dTs | 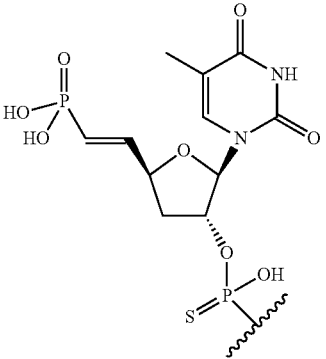 |
| vinylPmoeT | 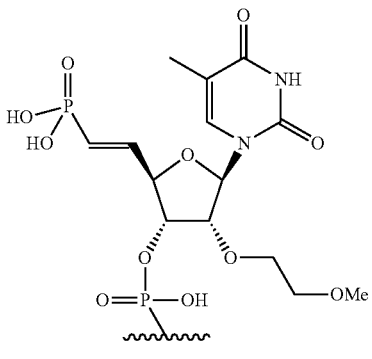 [SMILES: *P(=O)(O)O[C@H]1[C@@H](OCCOC)[C@H](n2cc(C)c(=O)[nH]c2=O)O[C@@H]1/C=C/P(=O)(O)O] |
| vinylPmoeTs | 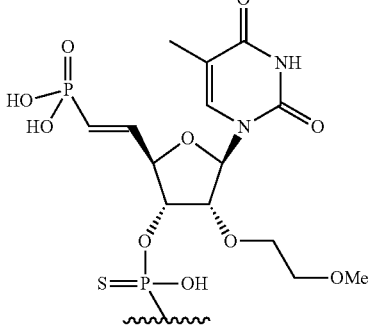 |

TABLE 14-continued

Structure of 5'-position 1 nucleotides contained within the single- or double-stranded siNA molecules exemplified in Tables 2, 7, 9 and/or 11.

| 5'-position 1 nucleotide | Structure |
|---|---|
| vinylPomeU | 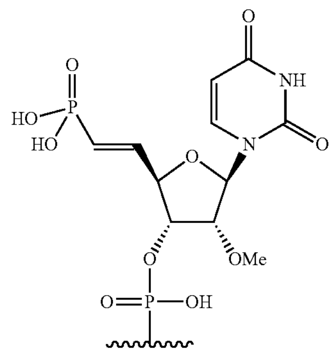 |
| vinylPomeUs | 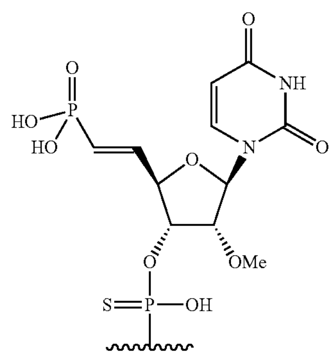 [SMILES: *P(O)(=S)O[C@H]1[C@@H](OC)[C@H](n2ccc(=O)[nH]c2=O)O[C@@H]1/C=C/P(=O)(O)O] |
| iB-omeC | 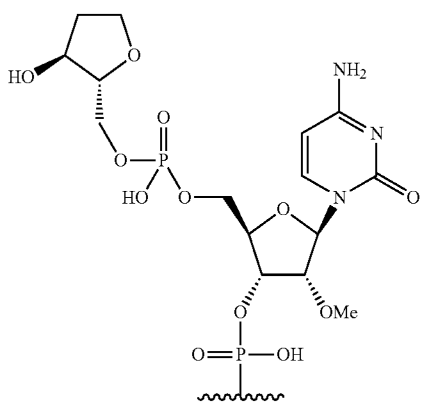 [SMILES: *P(=O)(O)O[C@H]1[C@@H](OC)[C@H](n2ccc(N)nc2=O)O[C@@H]1COP(=O)(O)OC[C@H]1OCC[C@@H]1O] |
| omeUs | 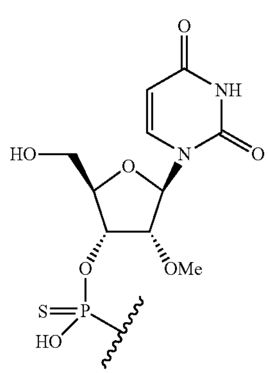 [SMILES: *P(O)(=S)O[C@H]1[C@@H](OC)[C@H](n2ccc(=O)[nH]c2=O)O[C@@H]1CO] |

TABLE 14-continued

Structure of 5'-position 1 nucleotides contained within the single- or double-stranded siNA molecules exemplified in Tables 2, 7, 9 and/or 11.

| 5'-position 1 nucleotide | Structure |
|---|---|
| tetraGalNAc Lys-6amiL-iB-omeC | (structure shown) |

TABLE 15

Structure of internally-located nucleotides (i.e., positions 2-20) contained within the single- or double-stranded siNA molecules exemplified in Tables 2, 7, 9 and/or 11.

| Internal nucleotide (positions 2-20) | Structure |
|---|---|
| omeX<br>X = B = Base<br>U, G, C, A | (structure shown) |
| omeXs<br>X = B = Base<br>U, G, C, A | (structure shown) |
| 3dX<br>X = B = Base<br>T, G, C, A | (structure shown) |
| 3dXs<br>X = B = Base<br>T, G, C, A | (structure shown) |

TABLE 15-continued

Structure of internally-located nucleotides (i.e., positions 2-20) contained within the single- or double-stranded siNA molecules exemplified in Tables 2, 7, 9 and/or 11.

| Internal nucleotide (positions 2-20) | Structure |
|---|---|
| fluX<br>X = B = Base<br>U, G, C, A | (structure shown) |
| fluXs<br>X = B = Base<br>U, G, C, A | (structure shown) |

TABLE 16

Structure of nucleotide position 21-3' nucleotides exemplified in Tables 2, 7, 9 and/or 11.

| Nucleotide position 21-3' | Structure |
|---|---|
| omeUsup | (structure shown) |
| omeU-iBSup | (structure shown) |

What is claimed is:

1. A short interfering nucleic acid (siNA) molecule capable of mediating RNA interference comprising an antisense strand that is complementary to a nucleic acid target, wherein said antisense strand comprises a 5' modified nucleotide having Formula II:

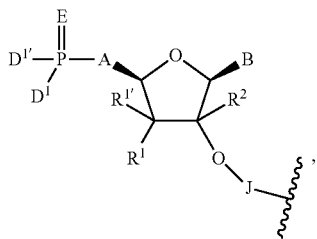

wherein:

A is —OC($R^3$)$_2$—, —C($R^3$)$_2$O—, —C($R^3$)$_2$—, —C($R^3$)$_2$C($R^3$)$_2$— or —C$R^3$=C$R^3$—;

B is any heterocyclic base moiety;

$D^1$ and $D^{1'}$ are independently selected from hydroxyl, —O$R^4$, —S$R^4$, or —N($R^4$)$_2$;

E is O, S, —N$R^5$, —N—N($R^4$)$_2$ or —N—O$R^4$;

J is an internucleoside linking group linking the 5' modified nucleotide of Formula II to the sugar moiety of an adjacent nucleotide of the siNA molecule;

$R^1$ and $R^{1'}$ are independently selected from H, hydroxyl, halogen, $C_{1-6}$ alkyl, —O$R^6$, —N($R^6$)$_2$, or together form =O or =CH$_2$;

$R^2$ is H, $C_{1-6}$ alkyl or $C_{2-6}$ alkenyl;

$R^3$ and $R^5$ are independently selected from H, hydroxyl, halogen, $C_{1-10}$ alkyl, $C_{2-6}$ alkenyl, $C_{2-6}$ alkynyl, aryl,

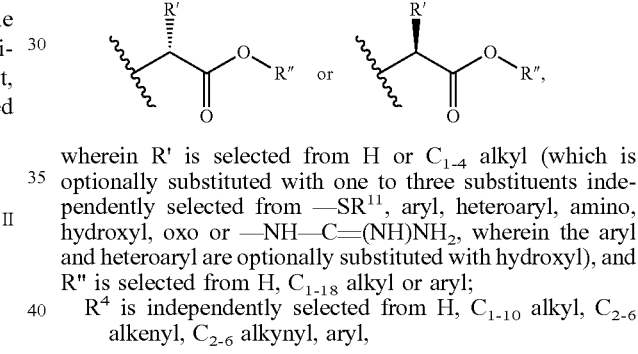

wherein R' is selected from H or $C_{1-4}$ alkyl (which is optionally substituted with one to three substituents independently selected from —S$R^{11}$, aryl, heteroaryl, amino, hydroxyl, oxo or —NH—C=(NH)NH$_2$, wherein the aryl and heteroaryl are optionally substituted with hydroxyl), and R" is selected from H, $C_{1-18}$ alkyl or aryl;

$R^4$ is independently selected from H, $C_{1-10}$ alkyl, $C_{2-6}$ alkenyl, $C_{2-6}$ alkynyl, aryl,

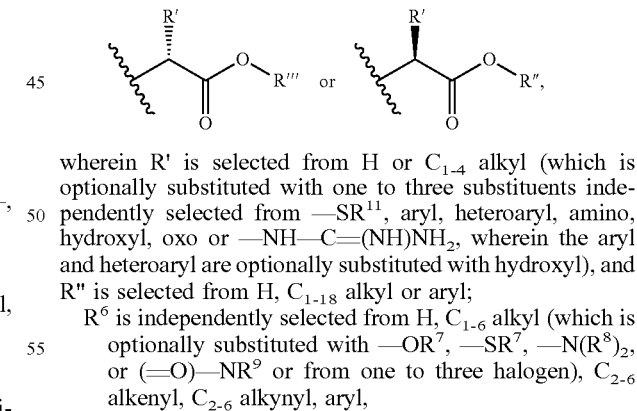

wherein R' is selected from H or $C_{1-4}$ alkyl (which is optionally substituted with one to three substituents independently selected from —S$R^{11}$, aryl, heteroaryl, amino, hydroxyl, oxo or —NH—C=(NH)NH$_2$, wherein the aryl and heteroaryl are optionally substituted with hydroxyl), and R" is selected from H, $C_{1-18}$ alkyl or aryl;

$R^6$ is independently selected from H, $C_{1-6}$ alkyl (which is optionally substituted with —O$R^7$, —S$R^7$, —N($R^8$)$_2$, or (=O)—N$R^9$ or from one to three halogen), $C_{2-6}$ alkenyl, $C_{2-6}$ alkynyl, aryl,

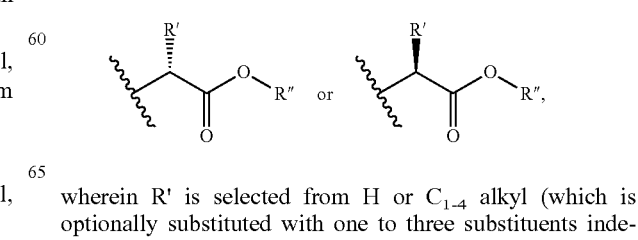

wherein R' is selected from H or $C_{1-4}$ alkyl (which is optionally substituted with one to three substituents independently selected from —SR$^{10}$, aryl, heteroaryl, amino, hydroxyl, oxo, —NH—C=(NH)NH$_2$, wherein the aryl and heteroaryl are optionally substituted with hydroxyl), and R" is selected from H, C$_{1-18}$ alkyl or aryl;

R$^7$ is methyl, —CF$_3$, —N(R$^8$)$_2$ or —CH$_2$—N(R$^8$)$_2$;
R$^8$ is independently selected from H or C$_{1-6}$ alkyl;
R$^9$ is (R$^8$)$_2$, —R$^8$—(CH$_2$)$_2$—N(R$^8$)$_2$ or —R$^8$—C(=NR$^8$)[N(R$^8$)$_2$]; and,
R$^{10}$ is H or C$_{1-4}$ alkyl, wherein the siNA molecule is a single stranded antisense molecule, or wherein the siNA molecule is a double-stranded molecule comprising a sense strand that is complementary to the antisense strand; and wherein the single-stranded molecule is between 15 and 30 nucleotides in length or wherein the antisense strand and the sense strand are each independently 15 to 30 nucleotides in length.

2. The siNA molecule of claim 1, wherein R$^3$ is independently selected from H, hydroxy, F, Cl, C$_{1-6}$ alkyl, C$_{2-6}$ alkenyl, C$_{2-6}$ alkynyl, aryl,

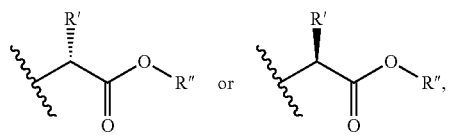

wherein R' is selected from H, C$_{1-4}$ alkyl,

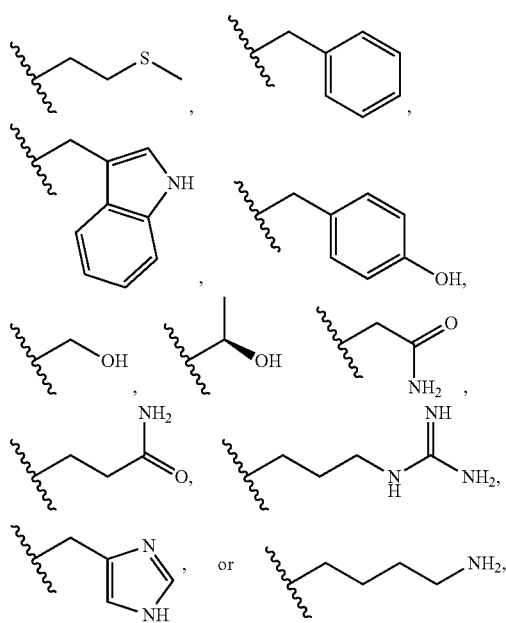

and R" is selected from H, C$_{1-4}$ alkyl or aryl.

3. The siNA molecule of claim 1, wherein A is —OCH$_2$—, —CH$_2$CH$_2$— or —CH=CH—.

4. The siNA molecule of claim 1, wherein D$^1$ and D$^{1'}$ is independently selected from hydroxyl, —OCH$_3$ or —OCH$_2$CH$_3$.

5. The siNA molecule of claim 1, wherein B is uracil, thymine, cytosine, 5-methylcytosine, adenine or guanine.

6. The siNA molecule of claim 1, wherein E is O.

7. The siNA molecule of claim 1, wherein J is a phosphodiester internucleoside linking group or a phosphorothioate internucleoside linking group.

8. The siNA molecule of claim 1, wherein R$^1$ is H or hydroxyl, and R1': is H, hydroxyl, halogen or —OR$^6$.

9. The siNA molecule of claim 1, wherein R$^1$, R$^{1'}$ and R$^2$ are each H.

10. The siNA molecule of claim 1, wherein the 5' modified nucleotide is

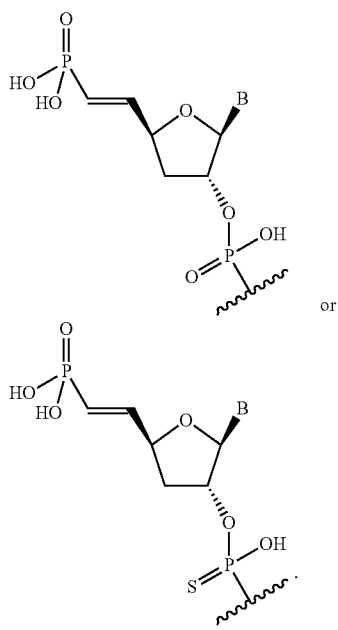

11. The siNA molecule claim 10, wherein B is thymine.

12. The siNA molecule of claim 1, wherein the siNA molecule is a single-stranded, antisense molecule.

13. The siNA molecule of claim 12, wherein the siNA molecule comprises one or more additional chemically-modified nucleotides.

14. The siNA molecule of claim 1, wherein the siNA molecule is a double-stranded molecule comprising a sense strand that is complementary to the antisense strand.

15. The siNA molecule of claim 14, wherein the siNA molecule comprises one or more additional chemically-modified nucleotides.

16. A composition comprising the siNA molecule of claim 1 in a pharmaceutically acceptable carrier or diluent.

* * * * *

SEQUENCE LISTING

```
<160> NUMBER OF SEQ ID NOS: 60

<210> SEQ ID NO 1
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
```

```
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 1
uuucgaauca auccaacagu u                                            21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
```

-continued

```
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
```

```
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 2
uuucgaauca auccaacagu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
```

```
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 3
tuucgaauca auccaacagu u                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
```

-continued

```
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 4
tuucgaauca auccaacagu u                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
```

```
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 5
tuucgaauca auccaacagu u                                                  21
```

```
<210> SEQ ID NO 6
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
```

```
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 6
tuucgaauca auccaacagu u                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
```

```
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 7
auucgaauca auccaacagu u                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
```

```
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 8
auucgaauca auccaacagu u                                                   21

<210> SEQ ID NO 9
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

```
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
```

<222> LOCATION: (20)..(21)
<223> OTHER INFORMATION: phosphorothioate internucleotide linkage

<400> SEQUENCE: 9
cuucgaauca auccaacagu u    21

<210> SEQ ID NO 10
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:

```
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 10
cuucgaauca auccaacagu u                                              21

<210> SEQ ID NO 11
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
```

```
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 11
guucgaauca auccaacagu u                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
```

```
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 12
guucgaauca auccaacagu u                                              21

<210> SEQ ID NO 13
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
```

-continued

```
<222> LOCATION: (1)..(1)
<223> OTHER INFORMATION: 3'-O-methyl; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
```

<400> SEQUENCE: 13
uuucgaauca auccaacagu u                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-O-methyl; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro -continued

```
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 14
uuucgaauca auccaacagu u                                              21

<210> SEQ ID NO 15
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-fluoro; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
```

```
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 15
uuucgaauca auccaacagu u                                              21

<210> SEQ ID NO 16
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-fluoro; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
```

```
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 16
uuucgaauca auccaacagu u                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
```

-continued

```
<220> FEATURE:
<221> NAME/KEY: misc_feature
<222> LOCATION: (1)..(1)
<223> OTHER INFORMATION: 3'-deoxy; (2S)-2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
```

<223> OTHER INFORMATION: phosphorothioate internucleotide linkage

<400> SEQUENCE: 17
tuucgaauca auccaacagu u					21

<210> SEQ ID NO 18
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; (2S)-2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:

```
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 18
tuucgaauca auccaacagu u                                           21

<210> SEQ ID NO 19
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-hydroxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
```

<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 19
tuucgaauca auccaacagu u                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-hydroxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:

```
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 20
tuucgaauca auccaacagu u                                              21
```

```
<210> SEQ ID NO 21
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
```

```
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 21
tuucgaauca auccaacagu u                                           21

<210> SEQ ID NO 22
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
```

```
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 22
tuucgaauca auccaacagu u                                               21

<210> SEQ ID NO 23
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
```

```
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 23
tuucgaauca auccaacagu u                                              21

<210> SEQ ID NO 24
<211> LENGTH: 21
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: ribonucleotide unmodified or modified as
      described for this sequence
<220> FEATURE:
<221> NAME/KEY: misc_feature
<222> LOCATION: (3)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 3'-deoxy; 2'-internucleotide linkage
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
```

```
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 24
utucgaauca auccaacagu u                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: ribonucleotide unmodified or modified as
      described for this sequence
<220> FEATURE:
<221> NAME/KEY: misc_feature
<222> LOCATION: (4)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 3'-deoxy; 2'-internucleotide linkage
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
```

-continued

```
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 25
uutcgaauca auccaacagu u                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 3'-deoxy; 2'-internucleotide linkage
<220> FEATURE:
<221> NAME/KEY: misc_feature
```

<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 26
uuucgaauca auccaacagu u                                       21

<210> SEQ ID NO 27
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:

-continued

```
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 3'-deoxy; 2'-internucleotide linkage
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
```

<400> SEQUENCE: 27
uuucgaauca auccaacagu u					21

<210> SEQ ID NO 28
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 3'-deoxy; 2'-internucleotide linkage
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)

```
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 28
uuucgaauca auccaacagu u                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: ribonucleotide unmodified or modified as
      described for this sequence
<220> FEATURE:
<221> NAME/KEY: misc_feature
<222> LOCATION: (9)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 3'-deoxy; 2'-internucleotide linkage
<220> FEATURE:
<221> NAME/KEY: misc_feature
<222> LOCATION: (9)..(9)
<223> OTHER INFORMATION: 2'-O-methyl
```

```
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 29
uuucgaatca auccaacagu u                                              21

<210> SEQ ID NO 30
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
```

```
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 3'-deoxy; 2'-internucleotide linkage
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 30
uuucgaauca auccaacagu u                                            21

<210> SEQ ID NO 31
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
```

```
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 3'-deoxy; 2'-internucleotide linkage
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
```

<400> SEQUENCE: 31
uuucgaauca auccaacagu u                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: ribonucleotide unmodified or modified as
      described for this sequence
<220> FEATURE:
<221> NAME/KEY: misc_feature
<222> LOCATION: (13)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 3'-deoxy; 2'-internucleotide linkage
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature

```
-continued

<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 32
uuucgaauca atccaacagu u                                              21

<210> SEQ ID NO 33
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
```

-continued

```
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 3'-deoxy; 2'-internucleotide linkage
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 33
uuucgaauca auccaacagu u                                              21

<210> SEQ ID NO 34
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
```

```
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 3'-deoxy; 2'-internucleotide linkage
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 34
uuucgaauca auccaacagu u                                          21

<210> SEQ ID NO 35
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
```

```
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 3'-deoxy; 2'-internucleotide linkage
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 35
```
uuucgaauca auccaacagu u                                                      21

<210> SEQ ID NO 36
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 3'-deoxy; 2'-internucleotide linkage
<220> FEATURE:

```
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 36
uuucgaauca auccaacagu u                                         21

<210> SEQ ID NO 37
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
```

-continued

```
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 3'-deoxy; 2'-internucleotide linkage
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 37
uuucgaauca auccaacagu u                                              21

<210> SEQ ID NO 38
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
```

```
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 3'-deoxy; 2'-internucleotide linkage
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 38
uuucgaauca auccaacagu u                                              21

<210> SEQ ID NO 39
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
```

```
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 3'-deoxy; 2'-internucleotide linkage
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 39
uuucgaauca auccaacagu u                                              21

<210> SEQ ID NO 40
<211> LENGTH: 21
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (21)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
```

```
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: 3'-deoxy; 2'-internucleotide linkage
<220> FEATURE:
<221> NAME/KEY: misc_feature
<222> LOCATION: (21)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 40
uuucgaauca auccaacagt u                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
```

```
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (4)..(5)
<223> OTHER INFORMATION: phosphorothioate internucleotide linkage
<220> FEATURE:
<221> NAME/KEY: misc_feature
<222> LOCATION: (6)..(7)
<223> OTHER INFORMATION: phosphorothioate internucleotide linkage
<220> FEATURE:
<221> NAME/KEY: misc_feature
<222> LOCATION: (8)..(9)
<223> OTHER INFORMATION: phosphorothioate internucleotide linkage
<220> FEATURE:
<221> NAME/KEY: misc_feature
<222> LOCATION: (10)..(11)
<223> OTHER INFORMATION: phosphorothioate internucleotide linkage
<220> FEATURE:
<221> NAME/KEY: misc_feature
<222> LOCATION: (12)..(13)
<223> OTHER INFORMATION: phosphorothioate internucleotide linkage
<220> FEATURE:
<221> NAME/KEY: misc_feature
<222> LOCATION: (14)..(15)
<223> OTHER INFORMATION: phosphorothioate internucleotide linkage
<220> FEATURE:
<221> NAME/KEY: misc_feature
<222> LOCATION: (15)..(16)
```

```
<223> OTHER INFORMATION: phosphorothioate internucleotide linkage
<220> FEATURE:
<221> NAME/KEY: misc_feature
<222> LOCATION: (16)..(17)
<223> OTHER INFORMATION: phosphorothioate internucleotide linkage
<220> FEATURE:
<221> NAME/KEY: misc_feature
<222> LOCATION: (17)..(18)
<223> OTHER INFORMATION: phosphorothioate internucleotide linkage
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 41
tuucgaauca auccaacagu u                                            21

<210> SEQ ID NO 42
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
```

```
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (4)..(5)
<223> OTHER INFORMATION: phosphorothioate internucleotide linkage
<220> FEATURE:
<221> NAME/KEY: misc_feature
<222> LOCATION: (6)..(7)
<223> OTHER INFORMATION: phosphorothioate internucleotide linkage
<220> FEATURE:
<221> NAME/KEY: misc_feature
<222> LOCATION: (8)..(9)
<223> OTHER INFORMATION: phosphorothioate internucleotide linkage
<220> FEATURE:
<221> NAME/KEY: misc_feature
<222> LOCATION: (10)..(11)
<223> OTHER INFORMATION: phosphorothioate internucleotide linkage
<220> FEATURE:
<221> NAME/KEY: misc_feature
<222> LOCATION: (12)..(13)
<223> OTHER INFORMATION: phosphorothioate internucleotide linkage
<220> FEATURE:
<221> NAME/KEY: misc_feature
<222> LOCATION: (14)..(15)
<223> OTHER INFORMATION: phosphorothioate internucleotide linkage
<220> FEATURE:
<221> NAME/KEY: misc_feature
<222> LOCATION: (15)..(16)
<223> OTHER INFORMATION: phosphorothioate internucleotide linkage
<220> FEATURE:
<221> NAME/KEY: misc_feature
<222> LOCATION: (16)..(17)
<223> OTHER INFORMATION: phosphorothioate internucleotide linkage
<220> FEATURE:
<221> NAME/KEY: misc_feature
<222> LOCATION: (17)..(18)
<223> OTHER INFORMATION: phosphorothioate internucleotide linkage
```

-continued

```
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 42
tuucgaauca auccaacagu u                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
```

```
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (4)..(5)
<223> OTHER INFORMATION: phosphorothioate internucleotide linkage
<220> FEATURE:
<221> NAME/KEY: misc_feature
<222> LOCATION: (6)..(7)
<223> OTHER INFORMATION: phosphorothioate internucleotide linkage
<220> FEATURE:
<221> NAME/KEY: misc_feature
<222> LOCATION: (8)..(9)
<223> OTHER INFORMATION: phosphorothioate internucleotide linkage
<220> FEATURE:
<221> NAME/KEY: misc_feature
<222> LOCATION: (10)..(11)
<223> OTHER INFORMATION: phosphorothioate internucleotide linkage
<220> FEATURE:
<221> NAME/KEY: misc_feature
<222> LOCATION: (12)..(13)
<223> OTHER INFORMATION: phosphorothioate internucleotide linkage
<220> FEATURE:
<221> NAME/KEY: misc_feature
<222> LOCATION: (14)..(15)
<223> OTHER INFORMATION: phosphorothioate internucleotide linkage
<220> FEATURE:
<221> NAME/KEY: misc_feature
<222> LOCATION: (15)..(16)
<223> OTHER INFORMATION: phosphorothioate internucleotide linkage
<220> FEATURE:
<221> NAME/KEY: misc_feature
<222> LOCATION: (16)..(17)
<223> OTHER INFORMATION: phosphorothioate internucleotide linkage
<220> FEATURE:
<221> NAME/KEY: misc_feature
<222> LOCATION: (17)..(18)
<223> OTHER INFORMATION: phosphorothioate internucleotide linkage
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage
```

<400> SEQUENCE: 43
tuucgaauca auccaacagu u                                           21

<210> SEQ ID NO 44
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)

```
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (11)..(12)
<223> OTHER INFORMATION: phosphorothioate internucleotide linkage
<220> FEATURE:
<221> NAME/KEY: misc_feature
<222> LOCATION: (12)..(13)
<223> OTHER INFORMATION: phosphorothioate internucleotide linkage
<220> FEATURE:
<221> NAME/KEY: misc_feature
<222> LOCATION: (13)..(14)
<223> OTHER INFORMATION: phosphorothioate internucleotide linkage
<220> FEATURE:
<221> NAME/KEY: misc_feature
<222> LOCATION: (14)..(15)
<223> OTHER INFORMATION: phosphorothioate internucleotide linkage
<220> FEATURE:
<221> NAME/KEY: misc_feature
<222> LOCATION: (15)..(16)
<223> OTHER INFORMATION: phosphorothioate internucleotide linkage
<220> FEATURE:
<221> NAME/KEY: misc_feature
<222> LOCATION: (16)..(17)
<223> OTHER INFORMATION: phosphorothioate internucleotide linkage
<220> FEATURE:
<221> NAME/KEY: misc_feature
<222> LOCATION: (17)..(18)
<223> OTHER INFORMATION: phosphorothioate internucleotide linkage
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 44
tuucgaauca auccaacagu u                                             21

<210> SEQ ID NO 45
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
```

-continued

```
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (13)..(14)
<223> OTHER INFORMATION: phosphorothioate internucleotide linkage
```

```
<220> FEATURE:
<221> NAME/KEY: misc_feature
<222> LOCATION: (14)..(15)
<223> OTHER INFORMATION: phosphorothioate internucleotide linkage
<220> FEATURE:
<221> NAME/KEY: misc_feature
<222> LOCATION: (15)..(16)
<223> OTHER INFORMATION: phosphorothioate internucleotide linkage
<220> FEATURE:
<221> NAME/KEY: misc_feature
<222> LOCATION: (16)..(17)
<223> OTHER INFORMATION: phosphorothioate internucleotide linkage
<220> FEATURE:
<221> NAME/KEY: misc_feature
<222> LOCATION: (17)..(18)
<223> OTHER INFORMATION: phosphorothioate internucleotide linkage
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 45
tuucgaauca auccaacagu u                                             21

<210> SEQ ID NO 46
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
```

```
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (15)..(16)
<223> OTHER INFORMATION: phosphorothioate internucleotide linkage
<220> FEATURE:
<221> NAME/KEY: misc_feature
<222> LOCATION: (16)..(17)
<223> OTHER INFORMATION: phosphorothioate internucleotide linkage
<220> FEATURE:
<221> NAME/KEY: misc_feature
<222> LOCATION: (17)..(18)
<223> OTHER INFORMATION: phosphorothioate internucleotide linkage
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 46
tuucgaauca auccaacagu u                                                  21

<210> SEQ ID NO 47
<211> LENGTH: 21
<212> TYPE: DNA
```

-continued

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
```

```
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (17)..(18)
<223> OTHER INFORMATION: phosphorothioate internucleotide linkage
<220> FEATURE:
<221> NAME/KEY: misc_feature
<222> LOCATION: (18)..(19)
<223> OTHER INFORMATION: phosphorothioate internucleotide linkage
<220> FEATURE:
<221> NAME/KEY: misc_feature
<222> LOCATION: (19)..(20)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 47
tuucgaauca auccaacagu u                                              21

<210> SEQ ID NO 48
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
```

```
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 48
uuucgaauca auccaacagu u                                          21

<210> SEQ ID NO 49
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: tetra-N-acetylgalactosamine aminohexyl
      phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
```

```
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 49
cuguuggauu gauucgaaau u                                       21

<210> SEQ ID NO 50
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
```

-continued

```
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 50 cguuggauu gauucgaaau u                                           21

<210> SEQ ID NO 51
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
```

```
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 51
uuucgaauca auccaacagu u                                               21

<210> SEQ ID NO 52
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
```

```
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 52
tuucgaauca auccaacagu u                                           21

<210> SEQ ID NO 53
```

```
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
```

```
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 53
tuucgaauca auccaacagu u                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
```

-continued

```
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 54
tuucgaauca auccaacagu u                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal phosphate
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
```

```
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 55
tuucgaauca auccaacagu u                                        21

<210> SEQ ID NO 56
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
```

-continued

```
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
```

<223> OTHER INFORMATION: phosphorothioate internucleotide linkage

<400> SEQUENCE: 56
uuucgaauca auccaacagu u                                                    21

<210> SEQ ID NO 57
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature

```
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 57
uuucgaauca auccaacagu u                                             21

<210> SEQ ID NO 58
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
```

```
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 58
tuucgaauca auccaacagu u                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (2)..(2)
<223> OTHER INFORMATION: 2'-deoxy-2'-fluoro
```

-continued

```
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage
```

<400> SEQUENCE: 59
tuucgaauca auccaacagu u                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro

```
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 60
tuucgaauca auccaacagu u                                           21
```